(12) United States Patent
Aoki et al.

(10) Patent No.: US 11,027,023 B2
(45) Date of Patent: Jun. 8, 2021

(54) NATURAL TYPE MIRNA FOR CONTROLLING GENE EXPRESSION, AND USE OF SAME

(71) Applicant: BONAC CORPORATION, Kurume (JP)

(72) Inventors: Eriko Aoki, Kurume (JP); Yasuhiko Yoshida, Kurume (JP); Shiori Kato, Kurume (JP); Tadaaki Ohgi, Kurume (JP)

(73) Assignee: BONAC CORPORATION, Kurume (JP)

( * ) Notice: Subject to any disclaimer, the term of this patent is extended or adjusted under 35 U.S.C. 154(b) by 407 days.

(21) Appl. No.: 15/539,226

(22) PCT Filed: Dec. 25, 2015

(86) PCT No.: PCT/JP2015/086378
§ 371 (c)(1),
(2) Date: Jun. 23, 2017

(87) PCT Pub. No.: WO2016/104775
PCT Pub. Date: Jun. 30, 2016

(65) Prior Publication Data
US 2018/0326091 A1    Nov. 15, 2018

(30) Foreign Application Priority Data

Dec. 27, 2014  (JP) .............................. JP2014-266918
Jun. 29, 2015  (JP) ................................. 2015-130496

(51) Int. Cl.
| | |
|---|---|
| *A61K 48/00* | (2006.01) |
| *A61K 47/18* | (2017.01) |
| *A61K 47/34* | (2017.01) |
| *A61K 47/42* | (2017.01) |
| *C12N 15/113* | (2010.01) |
| *A61K 31/7105* | (2006.01) |
| *A61P 35/00* | (2006.01) |

(52) U.S. Cl.
CPC ........ *A61K 48/005* (2013.01); *A61K 31/7105* (2013.01); *A61K 47/18* (2013.01); *A61K 47/34* (2013.01); *A61K 47/42* (2013.01); *A61K 48/00* (2013.01); *A61P 35/00* (2018.01); *C12N 15/113* (2013.01); *C12N 2310/141* (2013.01); *C12N 2310/318* (2013.01); *C12N 2310/3181* (2013.01); *C12N 2310/531* (2013.01); *C12N 2330/30* (2013.01)

(58) Field of Classification Search
CPC ................ A61K 31/713; C12Q 1/6886; C12Q 2600/158; C12Q 2600/178; C12N 2310/113; C12N 2310/141
USPC ............... 435/6.1, 91.1, 91.31, 455; 514/44; 536/23.1, 24.5
See application file for complete search history.

(56) References Cited

U.S. PATENT DOCUMENTS

| | | |
|---|---|---|
| 3,687,808 A | 8/1972 | Merigan, Jr. et al. |
| 4,550,163 A | 10/1985 | Voss et al. |
| 6,905,827 B2 | 6/2005 | Wohlgemuth et al. |
| 7,579,148 B2 | 8/2009 | Wohlgemuth et al. |
| 7,595,301 B2 | 9/2009 | Kunugiza et al. |
| 7,604,936 B2 | 10/2009 | Wohlgemuth et al. |
| 7,655,768 B2 | 2/2010 | Ohgi et al. |
| 7,771,950 B2 | 8/2010 | Wohlgemuth et al. |
| 8,110,364 B2 | 2/2012 | Wohlgemuth et al. |
| 8,691,782 B2 | 4/2014 | Ohgi et al. |
| 8,785,121 B2 | 7/2014 | Ohgi et al. |
| 8,933,046 B2 | 1/2015 | Machuy et al. |
| 9,206,422 B2 | 12/2015 | Ohgi et al. |
| 9,528,111 B2 | 12/2016 | Ohgi et al. |
| 9,663,784 B2 | 5/2017 | Ohgi et al. |
| 10,238,752 B2 | 3/2019 | Ohgi et al. |
| 2002/0042059 A1 | 4/2002 | Makarov et al. |
| 2002/0156261 A1 | 10/2002 | Malvy et al. |
| 2003/0059789 A1 | 3/2003 | Efimov et al. |
| 2003/0077608 A1 | 4/2003 | Coull et al. |
| 2003/0232355 A1 | 12/2003 | Norden et al. |

(Continued)

FOREIGN PATENT DOCUMENTS

| | | |
|---|---|---|
| CN | 1860228 A | 11/2006 |
| CN | 101076592 A | 11/2007 |

(Continued)

OTHER PUBLICATIONS

Trang et al., "Systemic Delivery of Tumor Suppressor microRNA Mimics Using a Neutral Lipid Emulsion Inhibits Lung Tumors in Mice," *Mol. Ther.*, 19(6): 1116-1122 (2011).

(Continued)

*Primary Examiner* — Jane J Zara
(74) *Attorney, Agent, or Firm* — Leydig, Voit & Mayer, Ltd.

(57) ABSTRACT

The present invention provides a natural type miRNA, which is a single-stranded nucleic acid containing X region and Y region, wherein the 3'-terminus of said X region and the 5'-terminus of said Y region are linked via a linker region of a non-nucleotide structure, the X region contains (a) a guide strand sequence or (b) a passenger strand sequence of a mature miRNA, when the X region contains (a), the Y region contains a passenger strand sequence of the mature miRNA, when the X region contains (b), the Y region contains a guide strand sequence of the mature miRNA, and the guide strand sequence and the passenger strand sequence form a double-stranded structure.

19 Claims, 13 Drawing Sheets

Specification includes a Sequence Listing.

(56) References Cited

U.S. PATENT DOCUMENTS

| | | |
|---|---|---|
| 2004/0009479 A1 | 1/2004 | Wohlgemuth et al. |
| 2004/0058886 A1 | 3/2004 | Scaringe |
| 2004/0110296 A1 | 6/2004 | Vargeese et al. |
| 2004/0241855 A1 | 12/2004 | Cullis et al. |
| 2005/0053979 A1 | 3/2005 | Livak et al. |
| 2005/0075492 A1 | 4/2005 | Chen et al. |
| 2005/0209141 A1 | 9/2005 | Silver et al. |
| 2005/0222009 A1 | 10/2005 | Lamensdorf et al. |
| 2005/0233455 A1 | 10/2005 | Damha et al. |
| 2006/0111312 A1 | 5/2006 | Eshleman et al. |
| 2006/0130176 A1 | 6/2006 | Reyes-Taboada et al. |
| 2006/0276421 A1 | 12/2006 | Kunugiza et al. |
| 2007/0037167 A1 | 2/2007 | Wohlgemuth et al. |
| 2007/0244058 A1 | 10/2007 | Ohgi et al. |
| 2007/0270365 A1 | 11/2007 | Jimenez et al. |
| 2008/0032918 A1 | 2/2008 | Silver et al. |
| 2008/0050744 A1 | 2/2008 | Brown et al. |
| 2008/0199853 A1 | 8/2008 | Wohlgemuth et al. |
| 2009/0005332 A1 | 1/2009 | Hauser et al. |
| 2009/0081274 A1 | 3/2009 | Silver et al. |
| 2009/0123501 A1 | 5/2009 | Levitt et al. |
| 2009/0130751 A1 | 5/2009 | Davidson et al. |
| 2009/0176723 A1 | 7/2009 | Brown et al. |
| 2009/0239814 A1 | 9/2009 | Manoharan et al. |
| 2009/0263796 A1 | 10/2009 | Wohlgemuth et al. |
| 2009/0292005 A1 | 11/2009 | Ohgi et al. |
| 2010/0009377 A1 | 1/2010 | Wohlgemuth et al. |
| 2010/0137407 A1 | 6/2010 | Abe et al. |
| 2010/0221266 A1* | 9/2010 | Gregory ............... C12N 15/111 424/174.1 |
| 2010/0292310 A1 | 11/2010 | Kelley et al. |
| 2010/0317714 A1 | 12/2010 | Xi et al. |
| 2011/0034545 A1 | 2/2011 | Kubo et al. |
| 2011/0052666 A1 | 3/2011 | Kaemmerer et al. |
| 2011/0055965 A1 | 3/2011 | Abe et al. |
| 2011/0064792 A1 | 3/2011 | Humphries et al. |
| 2011/0070584 A1 | 3/2011 | Wohlgemuth et al. |
| 2011/0159586 A1 | 6/2011 | Hauser |
| 2011/0190142 A1 | 8/2011 | Funke-Kaiser et al. |
| 2011/0200582 A1 | 8/2011 | Baryza et al. |
| 2011/0262914 A1 | 10/2011 | Wohlgemuth et al. |
| 2012/0004280 A1 | 1/2012 | Jadhav et al. |
| 2012/0010271 A1 | 1/2012 | Ohgi et al. |
| 2012/0021516 A1 | 1/2012 | Hannon et al. |
| 2012/0035246 A1 | 2/2012 | Ohgi et al. |
| 2012/0135521 A1 | 5/2012 | Eshleman et al. |
| 2012/0184598 A1 | 7/2012 | Hauser |
| 2013/0017223 A1 | 1/2013 | Hope et al. |
| 2013/0178514 A1 | 7/2013 | Deshmukh et al. |
| 2013/0179999 A1 | 7/2013 | Hannon et al. |
| 2013/0190494 A1 | 7/2013 | Carson et al. |
| 2013/0225652 A1 | 8/2013 | Chorn et al. |
| 2013/0253038 A1 | 9/2013 | Koizumi et al. |
| 2014/0171486 A1 | 6/2014 | Ohgi et al. |
| 2014/0171633 A1 | 6/2014 | Ohgi et al. |
| 2014/0329886 A1 | 11/2014 | Ohgi et al. |
| 2015/0073124 A1 | 3/2015 | Ohgi et al. |
| 2015/0105443 A1 | 4/2015 | Ohgi et al. |
| 2016/0319282 A1 | 11/2016 | Kuroda et al. |
| 2017/0037398 A1 | 2/2017 | Kuroda et al. |
| 2017/0088837 A1* | 3/2017 | Singer ................... C12N 15/111 |
| 2017/0306325 A1 | 10/2017 | Ohgi et al. |
| 2018/0119151 A1 | 5/2018 | Aoki et al. |
| 2019/0010503 A1 | 1/2019 | Ishida et al. |
| 2019/0270707 A1* | 9/2019 | Baiocchi ............... C07D 209/88 |

FOREIGN PATENT DOCUMENTS

| | | |
|---|---|---|
| CN | 101121934 A | 2/2008 |
| CN | 101679962 A | 3/2010 |
| CN | 101981185 A | 2/2011 |
| CN | 101845071 B | 2/2012 |
| CN | 102559666 A | 7/2012 |
| CN | 102784398 A | 11/2012 |
| CN | 103052711 A | 4/2013 |
| CN | 103221549 A | 7/2013 |
| CN | 103370416 A | 10/2013 |
| DE | 873543 C | 4/1953 |
| EP | 1013770 A1 | 6/2000 |
| EP | 1669450 A1 | 6/2006 |
| EP | 2143792 A1 | 1/2010 |
| EP | 2233573 A1 | 9/2010 |
| EP | 2256191 A1 | 12/2010 |
| EP | 2302055 A1 | 3/2011 |
| EP | 1669450 B1 | 11/2011 |
| EP | 2431466 A1 | 3/2012 |
| EP | 2436767 A1 | 4/2012 |
| EP | 2527440 A1 | 11/2012 |
| EP | 2562257 A1 | 2/2013 |
| EP | 2647713 A1 | 10/2013 |
| EP | 2801617 A1 | 11/2014 |
| JP | 2004-524032 A | 8/2004 |
| JP | 2005-508634 A | 4/2005 |
| JP | 2005-521393 A | 7/2005 |
| JP | 2007-508030 A | 4/2007 |
| JP | 2007-516695 A | 6/2007 |
| JP | 2008-510786 A | 4/2008 |
| JP | 2008-519606 A | 6/2008 |
| JP | 2008-526213 A | 7/2008 |
| JP | 2008-220366 A | 9/2008 |
| JP | 2008-239596 A | 10/2008 |
| JP | 2008-278784 A | 11/2008 |
| JP | 2010-104368 A | 5/2010 |
| JP | 2010-527616 A | 8/2010 |
| JP | 2011-501662 A | 1/2011 |
| JP | 2011-504730 A | 2/2011 |
| JP | 2011-220969 A | 11/2011 |
| JP | 2013-055913 A | 3/2013 |
| JP | 2013-153736 A | 8/2013 |
| RU | 2410430 C2 | 1/2011 |
| WO | WO 1995/029241 A2 | 11/1995 |
| WO | WO 1998/016550 A1 | 4/1998 |
| WO | WO 2003/068798 A1 | 8/2003 |
| WO | WO 2003/079757 A2 | 10/2003 |
| WO | WO 2004/015075 A2 | 2/2004 |
| WO | WO 2004/015107 A2 | 2/2004 |
| WO | WO 2004/058886 A1 | 7/2004 |
| WO | WO 2004/090108 A2 | 10/2004 |
| WO | WO 2005/019453 A2 | 3/2005 |
| WO | WO 2005/030960 A1 | 4/2005 |
| WO | WO 2005/037317 A2 | 4/2005 |
| WO | WO 2006/022325 A1 | 3/2006 |
| WO | WO 2006/024880 A2 | 3/2006 |
| WO | WO 2006/074108 A2 | 7/2006 |
| WO | WO 2006/088490 A2 | 8/2006 |
| WO | WO 2006/137941 A2 | 12/2006 |
| WO | WO 2007/099981 A1 | 9/2007 |
| WO | WO 2007/131237 A2 | 11/2007 |
| WO | WO 2008/116094 A2 | 9/2008 |
| WO | WO 2008/137862 A2 | 11/2008 |
| WO | WO 2008/137867 A2 | 11/2008 |
| WO | WO 2008/140126 A1 | 11/2008 |
| WO | WO 2008/147839 A1 | 12/2008 |
| WO | WO 2009/000520 A1 | 12/2008 |
| WO | WO 2009/029690 A1 | 3/2009 |
| WO | WO 2009/054551 A2 | 4/2009 |
| WO | WO 2009/065022 A2 | 5/2009 |
| WO | WO 2009/073809 A2 | 6/2009 |
| WO | WO 2009/076321 A2 | 6/2009 |
| WO | WO 2009/102081 A1 | 8/2009 |
| WO | WO 2009/126563 A | 10/2009 |
| WO | WO 2009/143619 A2 | 12/2009 |
| WO | WO 2010/056737 A2 | 5/2010 |
| WO | WO 2010/058824 A1 | 5/2010 |
| WO | WO 2011/008730 A2 | 1/2011 |
| WO | WO 2011/009624 A1 | 1/2011 |
| WO | WO 2011/055888 A1 | 5/2011 |
| WO | WO 2011/076807 A2 | 6/2011 |
| WO | WO 2011/119887 A1 | 9/2011 |
| WO | WO 2011/132672 A1 | 10/2011 |
| WO | WO 2011/133889 A2 | 10/2011 |
| WO | WO 2012/005368 A1 | 1/2012 |
| WO | WO 2012/012676 A2 | 1/2012 |

(56) References Cited

FOREIGN PATENT DOCUMENTS

| | | | |
|---|---|---|---|
| WO | WO 2012/017919 A1 | 2/2012 | |
| WO | WO-2012017919 A1 * | 2/2012 | ........... C12N 15/113 |
| WO | WO 2012/030683 A1 | 3/2012 | |
| WO | WO 2012/074038 A1 | 6/2012 | |
| WO | WO 2012/106591 A1 | 8/2012 | |
| WO | WO 2013/077446 A1 | 5/2013 | |
| WO | WO 2013/103146 A1 | 7/2013 | |
| WO | WO 2003/072745 A2 | 9/2013 | |
| WO | WO 2013/133221 A1 | 9/2013 | |
| WO | WO-2013133221 A1 * | 9/2013 | ......... A61K 31/7105 |
| WO | WO 2012/161124 A1 | 11/2013 | |
| WO | WO 2013/166155 A1 | 11/2013 | |
| WO | WO 2013/180038 A1 | 12/2013 | |
| WO | WO 2014/190157 A1 | 11/2014 | |
| WO | WO 2015/093495 A1 | 6/2015 | |
| WO | WO 2015/099188 A1 | 7/2015 | |
| WO | WO-2015099187 A1 * | 7/2015 | |

OTHER PUBLICATIONS

Deiters, "Small Molecule Modifiers of the microRNA and RNA Interference Pathway," *AAPS J.*, 12(1): 51-60 (2009).
Takeshita et al., "Systemic Delivery of Synthetic MicroRNA-16 Inhibits the Growth of Metastatic Prostate Tumors via Downregulation of Multiple Cell-Cycle Genes," *Mol. Ther.*, 18(1): 181-187 (2010).
Japanese Patent Office, International Search Report in International Patent Application No. PCT/JP2015/086378 (dated Mar. 15, 2016).
Takaoka, "Natural Immunity and Viral Infection" (2011) [obtained at http://www.igm.hokudai.ac.jp/sci/files/innate_virus.pdf on Sep. 19, 2018].
Japanese Patent Office, Notice of Reasons for Refusal in Japanese Patent Application No. 2016-566558 (dated Oct. 2, 2018).
Genbank, "*Homo sapiens* catenin (cadherin-associated protein), beta 1, 88kDa (CTNNB1), transcript variant 1, mRNA," Accession No. NM_001904.3 (2010) [obtained at https://www.ncbi.nlm.nih.gov/nuccore/148228165?sat=14&satkey=4105514].
Ivashchenko et al., "Specific Features of System Silencing of Homologous Sequences in the Course of RNA Interference," *Uspekhi Sovremennoj Biologii*, 129(5): 419-439 (2009).
Müller (editor), *Nucleic Acids from A to Z: A Concise Encyclopedia*, entry for "micro-RNA (miRNA)," p. 197 (2008).
China National Intellectual Property Office, The Second Office Action in Chinese Patent Application No. 201480076467.2 (dated Jun. 5, 2019).
Japanese Patent Office, Office Action in Japanese Patent Application No. 2018-113017 (dated Jun. 11, 2019).
Japanese Patent Office, Office Action in Japanese Patent Application No. 2017-509942 (dated Jul. 2, 2019).
Russian Federal Service for Intellectual Property, Office Action in Russian Patent Application No. 2017126566 (dated Jun. 6, 2019).
Batenburg et al., "Combined Renin Inhibition/(Pro)Renin Receptor Blockade in Diabetic Retinopathy—a Study in Transgenic (mREN2)27 Rats," *PLoS One*, 9(6): e100954 (2014).
Danser et al., "Renin, Prorenin, and Immunoreactive Renin in Vitreous Fluid from Eyes With and Without Diabetic Retinopathy," *J. Clin. Endocrinol. Metabol.*, 68(1): 160-167 (1989).
Genbank, "*Homo sapiens* glyceraldehyde-3-phosphate dehydrogenase (GADPH), transcript variant 1, mRNA," Accession No. NM_002046 (2014) [obtained at www.ncbi.nlm.nih.gov on Oct. 7, 2019].
Genbank, "*Homo sapiens* ATPase H+ transporting accessory protein 2 (ATP6AP2), mRNA.," Accession No. NM_005765 (2019) [obtained at www.ncbi.nlm.nih.gov on Oct. 7, 2019].
Hamasaki et al., "Efficacy of a Novel Class of RNA Interference Therapeutic Agents," *PLoS One*, 7(8): e42655 (2012).
Kanda et al., "(Pro)renin receptor is associated with angiogenic activity in proliferative diabetic retinopathy," *Diabetologia*, 55: 3104-3443 (2012).
Kanda, "(Pro)renin Receptor in the Pathogenesis of Proliferative Diabetic Retinopathy," *Jpn. J. Ophthalmol.*, 118(11): 916-926 (2014).

Satofuka et al., "Suppression of Ocular Inflammation in Endotoxin-Induced Uveitis by Inhibiting Nonproteolytic Activation of Prorenin," *Invest. Ophthalmol. Vis. Sci.*, 47(6): 2686-2692 (2006).
Zuyeva et al., "Changes of retinal neurons and Muller glial cells in patients with type II diabetes in treatment of diabetic retinopathy with angiotensin-converting enzyme inhibitor," *Vestnik Oftamologii*, 129(3): 44-47 (2013).
European Patent Office, Extended European Search Report in European Patent Application No. 16881846 (dated Apr. 16, 2019).
Japanese Patent Office, International Search Report in International Patent Application No. PCT/JP2016/089216 (dated Mar. 28, 2017).
Russian Patent Office, Office Action and Search Report in Russian Patent Application No. 2018127481 (dated Mar. 27, 2019).
China National Intellectual Property Office, Office Action and Search Report in Chinese Patent Application No. 201180027223.1 (dated Nov. 21, 2013).
China National Intellectual Property Office, Office Action and Search Report in Chinese Patent Application No. 201180037592.9 (dated Sep. 23, 2014).
China National Intellectual Property Office, Office Action and Search Report in Chinese Patent Application No. 201480070373.4 (dated Mar. 30, 2018).
NCBI, "*Homo sapiens* renin (REN), mRNA," NCBI Reference Sequence No. NM_000537.4 (2019).
Tarantul et al., "Single-stranded DNA (ssDNA)," Slovar biotekhnologicheskikh terminov (Dictionary of Bioengineering Terms), publication page and entry p. 478 (2009).
U.S. Appl. No. 13/254,150, filed Aug. 31, 2011.
U.S. Appl. No. 13/254,159, filed Aug. 31, 2011.
U.S. Appl. No. 14/134,704, filed Dec. 19, 2013.
U.S. Appl. No. 14/362,762, filed Jun. 4, 2014.
U.S. Appl. No. 14/403,259, filed Nov. 24, 2014.
U.S. Appl. No. 15/106,958, filed Jun. 21, 2016.
U.S. Appl. No. 15/108,453, filed Jun. 27, 2016.
U.S. Appl. No. 15/496,143, filed Apr. 25, 2017.
U.S. Appl. No. 15/562,231, filed Sep. 27, 2017.
U.S. Appl. No. 16/065,779, filed Jun. 22, 2018.
Abe et al., "Specific inhibition of influenza virus RNA polymerase and nucleoprotein gene expression by circular dumbbell RNA/DNA chimeric oligonucleotides containing antisense phosphodiester oligonucleotides," *FEBS Lett.*, 425(1): 91-96 (1998).
Abe et al., "Dumbbell-Shaped Nanocircular RNAs for RNA Interference," *J. Am. Chem. Soc.*, 129(49): 15108-15109 (2007).
Abe et al., "Synthesis, Structure, and Biological Activity of Dumbbell-Shaped Nanocircular RNAs for RNA Interference," *Bioconjug. Chem.*, 22(10): 2082-2092 (2011).
Anderson et al., "Bispecific Short Hairpin sRNA Constructs Targeted to CD4, CXCR4, and CCR5 Confer HIV-1 Resistance," *Oligonucleotides*, 13(5): 303-312 (2003).
Bailen et al., "Direct synthesis of hydroxamates from carboxylic acids using 2-mercaptopyridone-1-oxide-based thiouronium salts," *Tetrahedron Letters*, 42(30): 5013-5016 (2001).
Baumann et al., "miRNA-based therapies: strategies and delivery platforms for oligonucleotide and non-oligonucleotide agents," *Future Med. Chem.*, 6(17): 1967-1984 (2014).
Bosi et al., "Antimycobacterial Activity of Ionic Fullerene Derivatives," *Bioorg. Med. Chem. Lett.*, 10(10): 1043-1045 (2000).
Bradshaw et al., "A Simple and Convenient Method for the Preparation of N,N'-Dibenzyldiaza-crown Compounds," *Journal of Organic Chemistry*, 53(8): 1808-1810 (1988).
Bramsen et al., "Improved silencing properties using small internally segmented interfering RNAs," *Nucleic Acids Res.*, 35(17): 5886-5897 (2007).
Cifuentes et al., "A Novel miRNA Processing Pathway Independent of Dicer Requires Argonaute2 Catalytic Activity," *Science*, 328(5986): 1694-1698 (2010).
Cheloufi et al., "A Dicer-independent miRNA biogenesis pathway that requires Ago catalysis," *Nature*, 465(7298): 584-589 (2010).
Chen et al., "The hsa-let-7a miRNA Enhances Ara-C Induced Apoptosis in Human Acute Myeloid Leukemia Cells," *Clinical Lymphoma, Myeloma & Leukemia*, 13 (Supplement 2): S368, Abstract 203 (Sep. 2013).

(56) References Cited

OTHER PUBLICATIONS

Cheng et al., "TGF-β1 Gene Silencing for Treating Liver Fibrosis," *Mol. Pharm.*, 6(3): 772-779 (2009).
Chorn et al., "Single-stranded microRNA mimics," RNA, 18(10): 1796-1804 (2012).
Clusel et al., "Ex vivo regulation of specific gene expression by nanomolar concentration of double-stranded dumbbell oligonucleotides," *Nucleic Acids Res.*, 21(15): 3405-3411 (1993).
Collins et al., "The Schistosomicidal and Toxic Effects on Some αω-DI(p-aminopihenoxy)alkanes and Related Monoamines," *Br. J. Pharmacol. Chemother.*, 13(3): 238-243 (1958).
Confalone et al., "Design and Synthesis of Potential DNA Cross-Linking Reagents Based on the Anthramycin Class of Minor Groove Binding Compounds," *J. Org. Chem.*, 53(3): 482-487 (1988).
Dankwardt, "Solid Phase Synthesis of Hydroxamic Acids," *Synlett*, 1998(7): 761 (Jul. 1998).
De La Torre et al., "Synthesis of Oligonucleotides Carrying Anchoring Groups and Their Use in the Preparation of Oligonucleotide-Gold Conjugates," *Helvetica Chimica Acta*, 85: 2594-2607 (2002).
Elbashir et al., "Functional anatomy of siRNAs for mediating efficient RNAi in *Drosophila melanogaster* embryo lysate," *EMBO J.*, 20(23): 6877-6888 (2001).
Fire et al., "Potent and specific genetic interference by double-stranded RNA in *Caenorhabditis elegans*," *Nature*, 391: 806-811 (1998).
Gatto et al., "Syntheses and Binding Properties of Bibracchiai Lariat Ethers (BiBLEs): Survey of Synthetic Methods and Cation Selectivities." *J. Org. Chem.*, 51(26): 5373-5384 (1986).
Ge et al., "Minimal-length short hairpin RNAs: The relationship of structure and RNAi activity," *RNA*, 16(1): 106-117 (2010).
Genbank, "*Homo sapiens* periostin, osteoblast specific factor (POSTN), transcript variant 1, mRNA," Accession No. NM_006475.2 (2008).
Graubaum et al., "New Cryptands with 1,3,5-Triazines as Ring Building Blocks," *J. Prakt. Chem.*, 337(1): 534-537 (1995).
Guennewig et al., "Synthetic pre-microRNAs reveal dual-strand activity of miR-34a on TNF-α," *RNA*, 20(1): 61-75 (2013).
Hamazaki et al., "Inhibition of Influenza Virus Replication in MDCK Cells by Circular Dumbbell RNA/DNA Chimeras with Closed Alkyl Loop Structures," *Helvetica Chimica Acta*, 85(7): 2183-2194 (2002).
Hoogerhout et al., "Synthesis of fragments of the capsular polysaccharide of *Haemophilus influenzae* type B, comprising two or three repeating units," *Tetrahedron Letters*, 28(14): 1553-1556 (1987).
Hosoya et al., "Sequence-specific inhibition of a transcription factor by circular dumbbell DNA oligonucleotides," *FEBS Lett.*, 461(3): 136-140 (1999).
Ihara et al., "Enantioselective ester hydrolysis by hydroxamic acids of N-benzyloxycarbonyi-L-amino acids or optically active amines in cetyltrimethylammonium bromide," *Journal of Organic Chemistry*, 45(9): 1623-1625 (1980).
Jakobsen et al., "Polyaza crown ethers as nonnucleosidic building blocks in DNA-conjugates," 234th American Chemical Society (ACS) National Meeting, Abstract BIOL-071 (Aug. 19, 2007).
Jeong et al., "siRNA Conjugate Delivery Systems," *Bioconjug. Chem.*, 20(1): 5-14 (2009).
Johnson et al., "Somatic activation of the K-ras oncogene causes early onset lung cancer in mice," *Nature*, 410(6832): 1111-1116 (2001).
Kitamatsu et al., "Carrier PNA for shRNA delivery into cells," *Bioorg. Med. Chem. Lett.*, 19(13): 3410-3413 (2009).
Kumar et al., "Pyrrolidine Nucleic Acids: DNA/PNA Oligomers with 2-Hydroxy/Aminomethyl-4-(thymin-1-yl)pyrrolidine-N-acetic acid," *Org. Lett.*, 3(9): 1269-1272 (2001).
Kunugiza et al., "Inhibitory effect of ribbon-type NF-κB decoy oligodeoxynucleotides on osteoclast induction and activity in vitro and in vivo," *Arthritis Res. Ther.*, 8(4): R103 (2006).
Leirdal et al., "Gene silencing in mammalian cells by preformed small RNA duplexes," *Biochem. Biophys. Res. Commun.*, 295(3): 744-748 (2002).

Limbach et al., "Summary: the modified nucleosides of RNA," *Nucleic Acids Res.*, 22(12): 2163-2196 (1994).
Li et al., "miRNA arm selection and isomiR distribution in gastric cancer," *BMC Genomics*, 13(Suppl. 1): S13 (2012).
Liu et al., "Enhanced proliferation, invasion, and epithelial-mesenchymal transition of nicotine-promoted gastric cancer by periostin," *World J. Gastroenterol.*, 17(21): 2674-2680 (2011).
Liu et al., "Membrane Anchored Immunostimulatory Oligonucleotides for in Vivo Cell Modification and Localized Immunotherapy," *Angewandte Chemie, International Edition*, 50(31): 7052-7055 and supporting information (2011).
Lonkar et al., "Design and synthesis of conformationally frozen peptide nucleic acid backbone: chiral piperidine PNA as a hexitol nucleic acid surrogate," *Bloorg. Med. Chem. Lett.*, 14(9): 2147-2149 (2004).
Ma et al., "Designing Ago2-specific siRNA/shRNA to Avoid Competition with Endogenous miRNAs," *Mol. Ther. Nucleic Acids*, 3: e176 (2014).
Maeda et al., "Synthesis of N-Unsubstituted Di- and Triaza Crown Ethers," *Bulletin of the Chemical Society of Japan*, 56(10): 3073-3077 (1983).
Mäkilä et al., "Synthesis of multi-galactose-conjugated 2'-O-methyl oligoribonucleotides and their in vivo imaging with positron emission tomography," *Bioorg. Med. Chem.*, 22(24): 6806-6813 (2014).
McAnuff et al., "Potency of siRNA Versus shRNA Mediated Knockdown in Vivo," *J. Pharm. Sci.*, 96(11): 2922-2930 (2007).
McManus et al., "Gene silencing using micro-RNA designed hairpins," *RNA*, 8(6): 842-850 (2002).
Michlewski et al., "Posttranscriptional Regulation of miRNAs Harboring Conserved Terminal Loops," *Mol. Cell*, 32(3): 383-393 (2008).
Ming et al., "The Tumor Research Frontiers," *Fourth Military Medical University Press*, 10 (Chinese Edition): 25 (2010).
Myburgh et al., "Optimization of Critical Hairpin Features Allows miRNA-based Gene Knockdown Upon Single-copy Transduction," *Mol. Ther.—Nucleic Acids*, 3: e207 (2014).
Neilsen et al., "IsomiRs—the overlooked repertoire in the dynamic MicroRNAome," *Trends in Genetics*, 28(11): 544-549 (2012).
Nilsson et al., "Padlock probes: Circularizing Oligonucleotides for Localized DNA Detection," *Science*, 265(5181): 2085-2088 (1994).
Nitin et al., "Peptide-linked molecular beacons for efficient delivery and rapid mRNA detection in living cells," *Nucleic Acids Res.*, 32(6): e58 (2004).
Nitin et al., "NLS Peptide Conjugated Molecular Beacons for Visualizing Nuclear RNA in Living Cells," *Bioconjug. Chem.*, 19(11): 2205-2211 (2008).
Nykanen et al., "ATP Requirements and Small Interfering RNA Structure in the RNA Interference Pathway," *Cell*, 107(3): 309-321 (2001).
Oliveira et al., "Efficient and Expeditious Protocols for the Synthesis of Racemic and Enantiomerically Pure Endocyclic Enecarbamates from N-Acetyl Lactams and N-Acyl Pyrrolidines," *J. Org. Chem.*, 64(18): 6646-6652 (1999).
Paddison et al., "Short hairpin RNAs (shRNAs) induce sequence-specific silencing in mammalian cells," *Genes Dev.*, 16(8): 948-958 (2002).
Půschl et al., "Pyrrolidine PNA: A Novel Conformationally Restricted PNA Analogue," *Org. Lett.*, 2(26): 4161-4163 (2000).
Schmitter et al., "Effects of Dicer and Argonaute down-regulation on mRNA levels in human HEK293 cells," *Nucleic Acids Res.*, 34(17): 4801-4815 (2006).
Seo et al., "Cholesterol-Linked Fluorescent Molecular Beacons with Enhanced Cell Permeability," *Bioconjug. Chem.*, 17(5): 1151-1155 (2006).
She et al., "Organic and Biochemistry," *China Forestry Publishing House*, 3rd Edition (Chinese Edition), p. 280 (2009).
Shim et al., "Efficient and targeted delivery of siRNA in vivo," *FEBS J.*, 277(23): 4814-4827 (2010).
Sommer et al., "Synthesis of Potentially Cytoactive Amino Acid Amide Mustards," *Journal of Medicinal Chemistry*, 9(1): 84-88 (1966).

(56) References Cited

OTHER PUBLICATIONS

Sonoke et al., "Tumor Regression in Mice by Delivery of Bcl-2 Small Interfering RNA with Pegylated Cationic Liposomes," *Cancer Research*, 68(21): 8843-8851 (Nov. 1, 2008).
Teramoto et al., "Prediction of siRNA functionality using generalized string kernel and support vector machine," *FEBS Lett.*, 579(13): 2878-2882 (2005).
Upert et al., "Inhibition of HIV Replication by Cyclic and Hairpin PNAs Targeting the HIV-1 TAR RNA Loop," *J. Nucleic Acids*, 2012: 591025 (2012).
Völler et al., "Strong reduction of AGO2 expression in melanoma and cellular consequences," *Br. J. Cancer*, 109(12): 3116-3124 (2013).
Wang et al., "Predicting siRNA potency with random forests and support vector machines," *BMC Genomics*, 11(Suppl. 3): S2 (2010).
Watanabe et al., "Periostin regulates MMP-2 expression via the αvβ3 integrin/ERK pathway in human periodontal ligament cells," *Archives of Oral Biology*, 57(1): 52-59 (2012).
Webster et al., "Comparison of Solution-Phase and Solid-Phase Syntheses of a Restrained Proline-Containing Analogue of the Nodularin Macrocycle," *Tetrahedron Lett.*, 38(32): 5713-5716 (1997).
Winter et al., "Loop-miRs: active microRNAs generated from single-stranded loop regions," *Nucleic Acids Res.*, 41(10): 5503-5512 (2013).
Wu et al., "Improved siRNA/shRNA Functionality by Mismatched Duplex," *PLoS One*, 6(12): e28580 (2011).
Yamakawa et al. "Properties and Anti-HIV Activity of Nicked Dumbbell Oligonucleotides," *Nucleosides & Nucleotides*, 15(1-3): 519-529 (1996).
Yang et al., "Conserved vertebrate mir-451 provides a platform for Dicer-independent, Ago2-mediated microRNA biogenesis," *Proc. Natl. Acad. Sci U.S.A.*, 107(34): 15163-15168 (2010).
Yang et al., "Functional parameters of Dicer-independent microRNA biogenesis," *RNA*, 18(5): 945-957 (2012).
Yin et al., "HAS-miR-34a as a molecular marker for early diagnosis of renal cell carcinoma," *Modern Oncology*, 20(7): 1398-1401 (2012).
Yoshida et al., "Increased Expression of Periostin in Vitreous and Fibrovascular Membranes Obtained from Patients with Proliferative Diabetic Retinopathy," *Investigative Ophthalmology & Visual Science*, 52(8): 5670-5678 (2011).
Yu et al., "RNA interference by expression of short-interfering RNAs and hairpin RNAs in mammalian cells," *Proc. Natl. Acad. Sci. USA*, 99(9): 6047-6052 (2002).
Zeng et al., "Structural requirements for pre-microRNA binding and nuclear export by Exportin 5," *Nucleic Acids Res.*, 32(16): 4776-4785 (2004).
Zhu et al., "Targeted Delivery of siRNA to Hepatocytes and Hepatic Stellato Cells by Bioconjugation," *Bioconjug. Chem.*, 21(11): 2119-2127 (2010).
Australian Patent Office, Patent Examination Report No. 1 in Australian Patent Application No. 2011274854 (dated Oct. 24, 2014).
Chinese Patent Office, Office Action and Search Report in Chinese Patent Application No. 201180027223.1 (dated Nov. 21, 2013).
Chinese Patent Office, Office Action and Search Report in Chinese Patent Application No. 201180037592.9 (dated Sep. 23, 2014).
Chinese Patent Office, Notification of the Second Office Action in Chinese Patent Application No. 201380028696.2 (dated Jul. 18, 2016).
Chinese Patent Office, Office Action and Search Report in Chinese Patent Application No. 201480070373.4 (dated Mar. 30, 2018).
Chinese Patent Office, The First Office Action in Chinese Patent Application No. 201480076467.2 (dated Jul. 25, 2018).
European Patent Office, Supplementary European Search Report in European Patent Application No. 11746147.5 (dated Mar. 26, 2012).
European Patent Office, Communication Pursuant to Article 94(3) EPC in European Patent Application No. 11746147.5 (dated Apr. 20, 2012).
European Patent Office, Communication Pursuant to Article 94(3) EPC in European Patent Application No. 11746147.5 (dated Sep. 26, 2012).
European Patent Office, Communication Pursuant to Article 94(3) EPC in European Patent Application No. 11746147.5 (dated Mar. 25, 2013).
European Patent Office, Communication Pursuant to Article 94(3) EPC in European Patent Application No. 14873783.6 (dated Sep. 10, 2018).
European Patent Office, Supplementary European Search Report in European Patent Application No. 11748250.5 (dated Apr. 5, 2012).
European Patent Office, Communication Pursuant to Article 94(3) EPC in European Patent Application No. 11748250.5 (dated May 29, 2012).
European Patent Office, Supplementary European Search Report in European Patent Application No. 12864101.6 (dated Sep. 1, 2015).
European Patent Office, Extended European Search Report in European Patent Application No. 13184178.5 (dated Oct. 25, 2013).
European Patent Office, Extended European Search Report in European Patent Application No. 15169933.7 (dated Jul. 29, 2015).
European Patent Office, Extended European Search Report in European Patent Application No. 14873783.6 (dated Jul. 11, 2017).
European Patent Office, Extended European Search Report in European Patent Application No. 16772690.0 (dated Jan. 18, 2019).
European Patent Office, Communication Pursuant to Rule 164(1) EPC in European Patent Application No. 13167541.5 (dated Jul. 31, 2013).
European Patent Office, Communication Pursuant to Rule 164(1) EPC in European Patent Application No. 13797956.3 (dated Jan. 4, 2016).
Japanese Patent Office, International Search Report in International Patent Application No. PCT/JP2012/080461 (dated Jan. 22, 2013).
Japanese Patent Office, International Search Report in International Patent Application No. PCT/JP2012/084247 (dated Apr. 16, 2013).
Japanese Patent Office, International Search Report in International Patent Application No. PCT/JP2013/059494 (dated Jun. 4, 2013).
Japanese Patent Office, International Search Report in International Patent Application No. PCT/JP2013/064541 (dated Jul. 2, 2013).
Japanese Patent Office, International Search Report in International Patent Application No. PCT/JP2014/084724 (dated Mar. 24, 2015).
Japanese Patent Office, Notice of Reasons for Refusal in Japanese Patent Application No. 2014-518427 (dated May 17, 2016).
Japanese Patent Office, International Search Report in International Patent Application No. PCT/JP2016/059779 (dated Jun. 7, 2016).
Japanese Patent Office, Notification of Reasons for Refusal in Japanese Patent Application No. 2015-555042 (dated Dec. 4, 2018).
U.S. Patent and Trademark Office, Supplemental Structure Search Results (ACS on STN) Referring to WO 2009/000520, HCAPLUS Accession No. 2009: 1297, Document No. 150: 95775, in U.S. Appl. No. 13/254,159 (Nov. 9, 2012).
United States Patent and Trademark Office, Office Action in U.S. Appl. No. 13/254,159 (dated Nov. 21, 2012).
United States Patent and Trademark Office, Office Action in U.S. Appl. No. 14/135,468 (dated May 8, 2015).

\* cited by examiner

SEQUENCE LISTING

<160> NUMBER OF SEQ ID NOS: 81

<210> SEQ ID NO 1
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 1
uggcaguguc uuagcgguu gu                                              22

<210> SEQ ID NO 2
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 2
caaucagcaa guauacugcc cu                                             22

<210> SEQ ID NO 3
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 3
ugagguagua gguuguauag uu                                             22

<210> SEQ ID NO 4
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 4
cuauacaauc uacugucuuu c                                              21

<210> SEQ ID NO 5
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 5
ugagguagua gauuguauag uu                                             22

<210> SEQ ID NO 6
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 6
cuauacaauc uauugccuuc cc                                             22

<210> SEQ ID NO 7
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 7
ucucccaacc cuuguaccag ug                                             22

<210> SEQ ID NO 8
<211> LENGTH: 22
<212> TYPE: RNA
<213> ORGANISM: Artificial Sequence

```
<220> FEATURE:
<223> OTHER INFORMATION: Synthetic oligonucleotide

<400> SEQUENCE: 8
cugguacagg ccuggggac ag                                              22

<210> SEQ ID NO 9
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 9
uagcaccauu ugaaaucagu guu                                            23

<210> SEQ ID NO 10
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 10
gcugguuuca uauggugguu uaga                                           24

<210> SEQ ID NO 11
<211> LENGTH: 64
<212> TYPE: RNA
<213> ORGANISM: Artificial Sequence
<220> FEATURE:
<223> OTHER INFORMATION: Synthetic oligonucleotide

<400> SEQUENCE: 11
uggcaguguc uuagcugguu guugugagca auaguaagga agcaaucagc aaguauacug    60
cccu                                                                 64

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
uacuauucga cacgcgaagt t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
cuucgcgugu cgaauaguat t                                              21

<210> SEQ ID NO 14
<211> LENGTH: 45
<212> TYPE: RNA
<213> ORGANISM: Artificial Sequence
<220> FEATURE:
<223> OTHER INFORMATION: Synthetic oligonucleotide

<400> SEQUENCE: 14
```
uggcaguguc uuagcgguu guacaaucag caaguauacu gcccu         45

<210> SEQ ID NO 15
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 15
uggcaguguc uuagcugguu guuccggaac aaucagcaag uauacugccc u    51

<210> SEQ ID NO 16
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 16
uggcaguguc uuagcugguu guuccggccg gaacaaucag caaguauacu gcccu    55

<210> SEQ ID NO 17
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 17
uggcaguguc uuagcugguu guuccggccg gccggaacaa ucagcaagua uacugcccu    59

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
ctcaaccagg acgactccat         20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
agaccgcttc actcaggaaa         20

<210> SEQ ID NO 20
<211> LENGTH: 19
<212> TYPE: DNA
<213> ORGANISM: Artificial Sequence
<220> FEATURE:
<223> OTHER INFORMATION: Synthetic primer

<400> SEQUENCE: 20
atggggaagg tgaaggtcg          19

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
gggtcattga tggcaacaat atc                                              23

<210> SEQ ID NO 22
<211> LENGTH: 72
<212> TYPE: RNA
<213> ORGANISM: Artificial Sequence
<220> FEATURE:
<223> OTHER INFORMATION: Synthetic oligonucleotide

<400> SEQUENCE: 22
ugagguagua gguuguauag uuuuagdgguc acacccacca cugggagaua acuauacaau      60
cuacugucuu uc                                                          72

<210> SEQ ID NO 23
<211> LENGTH: 45
<212> TYPE: RNA
<213> ORGANISM: Artificial Sequence
<220> FEATURE:
<223> OTHER INFORMATION: Synthetic oligonucleotide

<400> SEQUENCE: 23
ugagguagua gguuguauag uuaacuauac aaucuacugu cuuuc                      45

<210> SEQ ID NO 24
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 24
ugagguagua gguuguauag uuuccggaaa cuauacaauc uacugucuuu c                51

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
gaagccactg gagaaaaacg                                                  20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
cttcggcaga ctcttgtgag                                                  20

<210> SEQ ID NO 27
<211> LENGTH: 64
<212> TYPE: RNA
<213> ORGANISM: Artificial Sequence
<220> FEATURE:
<223> OTHER INFORMATION: Synthetic oligonucleotide

<400> SEQUENCE: 27
gcugguuuca uauggugguu uagauuuaaa uagugauugu cuagcaccau uugaaaucag    60
uguu    64

<210> SEQ ID NO 28
<211> LENGTH: 49
<212> TYPE: RNA
<213> ORGANISM: Artificial Sequence
<220> FEATURE:
<223> OTHER INFORMATION: Synthetic oligonucleotide

<400> SEQUENCE: 28
gcugguuuca uauggugguu uagaucuagc accauuugaa aucaguguu    49

<210> SEQ ID NO 29
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 29
gcugguuuca uauggugguu uagauccgga ucuagcacca uuugaaauca guuu    55

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
cccaaggaca agaggcatgt    20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
ccgccatact cgaactggaa    20

<210> SEQ ID NO 32
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 32
ugagguagua gguuguauag uuuccggccg gaaacuauac aaucuacugu cuuuc    55

<210> SEQ ID NO 33
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 33
gcugguuuca uauggugguu uagauccggc cggaucuagc accauuugaa aucaguguu    59

<210> SEQ ID NO 34
<211> LENGTH: 51

```
<212> TYPE: RNA
<213> ORGANISM: Artificial Sequence
<220> FEATURE:
<223> OTHER INFORMATION: Synthetic oligonucleotide

<400> SEQUENCE: 34
uggcaguguc uuagcugguu guuaauuaac aaucagcaag uauacugccc u          51

<210> SEQ ID NO 35
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 35
uggcaguguc uuagcugguu guugguuaac aaucagcaag uauacugccc u          51

<210> SEQ ID NO 36
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 36
uggcaguguc uuagcugguu gucggccgac aaucagcaag uauacugccc u          51

<210> SEQ ID NO 37
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 37
uggcaguguc uuagcugguu gucaauugac aaucagcaag uauacugccc u          51

<210> SEQ ID NO 38
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 38
uggcaguguc uuagcugguu gucgguugac aaucagcaag uauacugccc u          51

<210> SEQ ID NO 39
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 39
uggcaguguc uuagcugguu guuggccgac aaucagcaag uauacugccc u          51

<210> SEQ ID NO 40
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 40
```
uggcaguguc uuagcugguu guuaauugac aaucagcaag uauacugccc u        51

<210> SEQ ID NO 41
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 41
uggcaguguc uuagcugguu guugguugac aaucagcaag uauacugccc u        51

<210> SEQ ID NO 42
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 42
uggcaguguc uuagcugguu guuaauuaau uaacaaucag caaguauacu gcccu    55

<210> SEQ ID NO 43
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 43
uggcaguguc uuagcugguu guuaauuaau uaauuaacaa ucagcaagua uacugcccu    59

<210> SEQ ID NO 44
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 44
gcugguuuca uauggugguu uagauaauua ucuagcacca uuugaaauca guguu    55

<210> SEQ ID NO 45
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 45
gcugguuuca uauggugguu uagaugguua ucuagcacca uuugaaauca guguu    55

<210> SEQ ID NO 46
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 46
gcugguuuca uauggugguu uagacggccg ucuagcacca uuugaaauca guguu    55

<210> SEQ ID NO 47
<211> LENGTH: 55
<212> TYPE: RNA
<213> ORGANISM: Artificial Sequence

```
<220> FEATURE:
<223> OTHER INFORMATION: Synthetic oligonucleotide

<400> SEQUENCE: 47
gcugguuuca uauggugguu uagacaauug ucuagcacca uuugaaauca guguu          55

<210> SEQ ID NO 48
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 48
gcugguuuca uauggugguu uagacgguug ucuagcacca uuugaaauca guguu          55

<210> SEQ ID NO 49
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 49
gcugguuuca uauggugguu uagauggccg ucuagcacca uuugaaauca guguu          55

<210> SEQ ID NO 50
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 50
gcugguuuca uauggugguu uagauaauug ucuagcacca uuugaaauca guguu          55

<210> SEQ ID NO 51
<211> LENGTH: 55
<212> TYPE: RNA
<213> ORGANISM: Artificial Sequence
<220> FEATURE:
<223> OTHER INFORMATION: Synthetic oligonucleotide

<400> SEQUENCE: 51
gcugguuuca uauggugguu uagaugguug ucuagcacca uuugaaauca guguu          55

<210> SEQ ID NO 52
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 52
gcugguuuca uauggugguu uagauaauua auuaucuagc accauuugaa aucaguguu      59

<210> SEQ ID NO 53
<211> LENGTH: 63
<212> TYPE: RNA
<213> ORGANISM: Artificial Sequence
<220> FEATURE:
<223> OTHER INFORMATION: Synthetic oligonucleotide

<400> SEQUENCE: 53
gcugguuuca uauggugguu uagauccggc cggccggauc uagcaccauu ugaaaucagu     60
```

-continued guu                                                           63

<210> SEQ ID NO 54
<211> LENGTH: 63
<212> TYPE: RNA
<213> ORGANISM: Artificial Sequence
<220> FEATURE:
<223> OTHER INFORMATION: Synthetic oligonucleotide

<400> SEQUENCE: 54
gcugguuuca uauggugguu uagauaauua auuaauuauc uagcaccauu ugaaaucagu    60
guu                                                           63

<210> SEQ ID NO 55
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 55
gcugguuuca uauggugguu uagauuuuua aaaaucuagc accauuugaa aucaguguu     59

<210> SEQ ID NO 56
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 56
gcugguuuca uauggugguu uagauuuuau aaaaucuagc accauuugaa aucaguguu     59

<210> SEQ ID NO 57
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 57
gcugguuuca uauggugguu uagauuuaua uaaaucuagc accauuugaa aucaguguu     59

<210> SEQ ID NO 58
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 58
gcugguuuca uauggugguu uagauuauua auaaucuagc accauuugaa aucaguguu     59

<210> SEQ ID NO 59
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 59
gcugguuuca uauggugguu uagauauuua aauaucuagc accauuugaa aucaguguu     59

<210> SEQ ID NO 60
<211> LENGTH: 59

```
<212> TYPE: RNA
<213> ORGANISM: Artificial Sequence
<220> FEATURE:
<223> OTHER INFORMATION: Synthetic oligonucleotide

<400> SEQUENCE: 60
gcugguuuca uauggugguu uagauuuaau uaaaucuagc accauuugaa aucaguguu      59

<210> SEQ ID NO 61
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 61
gcugguuuca uauggugguu uagauuauau auaaucuagc accauuugaa aucaguguu      59

<210> SEQ ID NO 62
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 62
gcugguuuca uauggugguu uagauauuau aauaucuagc accauuugaa aucaguguu      59

<210> SEQ ID NO 63
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 63
gcugguuuca uauggugguu uagauuaaua uuaaucuagc accauuugaa aucaguguu      59

<210> SEQ ID NO 64
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 64
gcugguuuca uauggugguu uagauauaua uauaucuagc accauuugaa aucaguguu      59

<210> SEQ ID NO 65
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 65
gcugguuuca uauggugguu uagauuaaau uuaaucuagc accauuugaa aucaguguu      59

<210> SEQ ID NO 66
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 66
```
gcugguuuca uauggugguu uagauauaau uauaucuagc accauuugaa aucaguguu    59

<210> SEQ ID NO 67
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 67
gcugguuuca uauggugguu uagauaaauau auuaucuagc accauuugaa aucaguguu    59

<210> SEQ ID NO 68
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 68
gcugguuuca uauggugguu uagauaaaua uuuaucuagc accauuugaa aucaguguu    59

<210> SEQ ID NO 69
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 69
gcugguuuca uauggugguu uagauaaaau uuuaucuagc accauuugaa aucaguguu    59

<210> SEQ ID NO 70
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 70
gcugguuuca uauggugguu uagauuuggu uaaaucuagc accauuugaa aucaguguu    59

<210> SEQ ID NO 71
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 71
gcugguuuca uauggugguu uagauuuuuu uaaaucuagc accauuugaa aucaguguu    59

<210> SEQ ID NO 72
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 72
gcugguuuca uauggugguu uagaauuaau uaauucuagc accauuugaa aucaguguu    59

<210> SEQ ID NO 73
<211> LENGTH: 59
<212> TYPE: RNA
<213> ORGANISM: Artificial Sequence

```
<220> FEATURE:
<223> OTHER INFORMATION: Synthetic oligonucleotide

<400> SEQUENCE: 73
gcugguuuca uauggugguu uagaauuuua aaauucuagc accauuugaa aucaguguu      59

<210> SEQ ID NO 74
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 74
gcugguuuca uauggugguu uagacuuaau uaagucuagc accauuugaa aucaguguu      59

<210> SEQ ID NO 75
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 75
gcugguuuca uauggugguu uagacuuuua aaagcuagc accauuugaa aucaguguu       59

<210> SEQ ID NO 76
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 76
gcugguuuca uauggugguu uagaguuaau uaacucuagc accauuugaa aucaguguu      59

<210> SEQ ID NO 77
<211> LENGTH: 59
<212> TYPE: RNA
<213> ORGANISM: Artificial Sequence
<220> FEATURE:
<223> OTHER INFORMATION: Synthetic oligonucleotide

<400> SEQUENCE: 77
gcugguuuca uauggugguu uagaguuuua aaacucuagc accauuugaa aucaguguu      59

<210> SEQ ID NO 78
<211> LENGTH: 57
<212> TYPE: RNA
<213> ORGANISM: Artificial Sequence
<220> FEATURE:
<223> OTHER INFORMATION: Synthetic oligonucleotide

<400> SEQUENCE: 78
gcugguuuca uauggugguu uagauaaauau uaucuagcac cauugaaau caguguu        57

<210> SEQ ID NO 79
<211> LENGTH: 57
<212> TYPE: RNA
<213> ORGANISM: Artificial Sequence
<220> FEATURE:
<223> OTHER INFORMATION: Synthetic oligonucleotide

<400> SEQUENCE: 79
gcugguuuca uauggugguu uagauuaauu aaucuagcac cauugaaau caguguu         57
```

```
<210> SEQ ID NO 80
<211> LENGTH: 57
<212> TYPE: RNA
<213> ORGANISM: Artificial Sequence
<220> FEATURE:
<223> OTHER INFORMATION: Synthetic oligonucleotide

<400> SEQUENCE: 80
gcugguuuca uauggugguu uagauugguu aaucuagcac cauuugaaau caguguu       57

<210> SEQ ID NO 81
<211> LENGTH: 57
<212> TYPE: RNA
<213> ORGANISM: Artificial Sequence
<220> FEATURE:
<223> OTHER INFORMATION: Synthetic oligonucleotide

<400> SEQUENCE: 81
gcugguuuca uauggugguu uagauuuuuu uaucuagcac cauuugaaau caguguu       57
```

NATURAL TYPE MIRNA FOR CONTROLLING GENE EXPRESSION, AND USE OF SAME

CROSS-REFERENCE TO RELATED APPLICATIONS

This patent application is the U.S. national phase of International Patent Application No. PCT/JP2015/086378, filed Dec. 25, 2015, which claims the benefit of Japanese Patent Application No. 2014-266918, filed on Dec. 27, 2014, and Japanese Patent Application No. 2015-130496, filed Jun. 29, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 16,613 bytes ASCII (Text) file named "728991SequenceListing.txt," created Jun. 22, 2017.

TECHNICAL FIELD

The present invention relates to a natural type miRNA that inhibits gene expression, and use thereof.

BACKGROUND ART

MicroRNA (miRNA) is known as a nucleic acid molecule that inhibits gene expression and has been reported to inhibit transcription of a protein encoded by a gene via, for example, the following production process. That is, an miRNA transcription product (Pri-miRNA) having a cap structure on the 5'-terminus and poly(A) on the 3'-terminus is produced in the nucleus. The aforementioned Pri-miRNA is cleaved by RNase (Drosha) to produce a miRNA precursor (Pre-miRNA). The aforementioned Pre-miRNA forms a hairpin structure having a loop region and a stem region. The Pre-miRNA moves out from the nucleus and is degraded by RNase (Dicer) in the cytoplasm, and a double-stranded miRNA (mature miRNA) having 1-4 bases of overhang on the 3'-terminus is cleaved out. One of the strands of the double-stranded miRNA is called a guide strand and the other strand is called a passenger strand, and the aforementioned guide strand is bonded to a complex similar to RNA-induced Silencing Complex (RISC). This miRNA/RISC complex binds to the 3' untranslated region (3'UTR) of particular mRNA to inhibit translation of protein from the aforementioned mRNA.

It has been clarified that miRNA is deeply involved in life phenomena such as differentiation, cell proliferation, apoptosis and the like and many diseases such as viral infections, cancer and the like (patent document 1, non-patent document 1, non-patent document 2). Therefrom its application in, particularly, the medical field has been expected.

DOCUMENT LIST

Patent Document patent document 1: WO 2010/056737 A2

Non-Patent Documents non-patent document 1: Deiters, 2009, The AAPS Journal, 12, 51-60
non-patent document 2: Takeshita et al., 2010, Mol. Ther., 18, 181-187

SUMMARY OF THE INVENTION

Problems to be Solved by the Invention

For application of the aforementioned miRNA, for example, a method including use of a double-stranded mature miRNA or pre-miRNA, and the like are available. However, the former requires, before application, annealing of two single-stranded nucleic acid molecules, which produces a possibility of developing autoimmunity by TLR3 and the like that recognize the double strand. On the other hand, in the latter case, a large number of nucleotides makes the synthesis not easy, is disadvantageous in terms of cost, and also poses problems of intracellular transferability and pharmacokinetics.

Therefore, an object of the present invention is to provide a natural type miRNA which utilizes the structure of a mature miRNA.

In the present specification, "a natural type miRNA" means a single-stranded nucleic acid molecule comprising a guide strand and a passenger strand of a naturally occurring mature miRNA, and having the same quality of activity as a mature miRNA (i.e., activity of inhibiting the expression of target gene), and a part other than the guide strand and the passenger strand may contain an artificial constituent element.

Means of Solving the Problems

To achieve the aforementioned object, the natural type miRNA of the present invention is a single-stranded nucleic acid comprising X region and Y region, characterized in that the 3'-terminus of the aforementioned X region and the 5'-terminus of the aforementioned Y region are linked via a linker region of a non-nucleotide structure,
the aforementioned X region comprises (a) a guide strand sequence or (b) a passenger strand sequence of a mature miRNA,
when the X region comprises (a), the aforementioned Y region comprises a passenger strand sequence of the aforementioned mature miRNA,
when the X region comprises (b), the aforementioned Y region comprises a guide strand sequence of the aforementioned mature miRNA, and
the aforementioned guide strand sequence and the aforementioned passenger strand sequence form a double-stranded structure.

The composition of the present invention is a composition for inhibiting the expression of a gene, and characteristically contains the above-mentioned natural type miRNA of the present invention.

The composition of the present invention is a pharmaceutical composition which characteristically contains the above-mentioned natural type miRNA of the present invention.

The expression inhibitory method of the present invention is a method for inhibiting the expression of a target gene, which characteristically uses the above-mentioned natural type miRNA of the present invention.

The method of treating a disease of the present invention includes a step of administering the above-mentioned natural type miRNA of the present invention to a patient, wherein the aforementioned guide strand sequence in the above-mentioned natural type miRNA is a guide strand sequence of a mature miRNA that inhibits expression of genes involved in the aforementioned diseases.

Effect of the Invention

The natural type miRNA of the present invention can be synthesized easily at a low cost, and can inhibit translation of protein encoded by the aforementioned genes.

DESCRIPTION OF EMBODIMENTS

Figure 1:
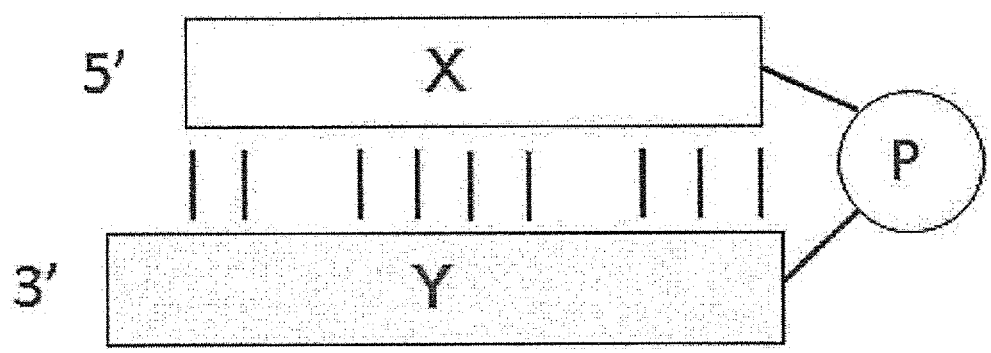
FIG. 1 is a schematic showing of one embodiment of the natural type miRNA of the present invention.

Unless otherwise specified, the terms used in the present specification mean what is generally meant by them in the art.

(1) Natural Type miRNA

The natural type miRNA of the present invention is, as mentioned above, a single-stranded nucleic acid comprising X region and Y region, characterized in that
the 3'-terminus of the aforementioned X region and the 5'-terminus of the aforementioned Y region are linked via a linker region of a non-nucleotide structure,
the aforementioned X region comprises (a) a guide strand sequence or (b) a passenger strand sequence of a mature miRNA,
when the X region comprises (a), the aforementioned Y region comprises a passenger strand sequence of the aforementioned mature miRNA,
when the X region comprises (b), the aforementioned Y region comprises a guide strand sequence of the aforementioned mature miRNA, and
the aforementioned guide strand sequence and the aforementioned passenger strand sequence form a double-stranded structure.

Whether the aforementioned X region contains (a) a guide strand sequence or (b) a passenger strand sequence is not necessarily limited. Preferably, a guide strand sequence and a passenger strand sequence are disposed in the same direction as the naturally occurring pre-miRNA (i.e., 5'→3' direction or 3'→5' direction). When the naturally occurring pre-miRNA is composed of guide strand-loop region-passenger strand in this order from the 5' direction, the natural type miRNA of the present invention preferably contains a guide strand sequence in the aforementioned X region. Conversely, when the naturally occurring pre-miRNA is composed of guide strand-loop region-passenger strand in this order from the 3' direction, the natural type miRNA of the present invention preferably contains a passenger strand sequence in the aforementioned X region.

In the below-mentioned Examples, miR-34a and let-7a preferably contain a guide strand sequence in the aforementioned X region, and miR-29b preferably contains a passenger strand sequence in the aforementioned X region.

The natural type miRNA of the present invention can inhibit, for example, expression of the target gene. Inhibition of expression means, for example, inhibition of the translation of the aforementioned target gene, that is, inhibition of the translation of a protein encoded by the aforementioned target gene, more particularly, inhibition of the translation of the aforementioned protein from mRNA of the aforementioned target gene. The aforementioned inhibition of the expression of the target gene can be verified by, for example, a decrease in the amount of a transcription product derived from the target gene; a decrease in the activity of the aforementioned transcription product; a decrease in the amount of a translation product generated from the aforementioned target gene; a decrease in the activity of the aforementioned translation product; or the like. The aforementioned proteins may be, for example, mature proteins, precursor proteins before being subjected to processing or post-translational modification.

Since the natural type miRNA of the present invention is a single-stranded nucleic acid molecule, annealing of two single strands is not necessary unlike mature miRNA, and can be produced at a low cost. Furthermore, since the natural type miRNA of the present invention is a single-stranded nucleic acid molecule, for example, it can avoid recognition by TLR3, RIG-I, MDA5 and the like involved in autoimmunity.

In the natural type miRNA of the present invention, a guide strand sequence and a passenger strand sequence are linked via a linker molecule of a non-nucleotide structure. Therefore, the miRNA can be synthesized easily and provided at a low cost, and is also superior in the pharmacokinetics and intracellular transferability, as compared to a single-stranded nucleic acid molecule comprising a pre-miRNA having a comparatively long nucleotide loop.

An outline of the configurational relationship between the aforementioned X region and the aforementioned Y region in the natural type miRNA of the present invention is shown in FIG. 1. FIG. 1 shows an outline and, for example, the length, shape and the like of each region are not limited. The natural type miRNA of the present invention has, as shown in FIG. 1, the aforementioned X region on the 5'-side and the aforementioned Y region on the 3'-side, and the 3'-terminus of the aforementioned X region and the 5'-terminus of the aforementioned Y region are linked via linker region (shown with "P" in the Figure) of a non-nucleotide structure.

In the natural type miRNA of the present invention, the aforementioned X region contains a guide strand sequence or a passenger strand sequence of any mature miRNA. When the aforementioned X region contains the aforementioned guide strand sequence, the aforementioned Y region contains a passenger strand sequence of the aforementioned mature miRNA, and when the aforementioned X region contains the aforementioned a passenger strand sequence, the aforementioned Y region contains a guide strand sequence of the aforementioned mature miRNA, wherein the aforementioned X region and the aforementioned Y region are intramolecularly annealed (also referred to as self-annealing) between the aforementioned guide strand sequence and the aforementioned passenger strand sequence. Accordingly, the natural type miRNA of the present invention forms a double-stranded structure in the aforementioned intramolecularly annealed region.

The natural type miRNA of the present invention is a linear single-stranded nucleic acid molecule, wherein the 5'-terminus thereof and the 3'-terminus thereof are unlinked. To maintain the unbinding of the both termini, the 5'-terminus of the natural type miRNA of the present invention is preferably, for example, a non-phosphate group.

In the natural type miRNA of the present invention, the aforementioned X region contains, as mentioned above, a guide strand sequence (a passenger strand sequence) of a mature miRNA. On the other hand, the aforementioned Y region contains a passenger strand sequence (a guide strand sequence) of the aforementioned mature miRNA. The guide strand sequence and a passenger strand sequence of a mature miRNA are, for example, registered in various databases (e.g., http://www.mirbase.org/etc.). Therefore, the aforementioned X region and the aforementioned Y region can be set based on, for example, the information of known mature miRNAs. The guide strand of the aforementioned mature miRNA is a strand, which is taken into an Argonaute (Ago) protein of RNA-induced silencing complex (RISC) and binds to mRNA of the target, and the passenger strand of the aforementioned mature miRNA is a strand complementary to the guide strand of the mature miRNA, and ultimately removed from the RISC. Generally, a guide strand and a passenger strand of a mature miRNA are not completely complementary, and each contains 1 to several unpaired bases.

In the following explanation, the aforementioned X region containing the aforementioned guide strand sequence is described in detail as an example. Those of ordinary skill in the art can readily understand, from the following description, the constitution of the natural type miRNA of the present invention in an embodiment wherein the aforementioned X region contains the aforementioned passenger strand sequence.

The aforementioned X region may consist solely of, for example, the aforementioned guide strand sequence, or may further have an additional sequence. In the latter case, the aforementioned X region consists of, for example, the aforementioned guide strand sequence and the aforementioned additional sequence, and the aforementioned additional sequence is linked to, for example, the 3'-terminus of the aforementioned guide strand sequence.

In the natural type miRNA of in the present invention, when the aforementioned guide strand sequence and the aforementioned passenger sequence are aligned and the 3'-terminus side of the guide strand has an overhang, the aforementioned Y region contains a sequence complementary to the sequence of the aforementioned overhang, at the 5'-terminus side of the aforementioned passenger strand. When the aforementioned X region contains an additional sequence and the aforementioned X region and the aforementioned Y region are aligned, the aforementioned Y region has a sequence complementary to the additional sequence of the aforementioned X region. When the additional sequence of the aforementioned X region is linked to the 3'-terminus of the aforementioned guide strand sequence, the aforementioned complementary sequence is linked to the 5'-terminus of the aforementioned passenger strand sequence. While the aforementioned complementary sequence may not be completely complementary as long as it can form a double-stranded structure continuous to a double strand of the aforementioned guide strand sequence and the aforementioned passenger sequence, it is desirably completely complementary. The aforementioned Y region may consist only of the aforementioned passenger sequence and a sequence complementary to the additional sequence of the aforementioned X region, and may further have an overhang unpaired with the aforementioned X region. That is, in the natural type miRNA of the present invention, when, for example, the aforementioned Y region and the aforementioned X region are aligned, the aforementioned Y region may have an overhang on the 3'-terminus. As use herein, the aforementioned overhang in the Y region is, for example, a terminus base that the aforementioned Y region has in excess than the aforementioned X region when the aforementioned Y region and the aforementioned X region are aligned. The length (O) of the overhang is, for example, as shown in the following formula.

length (O) of overhang=[full-length base number (Y) of Y region]−[full-length base number (X) of X region]

Since many mature miRNAs have an overhang unpaired with a guide strand, at the 3'-terminus of the passenger strand, further addition of an artificial overhang to the aforementioned 3'-terminus of the passenger strand is mostly unnecessary in the aforementioned Y region.

In the natural type miRNA of the present invention, the length of each region is not particularly limited. While examples of the conditions are shown below, the natural type miRNA of the present invention is not limited by such description. In the present invention, the numerical range of the base number discloses all positive integers that fall within the range and, for example, "1-4 bases" means all of "1, 2, 3, 4 bases" (hereinafter the same).

In the aforementioned X region, the length of the aforementioned guide strand sequence is not particularly limited and may be, for example, the length of a guide strand sequence of a reported mature miRNA. Specific examples thereof include a lower limit of 19 base length, 20 base length, and an upper limit of 25 base length, 24 base length, and ranges of 19-25 base length, 20-24 base length.

The length of the aforementioned additional sequence of the aforementioned X region is not particularly limited, and the lower limit is, for example, 0 base length, 1 base length, 2 base length, and the upper limit is, for example, 7 base length, 5 base length, 4 base length, 3 base length, and the range is, for example, 0-7 base length, 0-5 base length, 1-5 base length, 1-4 base length, 2-3 base length, 3-5 base length. The range of the length of the aforementioned additional sequence is preferably 3-7 base length, more preferably 3-5 base length.

The base sequence of the aforementioned additional sequence in the aforementioned X region is not particularly limited. When the length of the aforementioned additional sequence is 3 base length, for example, UAA, UGG, UCC, CAA, CGG, CCC and the like can be mentioned. When the length of the aforementioned additional sequence is 4 base length, for example, UAAU, UUAA, UUGG, UUUU and the like can be mentioned. When the length of the aforementioned additional sequence is 5 base length, for example, UAAUU, UCCGG, UUUUU, UUUUA, UUUAU, UUAUU, UAUUU, UUUAA, UUAUA, UAUUA, UUAAU, UAUAU, UUAAA, UAUAA, UAAUA, UAAAU, UAAAA, UUUGG, AUUAA, AUUUU, CUUAA, CUUUU, GUUAA, GUUUU and the like can be mentioned. When the length of the aforementioned additional sequence is 7 base length, for example, UAAUUAA, UCCGGCC and the like can be mentioned. The base sequence of the aforementioned additional sequence and the base sequence of the sequence complementary to the aforementioned additional sequence is preferably AU rich.

The length of the aforementioned X region is not particularly limited, the lower limit is, for example, 19 base length, 21 base length, 23 base length, the upper limit is, for example, 35 base length, 30 base length, 28 base length, 26 base length, and the range is, for example, 19-35 base length, 19-30 base length, 21-28 base length, 23-26 base length.

The length of the aforementioned overhang in the aforementioned Y region (when the aforementioned passenger strand itself has an overhang, the length includes the same) is not particularly limited, and the lower limit is, for example, 0 base length, 1 base length, and the upper limit is, for example, 4 base length, 3 base length, and the range is, for example, 0-4 base length, 1-3 base length, 2 base length.

The sequence of the aforementioned overhang is not particularly limited and is, for example, UU, CU, GC, UA, AA, CC, UG, CG, AU, TT and the like from the 3'-side. The aforementioned overhang can be imparted with resistance to ribonuclease by being, for example, TT.

The length of the aforementioned Y region is not particularly limited, and the lower limit is, for example, 19 base length, 21 base length, 23 base length, and the upper limit is, for example, 37 base length, 32 base length, 30 base length, 28 base length, and the range is, for example, 19-37 base length, 19-32 base length, 21-37 base length, 21-30 base length, 23-28 base length.

The full-length (T) of the natural type miRNA of the present invention is not particularly limited, and the lower limit is, for example, 38 base length, 42 base length, 46 base length, the upper limit is, for example, 72 base length, 62 base length, 58 base length, 54 base length, and the range is, for example, 38-72 base length, 40-68 base length, 38-62 base length, 42-58 base length, 46-54 base length.

In the natural type miRNA of the present invention, the kind of the aforementioned mature miRNA is not particularly limited, and can be appropriately selected according to the kind of the target gene.

Examples of the aforementioned mature miRNA include mature miRNAs such as hsa-miR-34a (miRBase Accession No. MI0000268), hsa-let-7a (miRBase Accession No. MI0000060), hsa-let-7f (miRBase Accession No. MI0000067), hsa-miR-150 (miRBase Accession No. MI0000479), hsa-miR-29b (miRBase Accession No. MI0000105) and the like.

hsa-miR-34a
(SEQ ID NO: 1/SEQ ID NO: 2)
UGGCAGUGUCUUAGCUGGUUGU/CAAUCAGCAAGUAUACUGCCCU hsa-let-7a
(SEQ ID NO: 3/SEQ ID NO: 4)
UGAGGUAGUAGGUUGUAUAGUU/CUAUACAAUCUACUGUCUUUC hsa-let-7f
(SEQ ID NO: 5/SEQ ID NO: 6)
UGAGGUAGUAGAUUGUAUAGUU/CUAUACAAUCUAUUGCCUUCCC hsa-miR-150
(SEQ ID NO: 7/SEQ ID NO: 8)
UCUCCCAACCCUUGUACCAGUG/CUGGUACAGGCCUGGGGGACAG hsa-miR-29b
(SEQ ID NO: 10/SEQ ID NO: 9)
GCUGGUUUCAUAUGGUGGUUUAGA/UAGCACCAUUUGAAAUCAGUGUU Here, each nucleotide sequence is described in the 5'→3' direction in the order of guide strand sequence/passenger sequence (passenger strand sequence/guide strand sequence only for hsa-miR-29b).

The guide strand of miR-34a targets, for example, AXL, MET, CDK4, CDK6, SIRT1, CCND1, SIRT1, BCL-2 and the like, and the inhibition of the expression of these target genes can prevent or treat diseases such as lung cancer, colorectal cancer, gastric cancer, liver cancer, breast cancer and the like.

The guide strand of let-7a targets, for example, HMGA2 (high mobility group AT-hook 2), KRAS, NRAS, HRAS, MYC, TLR4 and the like, and the inhibition of the expression of these target genes can prevent or treat diseases such as lung cancer, colorectal cancer, gastric cancer, liver cancer, breast cancer and the like.

The guide strand of let-7f targets, for example, HMGA2 (high mobility group AT-hook 2), KRAS, NRAS, HRAS, MYC, TLR4 and the like, and the inhibition of the expression of these target genes can prevent or treat diseases such as lung cancer, colorectal cancer, gastric cancer, liver cancer, breast cancer and the like.

The guide strand of miR-150 targets, for example, COL1A1, COL4A4, SMAD2, SP1 and the like, and the inhibition of the expression of these target genes can prevent or treat diseases such as lung fibrosis, hepatic fibrosis and the like.

The guide strand of miR-29b targets, for example, COL1A1, MCL1, DNMT3A, DNMT3B, TCL1A, TGFb3 and the like, and the inhibition of the expression of these target genes can prevent or treat diseases such as lung cancer, colorectal cancer, gastric cancer, liver cancer, breast cancer, lung fibrosis, hepatic fibrosis and the like.

The constitution units of the natural type miRNA of the present invention are not particularly limited. Examples thereof include nucleotide residues. Examples of the aforementioned nucleotide residues include a ribonucleotide residue and a deoxyribonucleotide residue. In the natural type miRNA of the present invention, the aforementioned nucleotide residue is preferably, for example, a ribonucleotide residue. The aforementioned nucleotide residue may be, for example, the one that is not modified (unmodified nucleotide residue) or the one that has been modified (modified nucleotide residue). By configuring the natural type miRNA of the present invention to include the aforementioned modified nucleotide residue, for example, the resistance of the natural type miRNA to nuclease can be improved, thereby allowing the stability of the natural type miRNA to be improved. Furthermore, the natural type miRNA of the present invention further may include, for example, a non-nucleotide residue in addition to the aforementioned nucleotide residue.

When the natural type miRNA includes, for example, the aforementioned modified ribonucleotide residue(s) in addition to the aforementioned unmodified ribonucleotide residues, the number of the aforementioned modified ribonucleotide residue(s) is not particularly limited, and is, for example, "one to several", specifically, for example, 1 to 5, preferably 1 to 4, more preferably 1 to 3, and most preferably 1 or 2. The aforementioned modified ribonucleotide residue as contrasted to the aforementioned unmodified ribonucleotide residue may be, for example, the aforementioned deoxyribonucleotide residue obtained by substituting a ribose residue with a deoxyribose residue. When the natural type miRNA of the present invention includes, for example, the aforementioned deoxyribonucleotide residue (s) in addition to the aforementioned unmodified ribonucleotide residue(s), the number of the aforementioned deoxyribonucleotide residue(s) is not particularly limited, and is, for example, "one to several", specifically, for example, 1 to 5, preferably 1 to 4, more preferably 1 to 3, and most preferably 1 or 2.

The aforementioned nucleotide residue includes, for example, a sugar, a base, and a phosphate as its components. The aforementioned ribonucleotide residue has, for example, a ribose residue as the sugar; and adenine (A), guanine (G), cytosine (C), or uracil (U) as the base. The aforementioned deoxyribose residue has, for example, a deoxyribose residue as the sugar; and adenine (A), guanine (G), cytosine (C), or thymine (T) as the base.

The aforementioned components of the aforementioned unmodified nucleotide residue are the same or substantially the same as, for example, the components of a naturally-occurring nucleotide residue. Specifically, for example, the components are the same or substantially the same as the components of a nucleotide residue occurring naturally in a human body.

For example, the aforementioned modified nucleotide residue may be such that any of the components of the aforementioned unmodified nucleotide residue is modified. Examples of the aforementioned modified nucleotide residue include naturally-occurring nucleotide residues and artificially-modified nucleotide residues.

The aforementioned modified nucleotide residue may be, for example, a residue of an alternative of the aforementioned nucleotide. Examples of the aforementioned alternative include artificial nucleic acid monomer residues. Specific examples thereof include PNA (Peptide Nucleic Acid), LNA (Locked Nucleic Acid), and ENA (2'-O,4'-C-Ethylenebridged Nucleic Acids).

In the aforementioned nucleotide residue, the aforementioned base is not particularly limited. The aforementioned base may be, for example, a natural base or a non-natural base. The aforementioned base may be, for example, a naturally-derived base or a synthetic base. As the aforementioned base, for example, a common base, a modified analog thereof, and the like can be used.

In the natural type miRNA of the present invention, the linker region of the aforementioned non-nucleotide structure preferably contains at least one selected from the group consisting of an amino acid residue, a polyamine residue and a polycarboxylic acid residue. The aforementioned linker region may or may not contain a residue other than the amino acid residue, polyamine residue and polycarboxylic acid residue. For example, the aforementioned linker region may contain any of a polycarboxylic acid residue, a terephthalic acid residue and an amino acid residue.

In the present invention, the "polyamine" means any compound containing a plurality of (two, three or more) amino groups. The aforementioned "amino group" is not limited to an —NH$_2$ group and also includes an imino group (—NH—). In the present invention, the aforementioned polyamine is not particularly limited, and examples thereof include 1,4-diaminobenzene, 1,3-diaminobenzene, 1,2-diaminobenzene and the like. In the present invention, moreover, the "polycarboxylic acid" means any compound containing a plurality of (two, three or more) carboxy groups. In the present invention, the aforementioned polycarboxylic acid is not particularly limited, and examples thereof include 1,4-dicarboxybenzene (terephthalic acid), 1,3-dicarboxybenzene (isophthalic acid), 1,2-dicarboxybenzene (phthalic acid) and the like. In the present invention, moreover, the "amino acid" means any organic compound containing one or more amino groups and one or more carboxy groups in a molecule, as mentioned below. The aforementioned "amino group" is not limited to an —NH$_2$ group and also includes an imino group (—NH—).

In the natural type miRNA of the present invention, the aforementioned amino acid residue may be composed of a plurality of interlinked amino acid residues. In the present invention, the amino acid residue that is a plurality of interlinked amino acid residues is, for example, a residue containing a peptide structure. More specifically, the aforementioned amino acid residue that is a plurality of interlinked amino acid residues is, for example, an amino acid residue of the below-mentioned chemical formula (I) wherein the below-mentioned chemical formula (Ia) is a peptide (e.g., glycine dimer or glycine trimer etc.).

In the natural type miRNA of the present invention, the aforementioned amino acid residue may be a glycine residue, a terephthalic acid amide residue, a proline residue or a lysine residue. The aforementioned amino acid residue may be a modified amino acid residue or an amino acid derivative.

In the natural type miRNA of the present invention, the aforementioned linker region is represented by, for example, the following chemical formula (I-0).

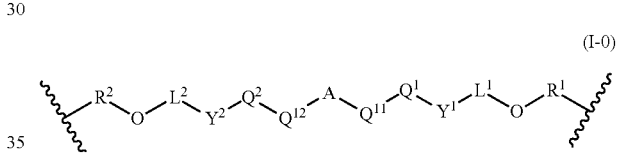

(I-0)

in the aforementioned chemical formula (I-0), $Q^{11}$ and $Q^{12}$ are each independently a single bond, CH$_2$ (a methylene group), NH (an imino group), C=O (a carbonyl group), C=S (a thiocarbonyl group), C=NH (an iminomethylene group), O, or S, $Q^1$ and $Q^2$ are each independently a single bond, CH$_2$ (a methylene group), NH (an imino group), C=O (a carbonyl group), C=S (a thiocarbonyl group), C=NH (an iminomethylene group), O, or S, $Y^1$ and $Y^2$ are each independently a single bond, CH$_2$, NH, O, or S;

$L^1$ is an alkylene chain having n carbon atoms, and a hydrogen atom on an alkylene carbon atom may or may not be substituted with OH, OR$^a$, NH$_2$, NHR$^a$, NR$^a$R$^b$, SH, or SR$^a$, or, $L^1$ is a polyether chain obtained by substituting at least one carbon atom on the aforementioned alkylene chain with an oxygen atom, provided that: when $Y^1$ is NH, O, or S, an atom bound to $Y^1$ in $L^1$ is carbon, an atom bound to OR$^1$ in $L^1$ is carbon, and oxygen atoms are not adjacent to each other;

$L^2$ is an alkylene chain having m carbon atoms, and a hydrogen atom on an alkylene carbon atom may or may not be substituted with OH, OR$^c$, NH$_2$, NHR$^c$, NR$^c$R$^d$, SH, or SR$^c$, or $L^2$ is a polyether chain obtained by substituting at least one carbon atom on the aforementioned alkylene chain with an oxygen atom, provided that: when $Y^2$ is NH, O, or S, an atom bound to $Y^2$ in $L^2$ is carbon, an atom bound to OR$^2$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

the aforementioned regions X and Y are each linked to the aforementioned linker residue via —$OR^1$— or —$OR^2$—, wherein $R^1$ and $R^2$ may or may not be present, and when they are present, $R^1$ and $R^2$ are each independently a nucleotide residue or the aforementioned structure (I-0); and A is any atomic group.

The combination of the aforementioned regions (X) and (Y) with —$OR^1$— and —$OR^2$— is not particularly limited, and may be, for example, any of the following conditions.

Condition (1):

the aforementioned regions (X) and (Y) are linked to the structure of the aforementioned formula (I) via —$OR^2$— and —$OR^1$—, respectively.

Condition (2):

the aforementioned regions (X) and (Y) are linked to the structure of the aforementioned formula (I) via —$OR^1$— and —$OR^2$—, respectively.

In the aforementioned chemical formula (I-0), for example, $Q^{11}$ may be C=O (a carbonyl group), and $Q^1$ may be NH (an imino group). In addition, for example, $Q^{11}$ may be NH (an imino group), and $Q^1$ may be C=O (a carbonyl group). Furthermore, for example, $Q^{12}$ may be C=O (a carbonyl group), and $Q^2$ may be NH (an imino group). Moreover, for example, $Q^{12}$ may be NH (an imino group), and $Q^2$ may be C=O (a carbonyl group).

In the aforementioned chemical formula (I-0), each of $Q^{11}$ and $Q^{12}$ may be, for example, a carbonyl group. In this case, each of $Q^1$ and $Q^2$ is preferably an imino group. In addition, in this case, the structure of the following chemical formula (Iα) is more preferably represented by the following chemical formula (Iα2).

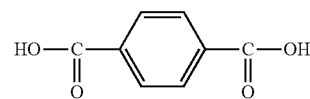

(Iα)

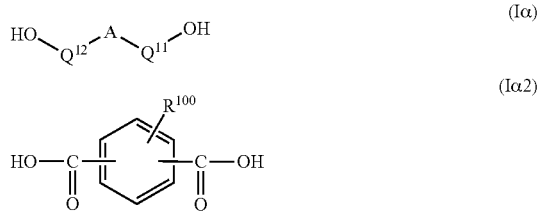

(Iα2)

In the aforementioned chemical formula (Iα2), $R^{100}$ is any substituent, which may or may not be present. When it is present, it may be present singly or in plurality. When it is present in plurality, they may be the same or different from each other. Examples of the aforementioned any substituent for $R^{100}$ include the below-mentioned substituents exemplified as the aforementioned $R^a$, $R^b$, $R^c$ and $R^d$. More specific examples thereof include halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl and the like. The structure of the aforementioned chemical formula (Iα2) is more preferably represented by the following chemical formula (Iα3).

(Iα3)

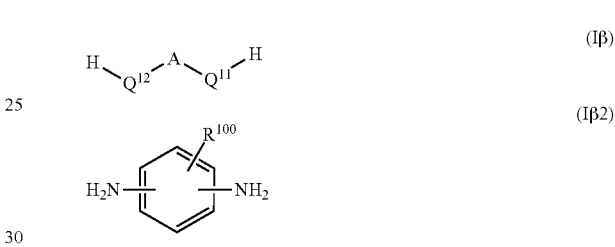

When $Q^{11}$ and $Q^{12}$ are carbonyl groups, and $Q^1$ and $Q^2$ are imino groups, the linker residue of the aforementioned chemical formula (I-0) can be a carboxylic acid amide residue or a carboxylic acid residue. For example, the "TPA" structure in the below-mentioned Example can be a terephthalamide residue or a terephthalic acid residue represented by the aforementioned chemical formula (Iα3).

In the aforementioned chemical formula (I-0), each of $Q^{11}$ and $Q^{12}$ may be an imino group. In this case, each of $Q^1$ and $Q^2$ is preferably a carbonyl group. In this case, the structure of the following chemical formula (Iβ) is more preferably represented by the following chemical formula (Iβ2).

(Iβ)

(Iβ2)

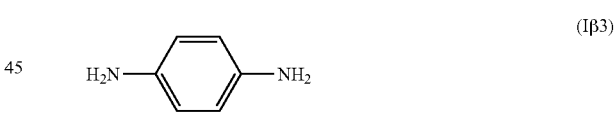

In the aforementioned chemical formula (Iβ2), $R^{100}$ is any substituent, which may or may not be present. When it is present, it may be present singly or in plurality. When it is present in plurality, they may be the same or different from each other. Specifically, for example, it is the same as $R^{100}$ in the aforementioned chemical formula (Iα2). In addition, the structure of the aforementioned chemical formula (Iβ2) is more preferably represented by the following chemical formula (Iβ3).

(Iβ3)

In the natural type miRNA of the present invention, when the aforementioned linker residue is an amino acid residue, the aforementioned amino acid residue is represented by, for example, the following chemical formula (I). The structure of the following chemical formula (I) is one example of the structure represented by the aforementioned chemical formula (I-0).

(I)

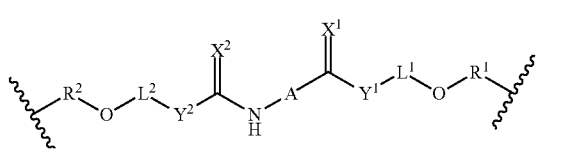

In the aforementioned formula (I), for example, $X^1$, $X^2$, $Y^1$, $Y^2$, $L^1$ and $L^2$ are as defined above.

The sequence complementary to the sequence of the aforementioned microRNA is each bound to the aforementioned amino acid residue via —$OR^1$— or —$OR^2$—, wherein $R^1$ and $R^2$ may or may not be present, and when they are present, $R^1$ and $R^2$ are each independently a nucleotide residue or the aforementioned structure (I); and
A is any atomic group, provided that the following chemical formula (Ia) is an amino acid or peptide.

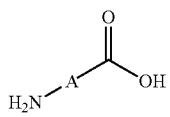

(Ia)

The atomic group A in the aforementioned chemical formula (I), (Iα) or (Ia) may or may not contain, for example, at least one selected from the group consisting of chain atomic group, alicyclic atomic group, aromatic atomic group, heteroaromatic atomic group, and heteroalicyclic atomic group. While the aforementioned chain atomic group is not particularly limited, for example, alkyl, alkenyl, alkynyl, haloalkyl, hydroxyalkyl, alkoxyalkyl, aminoalkyl, silyl, silyloxyalkyl and the like can be mentioned. While the aforementioned alicyclic atomic group is not particularly limited, for example, cycloalkyl, cycloalkenyl, cycloalkylalkyl, cyclylalkyl and the like can be mentioned. While the aforementioned aromatic atomic group is not particularly limited, for example, aryl, arylalkyl, alkylaryl, condensed-ring aryl, condensed-ring arylalkyl, condensed-ring alkylaryl and the like can be mentioned. The aforementioned heteroaromatic atomic group is not particularly limited, and examples thereof include heteroaryl, heteroarylalkyl, alkylheteroaryl, condensed-ring heteroaryl, condensed-ring heteroarylalkyl, condensed-ring alkylheteroaryl and the like. In the atomic group A in the aforementioned chemical formula (I), (Iα) or (Ia), each of the aforementioned atomic groups may or may not further have a substituent or a protecting group. When the aforementioned substituent or protecting group is in plurality, they may be the same or different. The aforementioned substituents are, for example, those exemplified for the aforementioned $R^a$, $R^b$, $R^c$ and $R^d$, more specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. The aforementioned protecting groups are, for example, the same as those exemplified for the aforementioned $R^a$, $R^b$, $R^c$ and $R^d$.

In the present invention, the "amino acid" refers to, as mentioned above, any organic compound containing at least one amino group and at least one carboxy group in a molecule. The aforementioned "amino group" is not limited to —$NH_2$ group, and also includes imino group (—NH—). For example, proline, hydroxyproline and the like not containing —$NH_2$ group in a molecule but containing imino group (—NH—) is included in the definition of the "amino acid" in the present invention. In the present invention, the aforementioned "amino acid" may be, as mentioned below, a natural amino acid or an artificial amino acid. For example, since a compound represented by the below-mentioned chemical formula (Ia2) or (Ia3) contains an amino group and a carboxy group in a molecule, it is encompassed in the definition of the "amino acid" in the present invention.

Therefore, for example, the aforementioned chemical formula (I) wherein the atomic group A is a structure shown by the below-mentioned chemical formula (A2) or chemical formula (A2a) is included in the definition of "amino acid residue" in the present invention. For example, the "TPA" structure in the below-mentioned Example is also included in the definition of the "amino acid residue" in the present invention. The "peptide" in the present invention refers to an organic compound having a structure wherein not less than 2 molecules of amino acid are bonded via a peptide bond. The aforementioned peptide bond may be an acid amide structure or an acid imide structure. When plural amino groups are present in the amino acid or peptide molecule represented by the aforementioned chemical formula (Ia), the amino group clearly shown in the aforementioned chemical formula (Ia) may be any amino group. In addition, when plural carboxy groups are present in the amino acid or peptide molecule represented by the aforementioned chemical formula (Ia), the carboxy group clearly shown in the aforementioned chemical formula (Ia) may be any carboxy group.

In the aforementioned amino acid residue of the natural type miRNA of the present invention, the aforementioned amino acid may be, as mentioned above, natural amino acid or artificial amino acid. In the present invention, the "natural amino acid" refers to an amino acid having a naturally-occurring structure or an optical isomer thereof. The production method of the aforementioned natural amino acid is not particularly limited and, for example, it may be extracted from the nature, or may be synthesized. In the present invention, moreover, the "artificial amino acid" refers to an amino acid having a structure not occurring naturally. That is, the aforementioned artificial amino acid is an amino acid, i.e., a carboxylic acid derivative containing an amino group (organic compound containing at least one amino group and at least one carboxy group in a molecule) and having a structure not occurring naturally. The aforementioned artificial amino acid preferably does not contain, for example, a heterocycle. The aforementioned amino acid may be an amino acid constituting, for example, a protein. The aforementioned amino acid may be, for example, at least one kind selected from the group consisting of glycine, α-alanine, arginine, asparagine, aspartic acid, cysteine, cystine, glutamine, glutamic acid, histidine, isoleucine, leucine, lysine, hydroxylysine, methionine, phenylalanine, serine, threonine, tyrosine, valine, proline, 4-hydroxyproline, tryptophan, β-alanine, 1-amino-2-carboxycyclopentane, aminobenzoic acid, aminopyridinecarboxylic acid and amino acid represented by the following chemical formula (Ia2), and may or may not further have a substituent or a protecting group. Examples of the aforementioned substituent include the substituents exemplified for the aforementioned $R^a$, $R^b$, $R^c$ and $R^d$. More specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like can be mentioned. The aforementioned protecting group is the same as, for example, the protecting groups exemplified for the aforementioned $R^a$, $R^b$, $R^c$ and $R^d$. When the amino acid of the aforementioned chemical formula (Ia), which is not peptide, contains isomers such as optical isomer, geometric isomer, stereoisomer and the like, any isomer can be used.

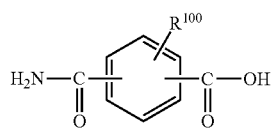
(Ia2)

In the aforementioned chemical formula (Ia2), $R^{100}$ is an optional substituent and may or may not be present. When it is present, the number thereof may be one or more and, when it is present in plurality, they may be the same or different. Examples of the aforementioned optional substituent for $R^{100}$ include the substituents exemplified for the aforementioned $R^a$, $R^b$, $R^c$ and $R^d$, more specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. The structure of the aforementioned chemical formula (Ia2) may be, for example, the following chemical formula (Ia3).

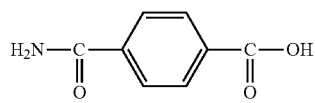
(Ia3)

When the structure of the aforementioned chemical formula (Ia) is the aforementioned chemical formula (Ia2), the structure of the atomic group A in the aforementioned chemical formula (I) is represented by the following chemical formula (A2). $R^{100}$ in the following chemical formula (A2) is the same as that in the aforementioned chemical formula (Ia2). When the structure of the aforementioned chemical formula (Ia) is the aforementioned chemical formula (Ia3), the structure of the atomic group A in the aforementioned chemical formula (I) is represented by the following chemical formula (A2a).

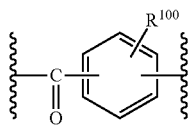
(A2)

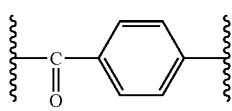
(A2a)

The structure of the aforementioned chemical formula (I) is, for example, the following chemical formulae (I-1)-(I-7), wherein n and m are the same as those in the aforementioned chemical formula (I).

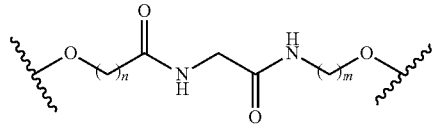
(I-1)

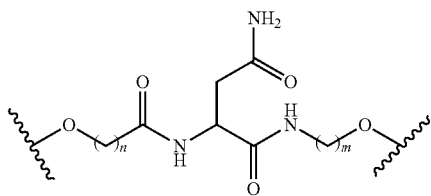
(I-2)

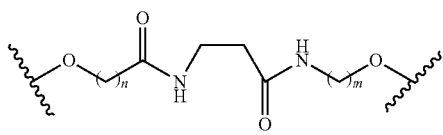
(I-3)

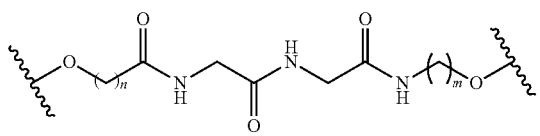
(I-4)

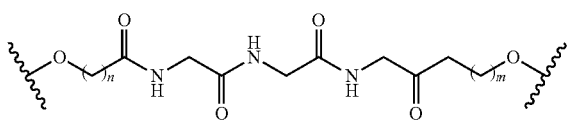
(I-5)

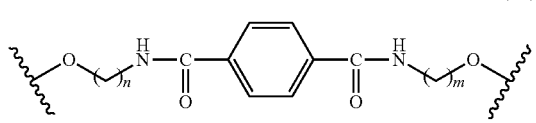
(I-6)

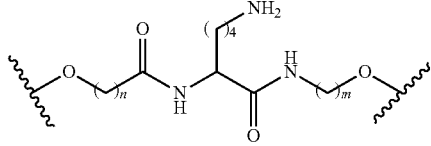
(I-7)

In the aforementioned chemical formulae (I-1)-(I-7), n and m are not particularly limited, and as described above. Specific examples thereof include n=11 and m=12 or n=5 and m=4 in the aforementioned chemical formula (I-1), n=5 and m=4 in the aforementioned chemical formula (I-4), n=4 and m=4 in the aforementioned chemical formula (I-6), and n=5 and m=4 in the aforementioned chemical formula (1-7). The structures thereof are shown in the following chemical formulae (I-1a), (I-1b), (I-4a), (I-6a) and (I-7a).

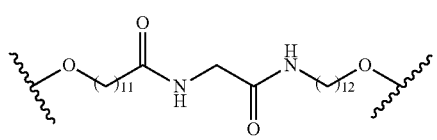
(I-1a)

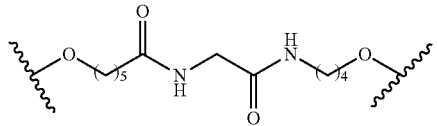
(I-1b)

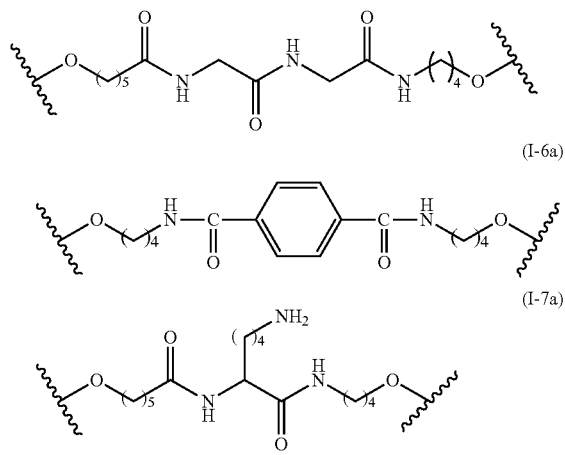

In the natural type miRNA of the present invention, the aforementioned linker region is represented, for example, by the following formula (II):

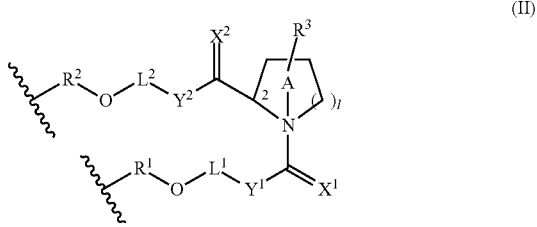

In the aforementioned formula (II), for example,
$X^1$ and $X^2$ are each independently $H_2$, O, S, or NH;
$Y^1$ and $Y^2$ are each independently a single bond, $CH_2$, NH, O, or S;
$R^3$ is a hydrogen atom or a substituent which is bonded to C-3, C-4, C-5 or C-6 on ring A,
$L^1$ is an alkylene chain having n atoms, and a hydrogen atom on an alkylene carbon atom may or may not be substituted with OH, $OR^a$, $NH_2$, $NHR^a$, $NR^aR^b$, SH, or $SR^a$, or,
$L^1$ is a polyether chain obtained by substituting at least one carbon atom on the aforementioned alkylene chain with an oxygen atom,
provided that: when $Y^1$ is NH, O, or S, an atom bound to $Y^1$ in $L^1$ is carbon, an atom bound to $OR^1$ in $L^1$ is carbon, and oxygen atoms are not adjacent to each other;
$L^2$ is an alkylene chain having m atoms, and a hydrogen atom on an alkylene carbon atom may or may not be substituted with OH, $OR^c$, $NH_2$, $NHR^c$, $NR^cR^d$, SH, or $SR^c$, or
$L^2$ is a polyether chain obtained by substituting at least one carbon atom on the aforementioned alkylene chain with an oxygen atom,
provided that: when $Y^2$ is NH, O, or S, an atom bound to $Y^2$ in $L^2$ is carbon, an atom bound to $OR^2$ in $L^2$ is carbon, and oxygen atoms are not adjacent to each other;
$R^a$, $R^b$, $R^c$, and $R^d$ are each independently a substituent or a protecting group;
l is 1 or 2;
m is an integer in the range from 0 to 30; and
n is an integer in the range from 0 to 30; and in ring A, one carbon atom other than the aforementioned C-2 on the ring A may be substituted by nitrogen, oxygen or sulfur, and may contain, in the aforementioned ring A, a carbon-carbon double bond or a carbon-nitrogen double bond,
the aforementioned regions (X) and (Y) are each linked to the aforementioned non-nucleotide structure via $—OR^1—$ or $—OR^2—$,
wherein $R^1$ and $R^2$ may or may not be present, and when they are present, $R^1$ and $R^2$ are each independently a nucleotide residue or the aforementioned structure (II).

In the aforementioned formula (II), for example, $X^1$ and $X^2$ are each independently $H_2$, O, S, or NH. In the aforementioned formula (II), "$X^1$ is $H_2$" means that $X^1$ forms $CH_2$ (a methylene group) together with a carbon atom to which $X^1$ binds. The same applies to $X^2$.

In the aforementioned formula (II), $Y^1$ and $Y^2$ are each independently a single bond, $CH_2$, NH, O, or S.

In the aforementioned formula (II), l in ring A is 1 or 2. When l=1, ring A is a 5-membered ring, for example, the aforementioned pyrrolidine skeleton. The aforementioned pyrrolidine skeleton is, for example, proline skeleton, prolinol skeleton or the like, and exemplified by the divalent structures thereof. When l=2, ring A is a 6-membered ring, for example, the aforementioned piperidine skeleton. In ring A, one carbon atom other than C-2 on ring A may be substituted by nitrogen, oxygen or sulfur. Ring A may contain, in ring A, a carbon-carbon double bond or a carbon-nitrogen double bond. Ring A is, for example, L type or D type.

In the aforementioned formula (II), $R^3$ is a hydrogen atom or substituent bonded to C-3, C-4, C-5 or C-6 on ring A. When $R^3$ is the aforementioned substituent, substituent $R^3$ may be one or more, or may be absent. When $R^3$ is present in plurality, they may be the same or different.

The substituent $R^3$ is, for example, halogen, OH, $OR^4$, $NH_2$, $NHR^4$, $NR^4R^5$, SH, $SR^4$, oxo group (=O) and the like.

$R^4$ and $R^5$ are, for example, each independently a substituent or a protecting group, and may be the same or different. Examples of the aforementioned substituent include halogen, alkyl, alkenyl, alkynyl, haloalkyl, aryl, heteroaryl, arylalkyl, cycloalkyl, cycloalkenyl, cycloalkylalkyl, cyclylalkyl, hydroxyalkyl, alkoxyalkyl, aminoalkyl, heterocyclylalkenyl, heterocyclylalkyl, heteroarylalkyl, silyl, silyloxyalkyl and the like. The same applies hereinafter. The substituent $R^3$ may be selected from the substituents recited above.

The aforementioned protecting group is a functional group that inactivates, for example, a highly-reactive functional group. Examples of the protecting group include known protecting groups and the like. Regarding the aforementioned protecting group, for example, the description in the literature (J. F. W. McOmie, "Protecting Groups in Organic Chemistry", Prenum Press, London and New York, 1973) can be incorporated herein. The aforementioned protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), a dimethoxytrityl group (DMTr) and the like. When $R^3$ is $OR^4$, the aforementioned protecting group is not particularly limited, and examples thereof include a TBDMS group, an ACE group, a TOM group, a CEE group, a CEM group, a TEM group and the like. Other examples of the protecting group include silyl-containing groups. The same applies hereinafter.

In the aforementioned formula (II), $L^1$ is an alkylene chain having n atoms. A hydrogen atom(s) on the aforementioned alkylene carbon atom(s) may or may not be substituted with, for example, OH, $OR^a$, $NH_2$, $NHR^a$, $NR^aR^b$, SH, or $SR^a$. Alternatively, $L^1$ may be a polyether chain obtained by substituting at least one carbon atom on the aforementioned alkylene chain with an oxygen atom. The aforementioned polyether chain is, for example, polyethylene glycol. When $Y^1$ is NH, O, or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the aforementioned formula (II), $L^2$ is an alkylene chain having m atoms. A hydrogen atom(s) on the aforementioned alkylene carbon atom(s) may or may not be substituted with, for example, OH, $OR^c$, $NH_2$, $NHR^c$, $NR^cR^d$, SH, or $SR^c$. Alternatively, $L^2$ may be a polyether chain obtained by substituting at least one carbon atom on the aforementioned alkylene chain with an oxygen atom. When $Y^2$ is NH, O, or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent to each other.

n of $L^1$ and m of $L^2$ are not particularly limited, and the lower limit of each of them may be 0, for example, and the upper limit of the same is not particularly limited. For example, n and m can be set as appropriate depending on a desired length of the aforementioned non-nucleotide structure. For example, from the view point of manufacturing cost, yield, and the like, n and m are each preferably 0 to 30, more preferably 0 to 20, and still more preferably 0 to 15. n and m may be the same (n=m) or different. n+m is, for example, 0 to 30, preferably 0 to 20, and more preferably 0 to 15.

For example, $R^a$, $R^b$, $R^c$ and $R^d$ are each independently a substituent or a protecting group. Examples of the aforementioned substituent and the aforementioned protecting group are the same as above.

In the aforementioned formula (II), each hydrogen atom may be independently substituted with, for example, a halogen such as Cl, Br, F, I and the like.

The aforementioned X region and the aforementioned Y region are each bound to the aforementioned non-nucleotide structure via, for example, —$OR^1$— or —$OR^2$—. Here, $R^1$ and $R^2$ may or may not be present. When $R^1$ and $R^2$ are present, $R^1$ and $R^2$ are each independently a nucleotide residue or the structure represented by the aforementioned formula (II). When $R^1$ and/or $R^2$ are/is the aforementioned nucleotide residue, the aforementioned non-nucleotide structure is formed by, for example, the aforementioned non-nucleotide residue having the structure of the aforementioned formula (II) excluding the nucleotide residue $R^1$ and/or $R^2$, and the aforementioned nucleotide residue(s). When $R^1$ and/or $R^2$ are/is the structure represented by the aforementioned formula (II), the structure of the aforementioned non-nucleotide structure is such that, for example, two or more of the aforementioned non-nucleotide residues having the structure of the aforementioned formula (II) are linked to each other. The number of the structures of the aforementioned formula (II) may be, for example, 1, 2, 3, or 4. When the aforementioned structure includes a plurality of the aforementioned structures, the structures of the aforementioned (II) may be linked, for example, either directly or via the aforementioned nucleotide residue(s). On the other hand, when $R^1$ and $R^2$ are not present, the aforementioned non-nucleotide structure is formed by, for example, the aforementioned non-nucleotide residue having the structure of the aforementioned formula (II) alone.

The combination of the aforementioned regions X and Y with —$OR^1$— and —$OR^2$— is not particularly limited, and may be, for example, any of the following conditions:

Conditions (1)
the aforementioned regions X and Y are linked to the structure of the aforementioned formula (II) via —$OR^2$— and —$OR^1$—, respectively;

Conditions (2)
the aforementioned regions X and Y are linked to the structure of the aforementioned formula (II) via —$OR^1$— and —$OR^2$—, respectively;

Examples of the structure of the aforementioned formula (II) include the structures of the following formulae (II-1) to (II-9). In the following formulae, n and m are the same as in the aforementioned formula (II). In the following formulae, q is an integer of 0-10.

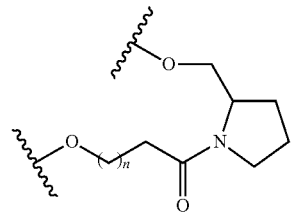

(II-1)

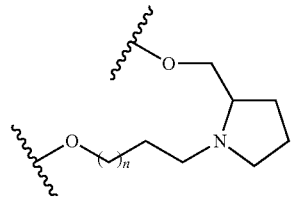

(II-2)

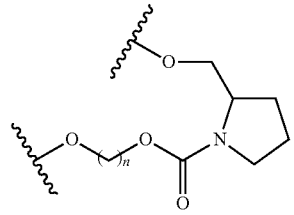

(II-3)

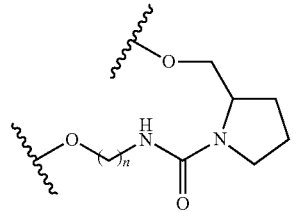

(II-4)

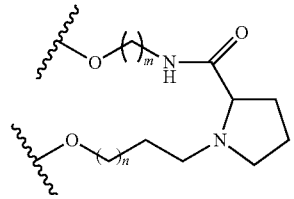

(II-5)

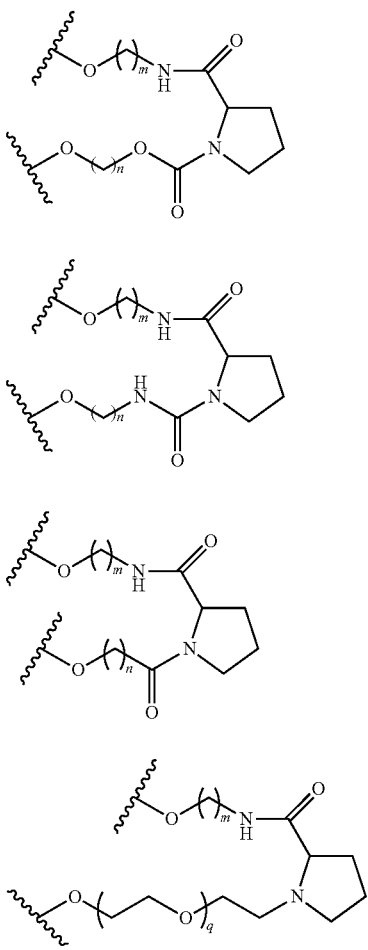

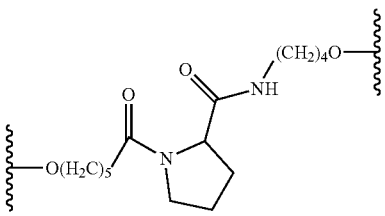

In the aforementioned formulae (II-1) to (II-9), n, m and q are not particularly limited, and are as described above. Specific example thereof is the aforementioned formula (II-1) wherein n=8, the aforementioned (II-2) wherein n=3, the aforementioned formula (II-3) wherein n=4 or 8, the aforementioned (II-4) wherein n=7 or 8, the aforementioned formula (II-5) wherein n=3 and m=4, the aforementioned (II-6) wherein n=8 and m=4, the aforementioned formula (II-7) wherein n=8 and m=4, the aforementioned (II-8) wherein n=5 and m=4, and the aforementioned formula (II-9) wherein q=1 and m=4. One embodiment (n=8) of the aforementioned formula (II-4) is shown in the following formula (II-4a), and one embodiment (n=5, m=4) of the aforementioned formula (II-8) is shown in the following formula (II-8a).

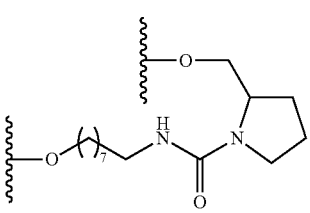

In the present invention, the term "alkyl" encompasses, for example, straight-chain and branched alkyl groups. The number of carbon atoms in the aforementioned alkyl is not particularly limited, and is, for example, 1 to 30, preferably 1 to 6, more preferably 1 to 4. Examples of the aforementioned alkyl group include: methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, and n-decyl and the like. Among them, for example, methyl, ethyl, n-propyl, isopropyl, n-butyl, isobutyl, sec-butyl, tert-butyl, n-pentyl, isopentyl, neopentyl, n-hexyl, isohexyl, and the like are preferable.

In the present invention, the term "alkenyl" encompasses, for example, straight-chain and branched alkenyls. Examples of the aforementioned alkenyl include the aforementioned alkyls having one or more double bonds and the like. The number of carbon atoms in the aforementioned alkenyl is not particularly limited, and is, for example, the same as that in the aforementioned alkyl, preferably 2 to 8. Examples of the aforementioned alkenyl include vinyl, 1-propenyl, 2-propenyl, 1-butenyl, 2-butenyl, 3-butenyl, 1,3-butadienyl, 3-methyl-2-butenyl and the like.

In the present invention, the term "alkynyl" encompasses, for example, straight-chain and branched alkynyls. Examples of the aforementioned alkynyl include the aforementioned alkyls having one or more triple bonds and the like. The number of carbon atoms in the aforementioned alkynyl is not particularly limited, and is, for example, the same as that in the aforementioned alkyl, preferably 2 to 8. Examples of the aforementioned alkynyl include ethynyl, propynyl, butynyl and the like. The aforementioned alkynyl may further include, for example, one or more double bonds.

In the present invention, the term "aryl" encompasses, for example, monocyclic aromatic hydrocarbon groups and polycyclic aromatic hydrocarbon groups. Examples of the aforementioned monocyclic aromatic hydrocarbon group include phenyl and the like. Examples of the aforementioned polycyclic aromatic hydrocarbon group include 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl and the like. Among them, for example, phenyl, naphthyls such as 1-naphthyl and 2-naphthyl, and the like are preferable.

In the present invention, the term "heteroaryl" encompasses, for example, monocyclic aromatic heterocyclic groups and condensed aromatic heterocyclic groups. Examples of the aforementioned heteroaryl include furyls (e.g., 2-furyl, 3-furyl), thienyls (e.g., 2-thienyl, 3-thienyl), pyrrolyls (e.g., 1-pyrrolyl, 2-pyrrolyl, 3-pyrrolyl), imidazolyls (e.g., 1-imidazolyl, 2-imidazolyl, 4-imidazolyl), pyrazolyls (e.g., 1-pyrazolyl, 3-pyrazolyl, 4-pyrazolyl), triazolyls (e.g., 1,2,4-triazol-1-yl, 1,2,4-triazol-3-yl, 1,2,4-triazol-4-yl), tetrazolyls (e.g., 1-tetrazolyl, 2-tetrazolyl, 5-tetrazolyl), oxazolyls (e.g., 2-oxazolyl, 4-oxazolyl, 5-oxazolyl), isoxazolyls (e.g., 3-isoxazolyl, 4-isoxazolyl, 5-isoxazolyl), thiazolyls (e.g., 2-thiazolyl, 4-thiazolyl, 5-thiazolyl), thiadiazolyls, isothiazolyls (e.g., 3-isothiazolyl, 4-isothiazolyl, 5-isothiazolyl), pyridyls (e.g., 2-pyridyl, 3-pyridyl, 4-pyridyl), pyridazinyls (e.g., 3-pyridazinyl, 4-pyridazinyl), pyrimidinyls (e.g., 2-pyrimidinyl, 4-pyrimidinyl, 5-pyrimidinyl), furazanyls (e.g., 3-furazanyl), pyrazinyls (e.g., 2-pyrazinyl), oxadiazolyls (e.g., 1,3,4-oxadiazol-2-yl), benzofuryls (e.g., 2-benzo[b]furyl, 3-benzo[b]furyl, 4-benzo[b]furyl, 5-benzo[b]furyl, 6-benzo[b]furyl, 7-benzo[b]furyl), benzothienyls (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyls (e.g., 1-benzimidazolyl, 2-benzimidazolyl, 4-benzimidazolyl, 5-benzimidazolyl), dibenzofuryls, benzoxazolyls, benzothiazolyls, quinoxalinyls (e.g., 2-quinoxalinyl, 5-quinoxalinyl, 6-quinoxalinyl), cinnolinyls (e.g., 3-cinnolinyl, 4-cinnolinyl, 5-cinnolinyl, 6-cinnolinyl, 7-cinnolinyl, 8-cinnolinyl), quinazolinyls (e.g., 2-quinazolinyl, 4-quinazolinyl, 5-quinazolinyl, 6-quinazolinyl, 7-quinazolinyl, 8-quinazolinyl), quinolyls (e.g., 2-quinolyl, 3-quinolyl, 4-quinolyl, 5-quinolyl, 6-quinolyl, 7-quinolyl, 8-quinolyl), phthalazinyls (e.g., 1-phthalazinyl, 5-phthalazinyl, 6-phthalazinyl), isoquinolyls (e.g., 1-isoquinolyl, 3-isoquinolyl, 4-isoquinolyl, 5-isoquinolyl, 6-isoquinolyl, 7-isoquinolyl, 8-isoquinolyl), puryls, pteridinyls (e.g., 2-pteridinyl, 4-pteridinyl, 6-pteridinyl, 7-pteridinyl), carbazolyls, phenanthridinyls, acridinyls (e.g., 1-acridinyl, 2-acridinyl, 3-acridinyl, 4-acridinyl, 9-acridinyl), indolyls (e.g., 1-indolyl, 2-indolyl, 3-indolyl, 4-indolyl, 5-indolyl, 6-indolyl, 7-indolyl), isoindolyls, phenazinyls (e.g., 1-phenazinyl, 2-phenazinyl), and phenothiazinyls (e.g., 1-phenothiazinyl, 2-phenothiazinyl, 3-phenothiazinyl, 4-phenothiazinyl) and the like.

In the present invention, for example, the term "cycloalkyl" refers to cyclic saturated hydrocarbon groups and the number of carbon atoms in the cycloalkyl is, for example, 3 to 15. Examples of the aforementioned cycloalkyl include cyclopropyl, cyclobutyl, cyclopentyl, cyclohexyl, cycloheptyl, cyclooctyl, bridged cyclic hydrocarbon groups, spiro hydrocarbon groups and the like. Among them, cyclopropyl, cyclobutyl, cyclopentyl, cyclohexyl, bridged cyclic hydrocarbon groups, and the like are preferable.

In the present invention, examples of the "bridged cyclic hydrocarbon groups" include bicyclo[2.1.0]pentyl, bicyclo[2.2.1]heptyl, bicyclo[2.2.2]octyl, and bicyclo[3.2.1]octyl, tricyclo[2.2.1.0]heptyl, bicyclo[3.3.1]nonane, 1-adamantyl, 2-adamantyl and the like.

In the present invention, examples of the "spiro hydrocarbon groups" include spiro[3.4]octyl and the like.

In the present invention, the term "cycloalkenyl" encompasses, for example, unsaturated cyclic aliphatic hydrocarbon groups and the number of carbon atoms in the cycloalkenyl is, for example, 3 to 7. Examples of the aforementioned cycloalkenyl include cyclopropenyl, cyclobutenyl, cyclopentenyl, cyclohexenyl, cycloheptenyl and the like. Among them, cyclopropenyl, cyclobutenyl, cyclopentenyl, cyclohexenyl, and the like are preferable. The aforementioned term "cycloalkenyl" also encompasses, for example, bridged cyclic hydrocarbon groups and spiro hydrocarbon groups having an unsaturated bond in their rings.

In the present invention, examples of the "arylalkyl" include benzyl, 2-phenethyl, naphthalenylmethyl and the like. Examples of the "cycloalkylalkyl" and "cyclylalkyl" include cyclohexylmethyl adamantylmethyl and the like. Examples of the "hydroxyalkyl" include hydroxymethyl 2-hydroxyethyl and the like.

In the present invention, the "alkoxy" encompasses, for example, groups composed of any of the aforementioned alkyls and oxygen (alkyl-O-groups) and examples thereof include methoxy, ethoxy, n-propoxy, isopropoxy, n-butoxy and the like. Examples of the "alkoxyalkyl" include methoxymethyl and the like. Examples of the "aminoalkyl" include 2-aminoethyl and the like.

In the present invention, examples of the "heterocyclyl" include 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazolinyl, 2-imidazolinyl, 4-imidazolinyl, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, tetrahydrofuranyl and the like.

In the present invention, examples of the "heterocyclylalkyl" include piperidinylmethyl, piperazinylmethyl and the like. Examples of the "heterocyclylalkenyl" include 2-piperidinylethenyl and the like. Examples of the "heteroarylalkyl" include pyridylmethyl, quinolin-3-ylmethyl and the like.

In the present invention, the term "silyl" encompasses groups represented by the chemical formula $R_3Si—$, where R independently can be selected from the aforementioned alkyls, aryls, and cycloalkyls. Examples of the silyl include a trimethylsilyl group, a tert-butyldimethylsilyl group and the like. Examples of the "silyloxy" include a trimethylsilyloxy group and the like. Examples of the "silyloxyalkyl" include trimethylsilyloxymethyl and the like.

In the present invention, examples of the "alkylene" include methylene, ethylene, propylene and the like.

In the present invention, the above-described various groups may be substituted. Examples of the aforementioned substituent include hydroxy, carboxy, sulfo, halogen, alkyl halide (haloalkyl, e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryl (e.g., phenyl, naphthyl), arylalkyl (e.g., benzyl, phenethyl), alkylaryl (e.g., p-methylphenyl), heteroaryl (e.g., pyridyl, furyl), heteroarylalkyl (e.g., pyridylmethyl), heterocyclyl (e.g., piperidyl), heterocyclylalkenyl, heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino [alkylamino (e.g., methylamino, ethylamino, dimethylamino), acylamino (e.g., acetylamino, benzoylamino), arylalkylamino (e.g., benzylamino, tritylamino), hydroxyamino], aminoalkyl (e.g., aminomethyl), alkylaminoalkyl (e.g., diethylaminomethyl), carbamoyl, sulfamoyl, oxo, silyl, silyloxyalkyl and the like.

The natural type miRNA of the present invention may include, for example, a labeling substance, and may be labeled with the aforementioned labeling substance. The aforementioned labeling substance is not particularly limited, and may be, for example, a fluorescent substance, a dye, an isotope, or the like. Examples of the aforementioned labeling substance include: fluorophores such as pyrene, TAMRA, fluorescein, a Cy3 dye, a Cy5 dye and the like. Examples of the aforementioned dye include Alexa dyes such as Alexa 488 and the like. Examples of the aforementioned isotope include stable isotopes and radioisotopes. Among them, stable isotopes are preferable. Moreover, for example, the aforementioned stable isotope does not change the physical properties of a compound labeled therewith and thus has an excellent property as a tracer. The aforementioned stable isotope is not particularly limited, and examples thereof include $^2$H, $^{13}$C, $^{15}$N, $^{17}$O, $^{18}$O, $^{33}$S, $^{34}$S and $^{36}$S.

As described above, the natural type miRNA of the present invention can inhibit the aforementioned expression of a target gene. Thus, the natural type miRNA of the present invention can be used, for example, as a therapeutic agent for treating a disease caused by a gene. When the natural type miRNA of the present invention has a guide strand sequence of a mature miRNA that inhibits expression of a gene causing the aforementioned disease, for example, it is possible to treat the aforementioned disease by inhibiting the expression of the aforementioned target gene. In the present invention, the term "treatment" encompasses prevention of the aforementioned diseases; improvement of the diseases; and improvement in prognosis, for example, and it can mean any of them. The aforementioned disease is not particularly limited and, for example, the aforementioned sequence that inhibits expression can be set appropriately according to the object disease. Examples of the aforementioned disease include cancer such as breast cancer, lung cancer, gastric cancer, colorectal cancer, liver cancer, pancreatic cancer, esophagus cancer, prostate cancer, gall bladder cancer, uterine body cancer, uterus cervix cancer, ovarian cancer, osteosarcoma, leukemia and the like, and diseases such as lung fibrosis, hepatic fibrosis and the like.

The method of using the natural type miRNA of the present invention is not particularly limited. For example, the aforementioned natural type miRNA may be administered to a subject having the aforementioned target gene.

Examples of the aforementioned subject include cells, tissues and organs. Examples of the aforementioned subject also include humans, nonhuman animals such as nonhuman mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, COS cells and the like; stem cells such as ES cells, hematopoietic stem cells and the like; and cells isolated from living organisms, such as primary cultured cells and the like.

In the present invention, the aforementioned target gene whose expression is to be inhibited is not particularly limited, and any desired gene can be set to the target gene. As mentioned above, the aforementioned mature miRNA can be selected according to the kind of the aforementioned target gene.

As to the use of the natural type miRNA of the present invention, the following description regarding the composition, the expression inhibitory method, the treatment method, and the like according to the present invention to be describe below can be referred to.

Since the natural type miRNA of the present invention can inhibit the expression of a target gene as described above, for example, it is useful as a pharmaceutical product, a diagnostic agent, an agricultural chemical, and a tool for conducting research on agriculture, medical science, life science, and the like.

The method for synthesizing the natural type miRNA of the present invention is not particularly limited, and a conventionally known production method of nucleic acid can be employed. Examples of the aforementioned synthesis method include synthesis methods according to genetic engineering procedures, chemical synthesis methods and the like. Examples of the genetic engineering procedures include: synthesis methods utilizing in vitro transcription; methods using a vector; methods carried out using a PCR cassette and the like. The aforementioned vector is not particularly limited, and examples thereof include non-virus vectors such as plasmid and the like, and virus vectors and the like. The aforementioned chemical synthesis methods are not particularly limited, and examples thereof include a phosphoramidite method, an H-phosphonate method and the like. The aforementioned chemical synthesis methods can be carried out, for example, using a commercially available automated nucleic acid synthesizer. In the aforementioned chemical synthesis methods, an amidite is generally used. The aforementioned amidite is not particularly limited. Examples of commercially available amidites include RNA Phosphoramidites (2'-O-TBDMSi, trade name, Samchully Pharm. Co., Ltd.), ACE amidite, TOM amidite, CEE amidite, CEM amidite, TEM amidite and the like.

(2) Composition

The expression inhibitory composition according to the present invention is, as described above, a composition for inhibiting the expression of a target gene, characteristically containing the aforementioned natural type miRNA of the present invention. The composition of the present invention is characterized in that it contains the aforementioned natural type miRNA of the present invention, and other configurations are by no means limited. The expression inhibitory composition of the present invention can also be referred to, for example, as an expression inhibitory reagent.

According to the present invention, for example, by administering to a subject in which the aforementioned target gene is present, it is possible to inhibit the expression of the aforementioned target gene.

Furthermore, as described above, the pharmaceutical composition according to the present invention characteristically contains the aforementioned natural type miRNA of the present invention. The composition of the present invention is characterized in that it contains the aforementioned natural type miRNA of the present invention, and other configurations are by no means limited. The pharmaceutical composition of the present invention can also be referred to, for example, as a pharmaceutical product.

According to the present invention, for example, administration to a patient with a disease caused by a gene can inhibit the expression of the aforementioned gene, thereby treating the aforementioned disease. In the present invention, the term "treatment" encompasses, as mentioned above, prevention of the aforementioned diseases; improvement of the diseases; and improvement in prognosis, for example, and it can mean any of them.

In the present invention, a disease to be treated is not particularly limited, and examples thereof include diseases caused by the expression of genes. Depending on the kind of the aforementioned disease, a gene that causes the disease may be set as the aforementioned target gene, and further, depending on the aforementioned target gene, the aforementioned guide strand sequence of the aforementioned mature miRNA may be selected.

The method of using the expression inhibitory composition and the pharmaceutical composition according to the present invention (hereinafter, both the compositions simply are referred to as "the compositions") are not particularly limited, and examples thereof include administering the aforementioned natural type miRNA to a subject having the aforementioned target gene.

Examples of the aforementioned subject include cells, tissues, and organs. Examples of the aforementioned subject also include humans, nonhuman animals such as nonhuman mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, COS cells and the like; stem cells such as ES cells, hematopoietic stem cells and the like; and cells isolated from living organisms, such as primary cultured cells and the like.

The aforementioned administration method is not particularly limited, and can be determined, for example, as appropriate depending on the subject. When the aforementioned subject is a cultured cell, the administration method may be, for example, a method using a transfection reagent, an electroporation method, or the like.

For example, each of the compositions of the present invention may contain only the natural type miRNA of the present invention or further may contain an additive(s) in addition to the natural type miRNA. The aforementioned additive is not particularly limited, and is preferably, for example, a pharmaceutically acceptable additive. The kind of the aforementioned additive is not particularly limited, and can be selected as appropriate depending on, for example, the kind of the subject.

In the composition of the present invention, for example, the aforementioned natural type miRNA may form a complex with the aforementioned additive. The aforementioned additive can also be referred to, for example, as a complexing agent. The aforementioned complex formation allows, for example, the aforementioned natural type miRNA to be delivered efficiently.

The aforementioned complexing agent is not particularly limited, and examples thereof include polymers, cyclodextrins, adamantine and the like. Examples of the aforementioned cyclodextrins include linear cyclodextrin copolymers, linear oxidized cyclodextrin copolymers and the like.

Other examples of the aforementioned additive include a carrier, a binding substance that binds to a target cell, a condensing agent, a fusogenic agent, an excipient and the like.

(3) Expression Inhibitory Method

The expression inhibitory method according to the present invention is, as described above, a method for inhibiting the expression of a target gene, in which the aforementioned natural type miRNA of the present invention is characteristically used. The expression inhibitory method of the present invention is characterized in that the aforementioned natural type miRNA of the present invention is used therein, and other steps and conditions are by no means limited.

In the expression inhibitory method of the present invention, the mechanism by which the aforementioned target gene expression is inhibited is not particularly limited, and examples thereof include inhibition of the expression by mature miRNA.

The expression inhibitory method of the present invention includes, for example, the step of administering the aforementioned natural type miRNA to a subject in which the aforementioned target gene is present. By the aforementioned administration step, for example, the aforementioned natural type miRNA is brought into contact with the aforementioned subject. Examples of the aforementioned subject include cells, tissues, and organs. Examples of the aforementioned subject also include humans, nonhuman animals such as nonhuman mammals excluding humans. The aforementioned administration may be performed, for example, in vivo or in vitro.

In the expression inhibitory method of the present invention, for example, the aforementioned natural type miRNA alone may be administered, or the aforementioned composition of the present invention containing the aforementioned natural type miRNA may be administered. The aforementioned administration method is not particularly limited and, for example, can be selected as appropriate depending on the kind of the subject.

(4) Treatment Method

As described above, the method for treating a disease according to the present invention includes the step of administering the aforementioned natural type miRNA of the present invention to a patient, and is characterized in that the aforementioned guide strand sequence in the aforementioned natural type miRNA is the guide strand sequence of a mature miRNA that inhibits expression of a gene causing the aforementioned disease. The treatment method of the present invention is characterized by the use of the aforementioned natural type miRNA of the present invention, and other steps and conditions are by no means limited.

The aforementioned expression inhibitory method of the present invention also applies to, for example, the treatment method of the present invention. The aforementioned administration method is not particularly limited and may be, for example, any of oral administration and parenteral administration.

(5) Use of Natural Type miRNA

The use according to the present invention is the use of the aforementioned natural type miRNA of the present invention for the aforementioned inhibition of the expression of a target gene.

The single-stranded nucleic acid according to the present invention is a single-stranded nucleic acid for use in the treatment of a disease. The aforementioned single-stranded nucleic acid is the aforementioned natural type miRNA of the present invention, and is characterized in that the aforementioned guide strand sequence in the aforementioned natural type miRNA is the guide strand sequence of a mature miRNA that inhibits expression of a gene causing the aforementioned disease.

In the following, the present invention will be described in detail with reference to examples and the like. It is to be noted, however, that the present invention is by no means limited thereto.

EXAMPLES

Example 1

Based on the sequence information of the guide strand and the passenger strand of mature miR-34a (miRBase Accession No. MI0000268), various natural type miRNAs of the present invention having a different base length of the additional sequence (spacer) were synthesized, introduced into cultured cells and an inhibitory effect on the expression of the target gene AXL mRNA was examined.

(1) Synthesis of miRNA

A double-stranded human mature miR-34a (NI-0208) composed of the guide strand (SEQ ID NO: 1) and the passenger strand (SEQ ID NO: 2) shown below was synthesized as a positive control miRNA, and a single-stranded natural type miR-34a (NM-0004) wherein the aforementioned guide strand is linked with the aforementioned passenger strand via the sequence of a loop region of pre-miR-34a was synthesized.

As a negative control, double-stranded RNA (NI-0000) composed of a sequence free of complementarity to all sequences recorded on nucleic acid databases and a sequence complementary thereto was synthesized.

NM-0004 (64 mer)

NM-0004 (64 mer)

(SEQ ID NO: 11)

```
 U        A              -GUGA    A
  GGCAGUGU-CUU GCUGGUUGUU      GC
                                   A
                                   U
    CCGUCAUA    GAA-CGACUAACGA    UG
 UC        * U            *    *   AGGAA*  A
  *
```

NI-0208 (22/22 mer)

(SEQ ID NO: 1)

```
 U        A
  GGCAGUGU-CUU GCUGGUUGUU
```

(SEQ ID NO: 2)

```
    CCGUCAUA    GAA-CGACUAAC
 UC        * U            *
  *
```

In the aforementioned sequence, an asterisk shows a base non-complementary to the corresponding guide strand base.

In the following sequence, the underlined part is the aforementioned guide strand sequence, and the lower-case letters show the aforementioned passenger strand sequence.

NM-0004
(SEQ ID NO: 11)
5'-UGGCAGUGUCUUAGCUGGUUGUUGUGAGCAAUAGUAAGGAAGcaau cagcaaguauacugcccu-3'

NI-0208
(SEQ ID NO: 1/SEQ ID NO: 2)
5'-UGGCAGUGUCUUAGCUGGUUGU-3'/5'-caaucagcaaguauacu gcccu-3'

NI-0000
(SEQ ID NO: 12/SEQ ID NO: 13)
5'-UACUAUUCGACACGCGAAGTT-3'/5'-CUUCGCGUGUCGAAUAGU

ATT-3'

As a natural type miRNA of the Example, a natural type miR-34a wherein X region composed of the aforementioned guide strand (SEQ ID NO: 1) and an additional sequence (0, 3, 5 or 7 base length), and Y region having, at the 5'-terminus of the aforementioned passenger strand, an overhang region of the aforementioned guide strand and a sequence completely complementary to the aforementioned additional sequence, are linked via a non-nucleotide structure of a proline derivative of the following formula, was synthesized. In the synthesis of the aforementioned natural type miRNA, the non-nucleotide structures of the proline derivatives of the following formulas were introduced by using L-proline diamide amidite (see WO 2012/017919).

PH-0036 (46 mer)

(SEQ ID NO: 14)

```
 U        A
  GGCAGUGU-CUU GCUGGUUGU
                         P
    CCGUCAUA    GAA-CGACUAACA
 UC        U
   *    *    *
``` spacer 3

PH-0038 (52 mer)

(SEQ ID NO: 15)

```
 U        A
  GGCAGUGU-CUU GCUGGUUGUUCC
                           P
    CCGUCAUA    GAA-CGACUAACAAGG
 UC        U
   *    *    *
``` spacer 5

PH-0066 (56 mer)

(SEQ ID NO: 16)

```
 U        A
  GGCAGUGU-CUU GCUGGUUGUUCCGG
                             P
    CCGUCAUA    GAA-CGACUAACAAGGCC
 UC        U
   *    *    *
``` spacer 7

PH-0068 (60 mer)

(SEQ ID NO: 17)

```
 U        A
  GGCAGUGU-CUU GCUGGUUGUUCCGGCC
                               P
    CCGUCAUA    GAA-CGACUAACAAGGCCGG
 UC        U
   *    *    *
```

In the aforementioned sequences, an asterisk shows a base non-complementary to the corresponding guide strand. In addition, the number after the "spacer" shows the base length of the additional sequence of the aforementioned X region.

In the following sequence, the underlined part is the aforementioned guide strand sequence, and the lower-case letters show the aforementioned passenger strand sequence. In addition, [P] shows a non-nucleotide structure of the aforementioned proline derivative.

PH-0036
(SEQ ID NO: 14)
5'-UGGCAGUGUCUUAGCUGGUUGU-[P]-Acaaucagcaaguauacug cccu-3'

PH-0038
(SEQ ID NO: 15)
5'-UGGCAGUGUCUUAGCUGGUUGUUCC-[P]-

GGAAcaaucagcaaguauacugcccu-3'

-continued

PH-0066
(SEQ ID NO: 16)
5'-UGGCAGUGUCUUAGCUGGUUGUUCCGG-[P]-

CCGGAAcaaucagcaaguauacugcccu-3'

PH-0068
(SEQ ID NO: 17)
5'-UGGCAGUGUCUUAGCUGGUUGUUCCGGCC-[P]-

GGCCGGAAcaaucagcaaguauacugcccu-3'

(2) Measurement of Expression Level of AXL Gene

Each of the aforementioned RNAs was dissolved in distilled water for injection (Otsuka Pharmaceutical Co., Ltd.) at 2 µmol/L, whereby an RNA solution was prepared.

H1299 cells (ATCC) were used as the cell. As the medium, RPMI Medium 1640 (Life Technologies) containing 10% FBS was used. The culture conditions were set to 37° C., 5% $CO_2$.

First, the cells were cultured in the aforementioned medium, and the cultured solution was dispensed to a 24-well plate so that each well contained 400 µL of the cultured solution to achieve a density of $4 \times 10^4$ cells/well. The cells were transfected with the aforementioned RNA using (A) transfection reagent Lipofectamine RNAiMAX (Life Technologies) according to the protocol attached to the aforementioned transfection reagent. Specifically, the transfection was carried out by setting the composition per well as follows. In the following composition, (B) is Opti-MEM (Life Technologies), (C) is the aforementioned 2 µmol/L RNA solution, 98.5 µL in total of them was added. The final concentration of the aforementioned RNA in the aforementioned well was set to 1 nmol/L.

TABLE 1

| (composition per well: µL) | |
| --- | --- |
| cultured solution | 400 |
| transfection reagent | 1.5 |
| (B) + (C) | 98.5 |
| total | 500 |

After the transfection, the cells in the aforementioned wells were cultured for 24 hours, and then, the RNA was collected using an RNeasy Mini Kit (Qiagen, Netherlands) according to the protocol supplied therewith. Subsequently, cDNA was synthesized from the aforementioned RNA by using Transcriptor First Strand cDNA Synthesis Kit (Roche) according to the protocol supplied therewith. Then, as shown below, PCR was carried out using the aforementioned synthesized cDNA as a template, and the expression level of the AXL gene and that of GAPDH gene as an internal standard were measured. The aforementioned expression level of the AXL gene was normalized with reference to that of the GAPDH gene mentioned above.

The aforementioned PCR was carried out using LightCycler 480 SYBR Green I Master (trade name, Roche) as a reagent and LightCycler 480 Instrument II (trade name, Roche) as an instrument (hereinafter the same). The aforementioned AXL and GAPDH genes were amplified using the following primer sets, respectively.

PCR primer set for AXL gene
(SEQ ID NO: 18)
5'-CTCAACCAGGACGACTCCAT-3'

(SEQ ID NO: 19)
5'-AGACCGCTTCACTCAGGAAA-3' primer set for GAPDH gene
(SEQ ID NO: 20)
5'-ATGGGGAAGGTGAAGGTCG-3'

(SEQ ID NO: 21)
5'-GGGTCATTGATGGCAACAATATC-3'

As control 1, regarding the cells to which 100 µL of the aforementioned solution (B) alone had been added to the aforementioned cultured solution, the expression levels of the genes also were measured (−). Furthermore, as control 2, regarding the cells subjected to the same transfection procedures as in the above except that the aforementioned RNA solution was not added and that the aforementioned (B) and 1.5 µL of the aforementioned (A) were added so that the total amount of (A) and (B) would be 100 µL, the expression level of the gene also was measured (mock).

As for the expression levels of normalized AXL gene, the relative value of the expression level in the cell introduced with each RNA was determined based on the expression level in the cells of the control (−) as 1.

(3) Results

Figure 2:
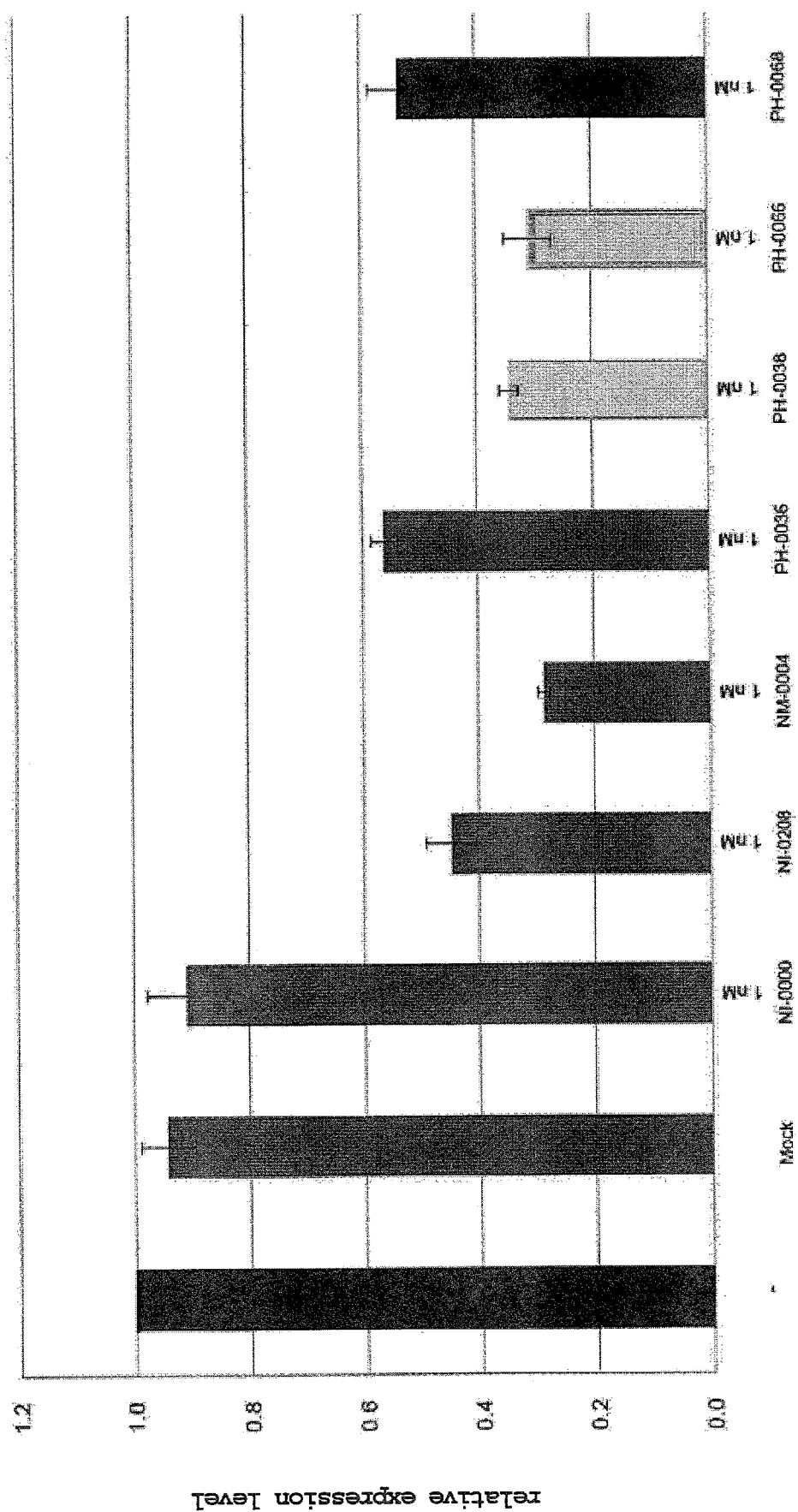
FIG. 2 is a graph showing the relative values of AXL mRNA amount in Example 1.

As shown in FIG. 2, natural type miR-34a of the Example inhibited expression of AXL mRNA at the same level as that by the positive control mature miR-34a and pre-miR-34a variant. In addition, an inhibitory effect on the expression of AXL mRNA was maintained even when the base length of the additional sequence of the X region was changed.

Example 2

In the natural type miR-34a (PH-0036) of Example 1, non-nucleotide structure of the linker region was modified, and an inhibitory effect on the expression of AXL mRNA was similarly examined.

(1) Synthesis of miRNA

As shown below, molecule (KH-0006) wherein the non-nucleotide structure of a lysine derivative of the following formula was substituted by a linker region of PH-0036,

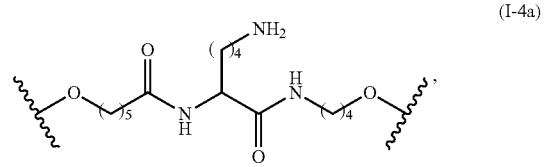
(I-4a)

molecule (XH-0011) wherein the non-nucleotide structure of a glycine derivative of the following formula was substituted by a linker region of PH-0036,

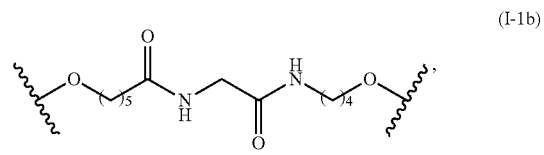
(I-1b)

molecule (XH-0013) wherein the non-nucleotide structure of a glycylglycine derivative of the following formula was substituted by a linker region of PH-0036,

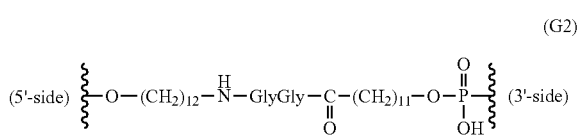

GlyGly in the aforementioned chemical formula (G2) is an atomic group represented by the following chemical formula (GlyGly), wherein the terminal carbonylcarbon is bonded to N atom in the above-mentioned chemical formula (G2), and the terminal nitrogen atom in the following chemical formula (GlyGly) is bonded to carbonylcarbon in the above-mentioned chemical formula (G2), (GlyGly)

—HN—CH$_2$—CO—HN—CH$_2$—CO—, and molecule (XH-0015) wherein the non-nucleotide structure of a terephthalic acid derivative of the following formula was substituted by a linker region of PH-0036,

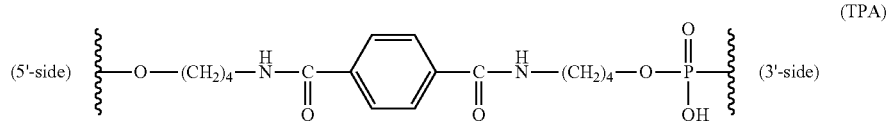

were each synthesized. The non-nucleotide structure of the aforementioned lysine derivative was introduced by using L-lysin amideamidite (see WO 2013/103146), the non-nucleotide structure of the aforementioned glycine derivative was introduced by using glycine amideamidite (see WO 2013/103146), the non-nucleotide structure of the aforementioned glycylglycine derivative was introduced by using glycylglycine amideamidite (see WO 2013/133221), and the non-nucleotide structure of the aforementioned terephthalic acid derivative was introduced by using terephthalic acid amidite (see WO 2013/103221).

```
KH-0006
                                          (SEQ ID NO: 14)
    U          A
 GGCAGUGU-CUU GCUGGUUGU
UC CCGUCAUA GAA-CGACUAACA K
          U
XH-0011
                                          (SEQ ID NO: 14)
    U          A
 GGCAGUGU-CUU GCUGGUUGU
UC CCGUCAUA GAA-CGACUAACA Gly
          U
XH-0013
                                          (SEQ ID NO: 14)
    U          A
 GGCAGUGU-CUU GCUGGUUGU
UC CCGUCAUA GAA-CGACUAACA GlyGly
          U
XH-0015
                                          (SEQ ID NO: 14)
    U          A
 GGCAGUGU-CUU GCUGGUUGU
UC CCGUCAUA GAA-CGACUAACA TP
          U
```

In the following sequence, [K] shows the non-nucleotide structure of the aforementioned lysine derivative, [Gly] shows the non-nucleotide structure of the aforementioned glycine derivative, [GlyGly] shows the non-nucleotide structure of the aforementioned glycylglycine derivative, and [TP] shows the non-nucleotide structure of the aforementioned terephthalic acid. In the following sequences, the 5'-side region of each linker is X region, and in the aforementioned X region, the underlined part is the aforementioned guide strand sequence, the rest is the aforementioned additional sequence, and the 3'-side region of each linker is Y region, and in the aforementioned Y region, the lower-case letters show the aforementioned passenger strand sequence.

```
KH-0006
                                          (SEQ ID NO: 14)
5'-UGGCAGUGUCUUAGCUGGUUGU-[K]-Acaaucagcaaguauacug cccu-3'

XH-0011
                                          (SEQ ID NO: 14)
5'-UGGCAGUGUCUUAGCUGGUUGU-[Gly]-Acaaucagcaaguauac ugcccu-3'
```

-continued

```
XH-0013
                                          (SEQ ID NO: 14)
5'-UGGCAGUGUCUUAGCUGGUUGU-[GlyGly]-

Acaaucagcaaguauacugcccu-3'

XH-0015
                                          (SEQ ID NO: 14)
5'-UGGCAGUGUCUUAGCUGGUUGU-[TP]-Acaaucagcaaguauac ugcccu-3'
```

Similar to Example 1, NM-0004 and NI-0208 were used as a positive control, and NI-0000 was used as a negative control.

(2) Measurement of Expression Level of AXL Gene

By a method similar to that in Example 1, H1299 cells (ATCC) were transfected with each of the aforementioned RNAs, and the expression level of AXL mRNA was determined.

(3) Results

Figure 3:
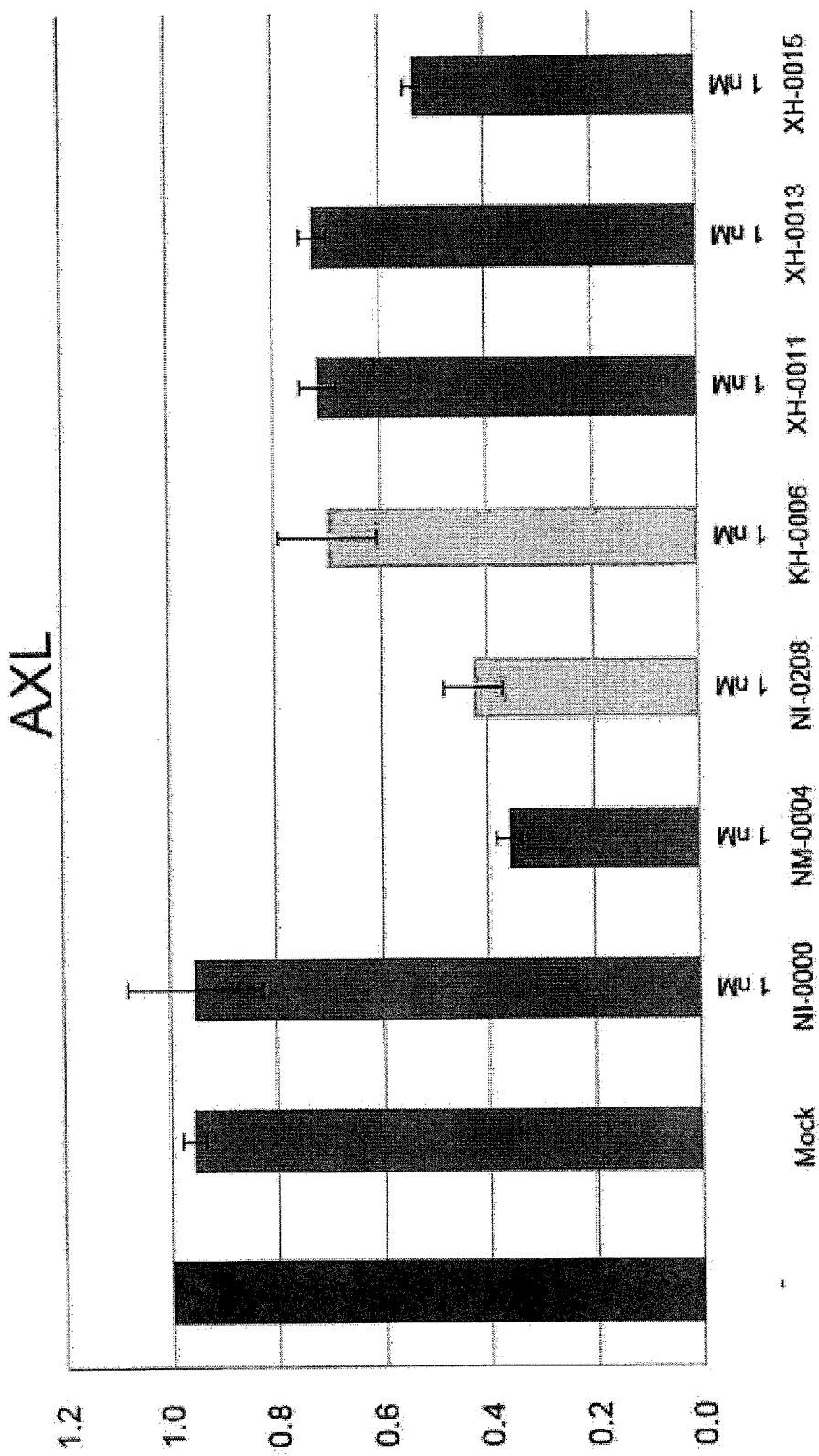
FIG. 3 is a graph showing the relative values of AXL mRNA amount in Example 2.

As shown in FIG. 3, an inhibitory effect on the expression of AXL mRNA was maintained even when the non-nucleotide structure of the linker region was altered.

Example 3

Then, an effect of the introduction of an additional sequence into the X region on XH-0015 having a linker region of the non-nucleotide structure of the terephthalic acid derivative, which was used in Example 2, was examined. The structure and sequence of the natural type miR-34a used are shown below.

XH-0015 (46 mer)

(SEQ ID NO: 14)

```
 U GGCAGUGU-CUU A GCUGGUUGU
UC CCGUCAUA U GAA-CGACUAACA TP
   *        *       *
```

[spacer]

XH-0024 (52 mer)

(SEQ ID NO: 15)

```
 U GGCAGUGU-CUU A GCUGGUUGUUCC
UC CCGUCAUA U GAA-CGACUAACAAGG TP
   *        *       *
```

In the aforementioned sequence, an asterisk shows a base non-complementary to the corresponding guide strand. The "spacer" shows that the aforementioned X region contains an additional sequence.

In the following sequence, the underlined part is the aforementioned guide strand sequence, and the lower-case letters show the aforementioned passenger strand sequence. [TP] shows the non-nucleotide structure of the aforementioned terephthalic acid derivative.

XH-0015

(SEQ ID NO: 14)

5'-UGGCAGUGUCUUAGCUGGUUGU-[TP]-Acaaucagcaaguauacugcccu-3'

XH-0024

(SEQ ID NO: 15)

5'-UGGCAGUGUCUUAGCUGGUUGUUCC-[TP]-GGAAcaaucagcaaguauacugcccu-3'

By a method similar to that in Example 1, H1299 cells (ATCC) were transfected with each of the aforementioned RNAs, and the expression level of AXL mRNA was determined.

Figure 4:
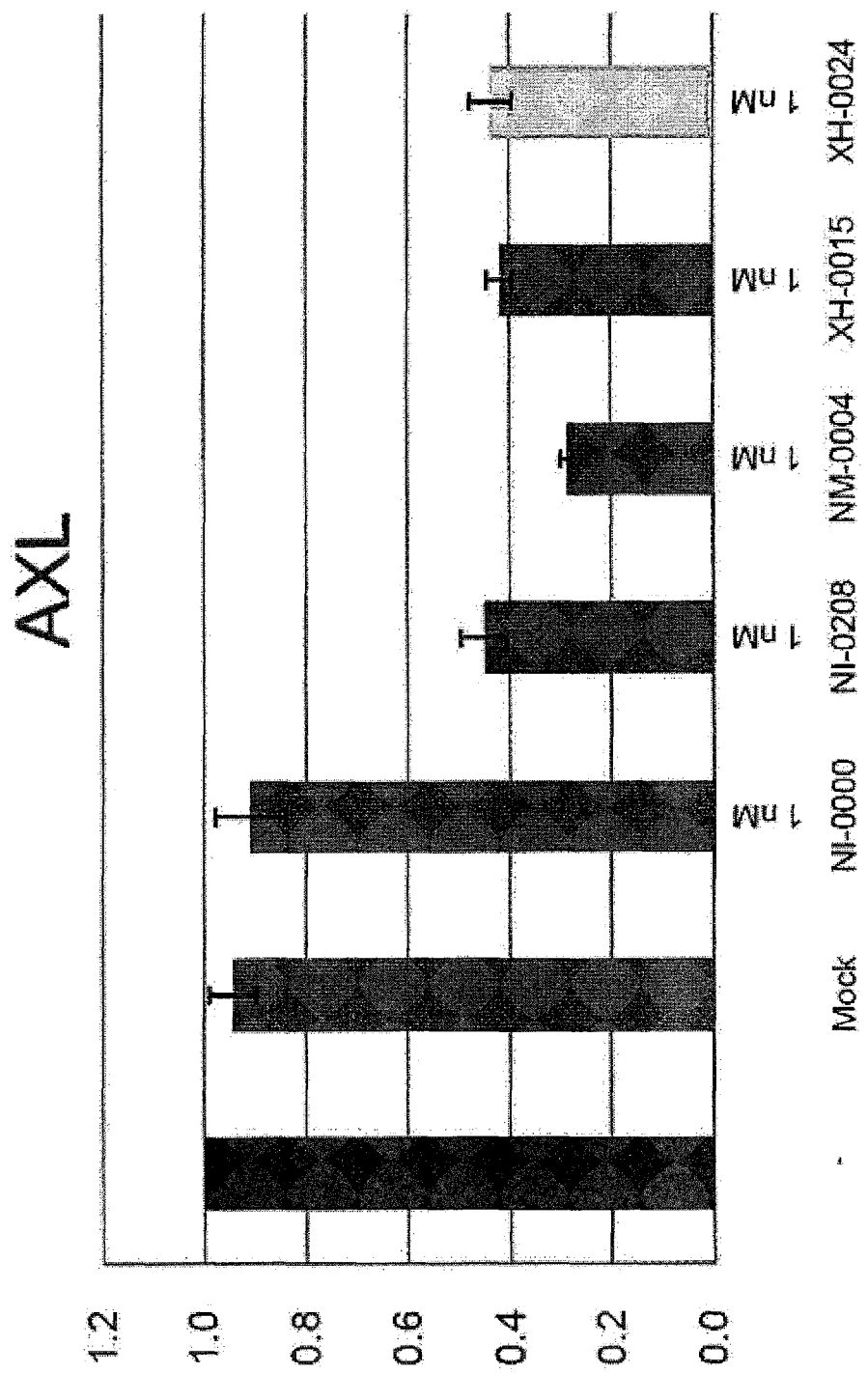
FIG. 4 is a graph showing the relative values of AXL mRNA amount in Example 3.

As a result, as shown in FIG. 4, an inhibitory effect on the expression of AXL mRNA was maintained even when an additional sequence was added to the X region.

Example 4

Based on the sequence information of the guide strand and the passenger strand of mature let-7a (miRBase Accession No. MI0000060), various natural type miRNAs of the present invention having a different non-nucleotide structure of the linker region were synthesized, introduced into cultured cells and an inhibitory effect on the expression of the target gene HMGA2 mRNA was examined. When the natural type miRNA uses a linker having a non-nucleotide structure of a proline derivative, one having an additional sequence introduced into the X region was also synthesized.

(1) Synthesis of miRNA

A double-stranded human mature let-7a (NI-0205) composed of the guide strand (SEQ ID NO: 3) and the passenger strand (SEQ ID NO: 4) shown below was synthesized as a positive control miRNA, and a single-stranded natural type let-7a (NM-0003) wherein the aforementioned guide strand is linked with the aforementioned passenger strand via the sequence of a loop region of pre-let-7a was synthesized.

In addition, as a negative control, the aforementioned NI-0000 was used.

NM-0003 (72 mer)

(SEQ ID NO: 22)

```
 U    GU  AGUAGGUUGUAUAGUU UUAGGGUCACAC
 GAG                                   C
                                       C
CU-UUC   UCAUCUAACAUAUCAA              A
   * UG         *       UAGAGGGUCACC
       * *
```

NI-0205 (22/21 mer)

(SEQ ID NO: 3)

```
 U    GU
 GAG    AGUAGGUUGUAUAGUU
```

(SEQ ID NO: 4)

```
CU-UUC   UCAUCUAACAUAUC
   * UG         *
       * *
```

In the aforementioned sequence, an asterisk shows a base non-complementary to the corresponding guide strand.

In the following sequences, the underlined part shows the aforementioned guide strand sequence, and lower-case letters show the aforementioned passenger strand sequence.

NM-0003

(SEQ ID NO: 22)

5'-UGAGGUAGUAGGUUGUAUAGUUUUAGGGUCACACCCACCACUGGGA

GAUAAcuauacaaucuacugucuuuc-3'

NI-0205

(SEQ ID NO: 3/SEQ ID NO: 4)

5'-UGAGGUAGUAGGUUGUAUAGUU-3'/5'-cuauacaaucuacugu cuuuc-3'

As shown below, various natural type let-7a wherein X region composed of the aforementioned guide strand (SEQ ID NO: 3) and an additional sequence (0, 3 base length), and Y region having, at the 5'-terminus of the aforementioned passenger strand, an overhang region of the aforementioned guide strand and a sequence completely complementary to the aforementioned additional sequence, are linked via a linker of the aforementioned proline derivative ([P]), lysine derivative ([K]), glycine derivative ([Gly]), glycylglycine derivative ([GlyGly]) or terephthalic acid derivative ([TP]), were synthesized. In the aforementioned synthesis of the natural type miRNA, each non-nucleotide structure was introduced in the same manner as in Examples 1 and 2.

PH-0011

(SEQ ID NO: 23)

```
 U    GU   AGUAGGUUGUAUAGUU
 GAG                       P
CU-UUC    UCAUCUAACAUAUCAA
      UG
```

KH-0003

(SEQ ID NO: 23)

```
 U    GU   AGUAGGUUGUAUAGUU
 GAG                       K
CU-UUC    UCAUCUAACAUAUCAA
      UG
```

XH-0002

```
                                              (SEQ ID NO: 23)
       U   GU
     GAG    AGUAGGUUGUAUAGUU
  CU-UUC    UCAUCUAACAUAUCAA   Gly
       UG
XH-0004

(SEQ ID NO: 23)
       U   GU
     GAG    AGUAGGUUGUAUAGUU
  CU-UUC    UCAUCUAACAUAUCAA   GlyGly
       UG
XH-0006

(SEQ ID NO: 23)
       U   GU
     GAG    AGUAGGUUGUAUAGUU
  CU-UUC    UCAUCUAACAUAUCAA   TP
       UG
PH-0014

(SEQ ID NO: 24)
            U   GU
          GAG    AGUAGGUUGUAUAGUUCC
[spacer] CU-UUC   UCAUCUAACAUAUCAAGG   P
            UG
```

In the aforementioned sequence, the "spacer" shows that the aforementioned X region contains an additional sequence.

In the following sequence, [P] shows the non-nucleotide structure of the aforementioned proline derivative, [K] shows the non-nucleotide structure of the aforementioned lysine derivative, [Gly] shows the non-nucleotide structure of the aforementioned glycine derivative, [GlyGly] shows the non-nucleotide structure of the aforementioned glycylglycine derivative, and [TP] shows the non-nucleotide structure of the aforementioned terephthalic acid. In the following sequences, the 5'-side region of each linker is X region, and in the aforementioned X region, the underlined part is the aforementioned guide strand sequence, and the rest is the aforementioned additional sequence, and the 3'-side region of each linker is Y region, and in the aforementioned Y region, the lower-case letters show the aforementioned passenger strand sequence.

PH-0011
                                              (SEQ ID NO: 23)
5'-UGAGGUAGUAGGUUGUAUAGUU-[P]-AAcuauacaaucuacuguc
uuuc-3'

KH-0003
                                              (SEQ ID NO: 23)
5'-UGAGGUAGUAGGUUGUAUAGUU-[K]-AAcuauacaaucuacuguc
uuuc-3'

XH-0002
                                              (SEQ ID NO: 23)
5'-UGAGGUAGUAGGUUGUAUAGUU-[Gly]-AAcuauacaaucuacug
ucuuuc-3'

XH-0004
                                              (SEQ ID NO: 23)
5'-UGAGGUAGUAGGUUGUAUAGUU-[GlyGly]-
AAcuauacaaucuacugucuuuc-3'

XH-0006
                                              (SEQ ID NO: 23)
5'-UGAGGUAGUAGGUUGUAUAGUU-[TP]-AAcuauacaaucuacugu
cuuuc-3'

PH-0014
                                              (SEQ ID NO: 24)
5'-UGAGGUAGUAGGUUGUAUAGUUCC-[P]-
GGAAAcuauacaaucuacugucuuuc-3'

(2) Measurement of Expression Level of HMGA2 Gene

Each of the aforementioned RNAs was dissolved in distilled water for injection (Otsuka Pharmaceutical Co., Ltd.) at 0.2 µmol/L, whereby an RNA solution was prepared.

A549 cells (DS Pharma Biomedical Co., Ltd.) were used as the cells. A 10% FBS-containing DMEM (Life Technologies) was used as the medium. The culture conditions were set to 37° C. and 5% $CO_2$.

First, the cells were cultured in the aforementioned medium, and the cultured solution was dispensed to a 24-well plate so that each well contained 400 µL of the cultured solution to achieve a density of $4 \times 10^4$ cells/well. The cells were transfected with the aforementioned RNA using (A) transfection reagent Lipofectamine RNAiMAX (Life Technologies) according to the protocol attached to the aforementioned transfection reagent. Specifically, the transfection was carried out by setting the composition per well as follows. In the following composition, (B) is Opti-MEM (Life Technologies), and (C) is 0.2 µmol/L aforementioned RNA solution and 98.5 µL in total of them was added. The final concentration of the aforementioned RNA in the aforementioned well was set to 0.1 nmol/L.

TABLE 2

| (composition per well: µL) | |
| --- | --- |
| cultured solution | 400 |
| transfection reagent | 1.5 |
| (B) + (C) | 98.5 |
| total | 500 |

After the transfection, the cells in the aforementioned wells were cultured for 24 hours, and then, the RNA was collected using an RNeasy Mini Kit (Qiagen, Netherlands) according to the protocol supplied therewith. Subsequently, cDNA was synthesized from the aforementioned RNA by using Transcriptor First Strand cDNA Synthesis Kit (Roche) according to the protocol supplied therewith. Then, as shown below, PCR was carried out using the aforementioned synthesized cDNA as a template, and the expression level of the HMGA2 gene and that of GAPDH gene as an internal standard were measured. The aforementioned expression level of the HMGA2 gene was normalized with reference to that of the GAPDH gene mentioned above.

The aforementioned PCR was carried out using LightCycler 480 SYBR Green I Master (trade name, Roche) as a reagent and LightCycler 480 Instrument II (trade name, Roche) as an instrument (hereinafter the same). The aforementioned HMGA2 and GAPDH genes were amplified using the following primer sets, respectively.

```
PCR primer set for HMGA2 gene
                              (SEQ ID NO: 25)
5'-GAAGCCACTGGAGAAAAACG-3'

(SEQ ID NO: 26)
5'-CTTCGGCAGACTCTTGTGAG-3' primer set for GAPDH gene
                              (SEQ ID NO: 20)
5'-ATGGGGAAGGTGAAGGTCG-3'

(SEQ ID NO: 21)
5'-GGGTCATTGATGGCAACAATATC-3'
```

As control 1, regarding the cells to which 100 μL of the aforementioned solution (B) alone had been added to the aforementioned cultured solution, the expression levels of the genes also were measured (−). Furthermore, as control 2, regarding the cells subjected to the same transfection procedures as in the above except that the aforementioned RNA solution was not added and that the aforementioned (B) and 1.5 μL of the aforementioned (A) were added so that the total amount of (A) and (B) would be 100 μL, the expression level of the gene also was measured (mock).

As for the expression level of normalized HMGA2 gene, the relative value of the expression level in the cell introduced with each RNA was determined based on the expression level in the cells of the control (−) as 1.

(3) Results

Figure 5:
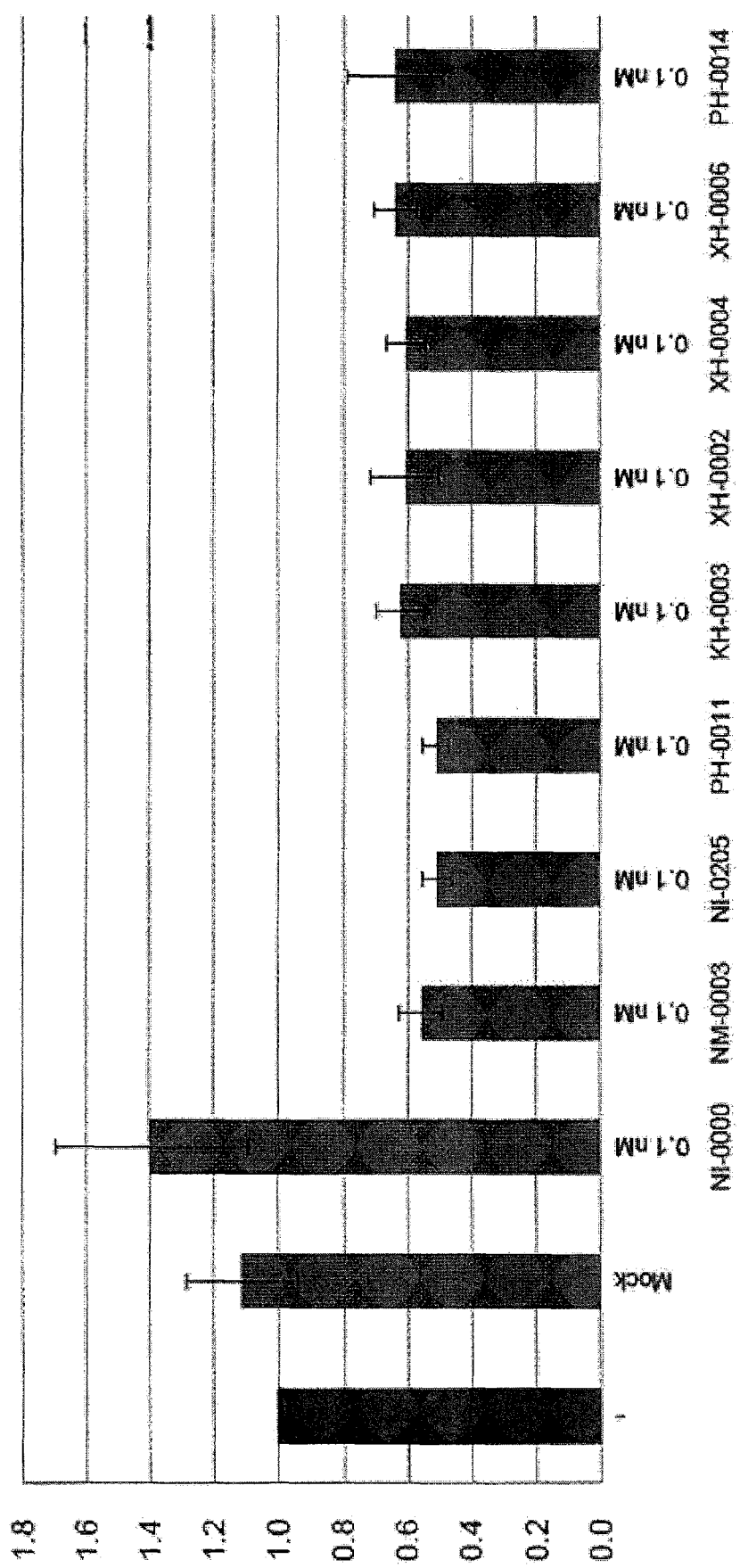
FIG. 5 is a graph showing the relative values of HMGA2 mRNA amount in Example 4.

As shown in FIG. 5, natural type let-7a of the Example inhibited expression of HMGA2 mRNA at the same level as that by the positive control mature let-7a and pre-let-7a variant. In addition, an inhibitory effect on the expression of HMGA2 mRNA was maintained even when the non-nucleotide structure of the linker was altered or the additional sequence was introduction into X region.

Example 5

Based on the sequence information of the guide strand and the passenger strand of mature miR-29b (miRBase Accession No. MI0000105), various natural type miRNAs of the present invention having a different non-nucleotide structure of the linker region were synthesized, introduced into cultured cells and an inhibitory effect on the expression of the target gene COL1A1 mRNA was examined. When the natural type miRNA uses a linker having a non-nucleotide structure of a proline derivative, one having an additional sequence introduced into the X region was also synthesized.

(1) Synthesis of miRNA

A double-stranded human mature miR-29b (NI-0210) composed of the guide strand (SEQ ID NO: 9) and the passenger strand (SEQ ID NO: 10) shown below was synthesized as a positive control miRNA, and a single-stranded natural type miR-29b (NM-0005) wherein the aforementioned guide strand is linked with the aforementioned passenger strand via the sequence of a loop region of pre-miR-29b was synthesized.

In addition, as a negative control, the aforementioned NI-0000 was used.

```
NM-0005 (64 mer)
                              (SEQ ID NO: 27)
   *  *   U      *   GU*  *UUAAA
 -GCUGGUUUCA AUGGUG   UUAGAU     U
                                  A
 UU UGACUAAAGU UACCAC--GAUCUG   G
  G          U             UUAGU
NI-0210 (24/23 mer)
                              (SEQ ID NO: 9)
   *  *   U      GU*
 GCUGGUUUCA AUGGUG   UUAGA (SEQ ID NO: 10)
 UUGUGACUAAAGU UACCAC--GAU
              U
```

In the aforementioned sequence, an asterisk shows a base non-complementary to the corresponding guide strand.

In the following sequence, the underlined part is the aforementioned guide strand sequence, the lower-case letters show the aforementioned passenger strand sequence.

```
NM-0005
                              (SEQ ID NO: 27)
5'-gcugguuucauauggugguuuagaUUUAAAUAGUGAUUGUCUAG

CACCAUUUGAAAUCAGUGUU-3'

NI-0210
                      (SEQ ID NO: 10/SEQ ID NO: 9)
5'-gcugguuucauauggugguuuaga-3'/5'-

UAGCACCAUUUGAAAUCAGUGUU-3'
```

As shown below, various natural type miR-29b wherein X region composed of the aforementioned passenger strand (SEQ ID NO: 10) and an additional sequence (0, 3 base length), and Y region having, at the 5'-terminus of the aforementioned guide strand, an overhang region of the aforementioned passenger strand and a sequence completely complementary to the aforementioned additional sequence, are linked via a linker of the aforementioned proline derivative ([P]), lysine derivative ([K]), glycine derivative ([Gly]), glycylglycine derivative ([GlyGly]) or terephthalic acid derivative ([TP]), were synthesized. In the aforementioned synthesis of the natural type miRNA, each non-nucleotide structure was introduced in the same manner as in Examples 1 and 2.

PH-0040

(SEQ ID NO: 28)
```
  GCUGGUUUCA^U AUGGUG^GU UUAGA
                                P
  UUGUGACUAAAGU_U UACCAC- -GAUCU
   *        *                 *
```

KH-0008

(SEQ ID NO: 28)
```
  GCUGGUUUCA^U AUGGUG^GU UUAGA
                                K
  UUGUGACUAAAGU_U UACCAC- -GAUCU
   *        *                 *
```

XH-0017

(SEQ ID NO: 28)
```
  GCUGGUUUCA^U AUGGUG^GU UUAGA
                                Gly
  UUGUGACUAAAGU_U UACCAC- -GAUCU
   *        *                 *
```

XH-0019

(SEQ ID NO: 28)
```
  GCUGGUUUCA^U AUGGUG^GU UUAGA
                                GlyGly
  UUGUGACUAAAGU_U UACCAC- -GAUCU
   *        *                 *
```

XH-0021

(SEQ ID NO: 28)

```
GCUGGUUUCA^U AUGGUG^GU UUAGA
                                    TP
UUGUGACUAAAGU_U UACCAC--GAUCU
    *   *                   *
```
spacer

PH-0042

(SEQ ID NO: 29)

```
GCUGGUUUCA^U AUGGUG^GU UUAGAUCC
                                   P
UUGUGACUAAAGU_U UACCAC--GAUCUAGG
    *   *                   *
```

In the aforementioned sequence, an asterisk shows a base non-complementary to the corresponding guide strand. The "spacer" shows that the aforementioned X region contains an additional sequence.

In the following sequence, [P] shows the non-nucleotide structure of the aforementioned proline derivative, [K] shows the non-nucleotide structure of the aforementioned lysine derivative, [Gly] shows the non-nucleotide structure of the aforementioned glycine derivative, [GlyGly] shows the non-nucleotide structure of the aforementioned glycylglycine derivative, and [TP] shows the non-nucleotide structure of the aforementioned terephthalic acid. In the following sequences, the 5'-side region of each linker is X region, and in the aforementioned X region, the lower-case letters show the aforementioned passenger strand sequence, the rest is the aforementioned additional sequence, the 3'-side region of each linker is Y region and, in the aforementioned Y region, the underlined part shows the aforementioned guide strand sequence.

```
PH-0040
                                   (SEQ ID NO: 28)
5'-gcugguuucauauggugguuuaga-[P]-

UCUAGCACCAUUUGAAAUCAGUGUU-3'

KH-0008
                                   (SEQ ID NO: 28)
5'-gcugguuucauauggugguuuaga-[K]-

UCUAGCACCAUUUGAAAUCAGUGUU-3'

XH-0017
                                   (SEQ ID NO: 28)
5'-gcugguuucauauggugguuuaga-[Gly]-

UCUAGCACCAUUUGAAAUCAGUGUU-3'

XH-0019
                                   (SEQ ID NO: 28)
5'-gcugguuucauauggugguuuaga-[GlyGly]-

UCUAGCACCAUUUGAAAUCAGUGUU-3'

XH-0021
                                   (SEQ ID NO: 28)
5'-gcugguuucauauggugguuuaga-[TP]-

UCUAGCACCAUUUGAAAUCAGUGUUE-3'

PH-0042
                                   (SEQ ID NO: 29)
5'-gcugguuucauauggugguuuagaUCC-[P]-

GGAUCUAGCACCAUUUGAAAUCAGUGUU-3'
```

As a negative control, NI-0000 synthesized in Example 1 was used.

(2) Measurement of Expression Level of COL1A1 Gene

Each of the aforementioned RNAs was dissolved in distilled water for injection (Otsuka Pharmaceutical Co., Ltd.) at 2 μmol/L, whereby an RNA solution was prepared.

A549 cells (DS PHARMA BIOMEDICAL) were used as the cell. As the medium, DMEM (Life Technologies) containing 10% FBS was used. The culture conditions were set to 37° C., 5% $CO_2$.

First, the cells were cultured in the aforementioned medium, and the cultured solution was dispensed to a 24-well plate so that each well contained 400 μL of the cultured solution to achieve a density of $4 \times 10^4$ cells/well. The cells were transfected with the aforementioned RNA using (A) transfection reagent Lipofectamine RNAiMAX (Life Technologies) according to the protocol attached to the aforementioned transfection reagent. Specifically, the transfection was carried out by setting the composition per well as follows. In the following composition, (B) is Opti-MEM (Life Technologies), (C) is the aforementioned 2 μmol/L RNA solution, 98.5 μL in total of them was added. The final concentration of the aforementioned RNA in the aforementioned well was set to 1 nmol/L.

TABLE 3

| (composition per well: μL) | |
|---|---|
| cultured solution | 400 |
| transfection reagent | 1.5 |
| (B) + (C) | 98.5 |
| total | 500 |

After the transfection, the cells in the aforementioned wells were cultured for 24 hours, and then, the RNA was collected using an RNeasy Mini Kit (Qiagen, Netherlands) according to the protocol supplied therewith. Subsequently, cDNA was synthesized from the aforementioned RNA by using Transcriptor First Strand cDNA Synthesis Kit (Roche) according to the protocol supplied therewith. Then, as shown below, PCR was carried out using the aforementioned synthesized cDNA as a template, and the expression level of the COL1A1 gene and that of GAPDH gene as an internal standard were measured. The aforementioned expression level of the COL1A1 gene was normalized with reference to that of the GAPDH gene mentioned above.

The aforementioned PCR was carried out using LightCycler 480 SYBR Green I Master (trade name, Roche) as a reagent and LightCycler 480 Instrument II (trade name, Roche) as an instrument (hereinafter the same). The aforementioned COL1A1 and GAPDH genes were amplified using the following primer sets, respectively.

```
PCR primer set for COL1A1 gene
                                   (SEQ ID NO: 30)
5'-CCCAAGGACAAGAGGCATGT-3'

(SEQ ID NO: 31)
5'-CCGCCATACTCGAACTGGAA-3' primer set for GAPDH gene
                                   (SEQ ID NO: 20)
5'-ATGGGGAAGGTGAAGGTCG-3'

(SEQ ID NO: 21)
5'-GGGTCATTGATGGCAACAATATC-3'
```

As control 1, regarding the cells to which 100 μL of the aforementioned solution (B) alone had been added to the aforementioned cultured solution, the expression levels of the genes also were measured (−). Furthermore, as control 2, regarding the cells subjected to the same transfection procedures as in the above except that the aforementioned RNA solution was not added and that the aforementioned (B) and 1.5 μL of the aforementioned (A) were added so that the total amount of (A) and (B) would be 100 μL, the expression level of the gene also was measured (mock).

As for the expression level of normalized COL1A1 gene, the relative value in the cell introduced with each RNA was determined based on the expression level in the cells of the control (−) as 1.

(3) Results

Figure 6:
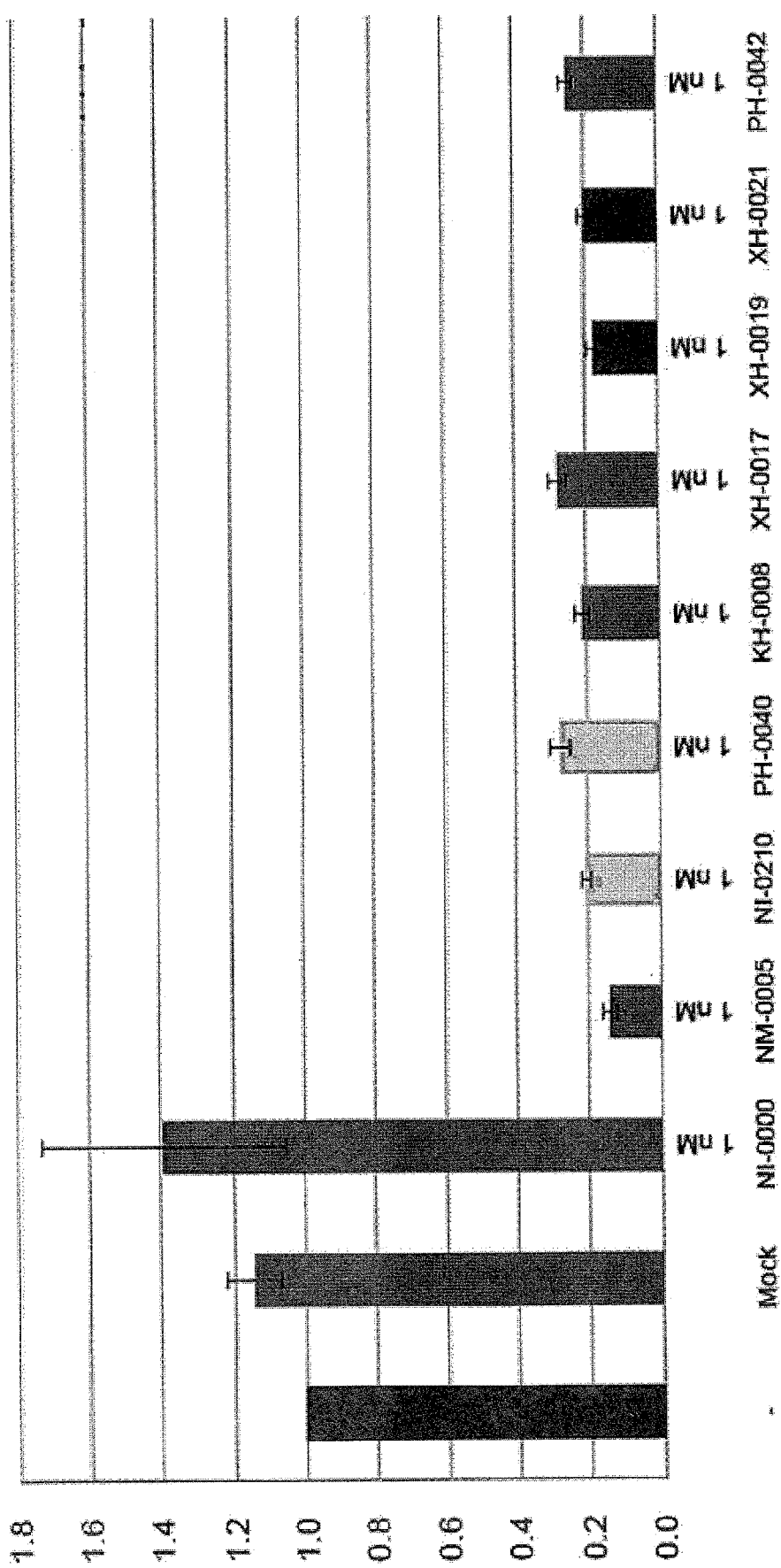
FIG. 6 is a graph showing the relative values of COL1A1 mRNA amount in Example 5.

As shown in FIG. 6, natural type miR-29b of the Example inhibited expression of COL1A1 mRNA at the same level as that by the positive control mature miR-29b and pre-miR-29b variant. In addition, an inhibitory effect on the expression of COL1A1 mRNA was maintained even when the non-nucleotide structure of the linker was altered or the additional sequence was introduction into X region.

Example 6

Based on the sequence information of the guide strand and the passenger strand of mature miR-34a (miRBase Accession No. MI0000268), various natural type miRNAs of the present invention having a different non-nucleotide structure of the linker region and a different base length of the additional sequence in the X region were synthesized, introduced into cultured cells and an inhibitory effect on the expression of the target gene AXL mRNA was examined.

(1) Synthesis of miRNA

By a method similar to that in Example 1, a natural type miR-34a (PH-0036, PH-0038, PH-0066 and PH-0068) wherein X region composed of the guide strand (SEQ ID NO: 1) and an additional sequence (0, 3, 5 or 7 base length), and Y region having, at the 5′-terminus of the passenger strand, an overhang region of the aforementioned guide strand and a sequence completely complementary to the aforementioned additional sequence, are linked via a non-nucleotide structure of a proline derivative, was synthesized.

In addition, of the above-mentioned natural type miR-34a, natural type miR-34a (PH-0036, PH-0038 or PH-0066) having an additional sequence with 0, 3 or 5 base length, wherein the non-nucleotide structure of the linker region is modified by a method similar to that in Example 2, was synthesized.

KH-0006

(SEQ ID NO: 14)

$^U$GGCAGUGU-CUU$^A$GCUGGUUGU
$_{UC}$CCGUCAUA$_U$GAA-CGACUAACA$^K$

KH-0018

(SEQ ID NO: 15)

$^U$GGCAGUGU-CUU$^A$GCUGGUUGUUCC
$_{UC}$CCGUCAUA$_U$GAA-CGACUAACAAGG$^K$

KH-0019

(SEQ ID NO: 16)

$^U$GGCAGUGU-CUU$^A$GCUGGUUGUUCCGG
$_{UC}$CCGUCAUA$_U$GAA-CGACUAACAAGGCC$^K$

XH-0015

(SEQ ID NO: 14)

$^U$GGCAGUGU-CUU$^A$GCUGGUUGU
$_{UC}$CCGUCAUA$_U$GAA-CGACUAACA$^{TP}$

XH-0024

(SEQ ID NO: 15)

$^U$GGCAGUGU-CUU$^A$GCUGGUUGUUCC
$_{UC}$CCGUCAUA$_U$GAA-CGACUAACAAGG$^{TP}$

XH-0042

(SEQ ID NO: 16)

$^U$GGCAGUGU-CUU$^A$GCUGGUUGUUCCGG
$_{UC}$CCGUCAUA$_U$GAA-CGACUAACAAGGCC$^{TP}$

XH-0011

(SEQ ID NO: 14)

$^U$GGCAGUGU-CUU$^A$GCUGGUUGU
$_{UC}$CCGUCAUA$_U$GAA-CGACUAACA$^{Gly}$

XH-0043

(SEQ ID NO: 15)

$^U$GGCAGUGU-CUU$^A$GCUGGUUGUUCC
$_{UC}$CCGUCAUA$_U$GAA-CGACUAACAAGG$^{Gly}$

XH-0044

(SEQ ID NO: 16)

$^U$GGCAGUGU-CUU$^A$GCUGGUUGUUCCGG
$_{UC}$CCGUCAUA$_U$GAA-CGACUAACAAGGCC$^{Gly}$

XH-0013

(SEQ ID NO: 14)

$^U$GGCAGUGU-CUU$^A$GCUGGUUGU
$_{UC}$CCGUCAUA$_U$GAA-CGACUAACA$^{GlyGly}$

XH-0045

(SEQ ID NO: 15)

$^U$GGCAGUGU-CUU$^A$GCUGGUUGUUCC
$_{UC}$CCGUCAUA$_U$GAA-CGACUAACAAGG$^{GlyGly}$

XH-0046

(SEQ ID NO: 16)

$^U$GGCAGUGU-CUU$^A$GCUGGUUGUUCCGG
$_{UC}$CCGUCAUA$_U$GAA-CGACUAACAAGGCC$^{GlyGly}$

In the following sequence, [K] shows a non-nucleotide structure of the lysine derivative, [TP] shows a non-nucleotide structure of the terephthalic acid derivative, [Gly] shows a non-nucleotide structure of the glycine derivative, and [GlyGly] shows a non-nucleotide structure of the glycylglycine derivative. In the following sequences, the 5′-side region of each linker is X region, and in the aforementioned X region, the underlined part is the guide strand sequence, the rest is the aforementioned additional sequence, and the 3′-side region of each linker is Y region and, in the aforementioned Y region, lower-case letters show a passenger strand sequence.

KH-0006

(SEQ ID NO: 14)

5′-<u>UGGCAGUGUCUUAGCUGGUUGU</u>-[K]-

Acaaucagcaaguauacugcccu-3′

-continued

KH-0018
(SEQ ID NO: 15)
5'-<u>UGGCAGUGUCUUAGCUGGUUGUU</u>CC-[K]-
GGAAcaaucagcaaguauacugcccu-3'

KH-0019
(SEQ ID NO: 16)
5'-<u>UGGCAGUGUCUUAGCUGGUUGUU</u>CCGG-[K]-
CCGGAAcaaucagcaaguauacugcccu-3'

XH-0015
(SEQ ID NO: 14)
5'-<u>UGGCAGUGUCUUAGCUGGUUGU</u>-[TP]-
Acaaucagcaaguauacugcccu-3'

XH-0024
(SEQ ID NO: 15)
5'-<u>UGGCAGUGUCUUAGCUGGUUGU</u>CC-[TP]-
GGAAcaaucagcaaguauacugcccu-3'

XH-0042
(SEQ ID NO: 16)
5'-<u>UGGCAGUGUCUUAGCUGGUUGU</u>CCGG-[TP]-
CCGGAAcaaucagcaaguauacugcccu-3'

XH-0011
(SEQ ID NO: 14)
5'-<u>UGGCAGUGUCUUAGCUGGUUGU</u>-[Gly]-
Acaaucagcaaguauacugcccu-3'

XH-0043
(SEQ ID NO: 15)
5'-<u>UGGCAGUGUCUUAGCUGGUUGU</u>CC-[Gly]-
GGAAcaaucagcaaguauacugcccu-3'

XH-0044
(SEQ ID NO: 16)
5'-<u>UGGCAGUGUCUUAGCUGGUUGU</u>CCGG-[Gly]-
CCGGAAcaaucagcaaguauacugcccu-3'

XH-0013
(SEQ ID NO: 14)
5'-<u>UGGCAGUGUCUUAGCUGGUUGU</u>-[GlyGly]-
Acaaucagcaaguauacugcccu-3'

XH-0045
(SEQ ID NO: 15)
5'-<u>UGGCAGUGUCUUAGCUGGUUGU</u>CC-[GlyGly]-
GGAAcaaucagcaaguauacugcccu-3'

XH-0046
(SEQ ID NO: 16)
5'-<u>UGGCAGUGUCUUAGCUGGUUGU</u>CCGG-[GlyGly]-
CCGGAAcaaucagcaaguauacugcccu-3'

As a positive control, NI-0208 of Example 1 was used.

(2) Measurement of Expression Level of AXL Gene

By a method similar to that in Example 1 except that the final concentration of the aforementioned each RNA was 2 nmol/L, the expression level of AXL gene was determined.

(3) Results

Figure 7:
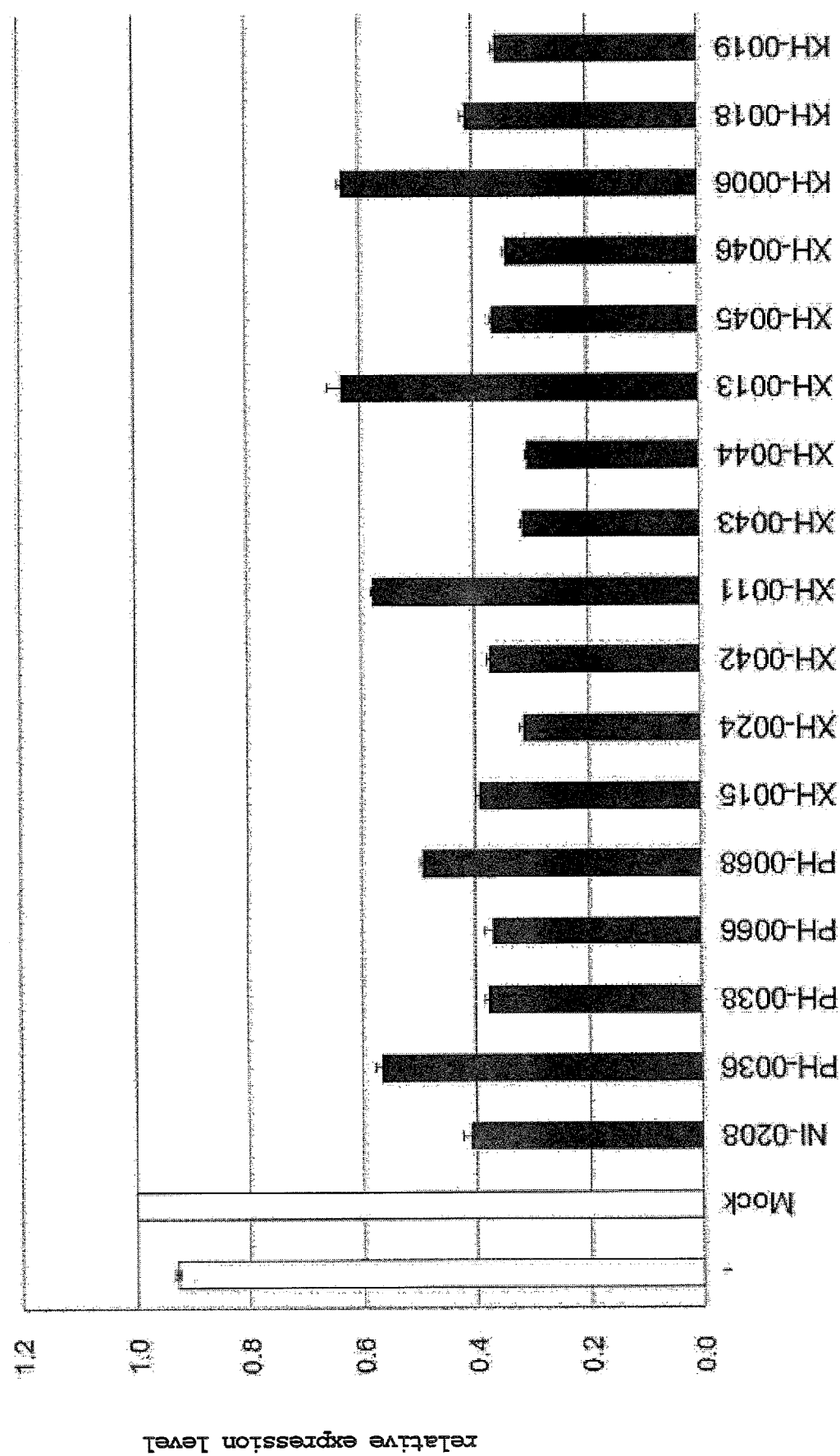
FIG. 7 is a graph showing the relative values of AXL mRNA amount in Example 6.

As shown in FIG. 7, natural type miR-34a of the Example inhibited expression of AXL mRNA at the same level as that by the positive control miR-34a variant. In addition, an inhibitory effect on the expression of AXL mRNA was maintained even when the non-nucleotide structure of the linker was altered or the additional sequence was introduction into X region.

Example 7

Based on the sequence information of the guide strand and the passenger strand of mature let-7a (miRBase Accession No. MI0000060), various natural type miRNAs of the present invention having a different non-nucleotide structure of the linker region and a different base length of the additional sequence in the X region were synthesized, introduced into cultured cells and an inhibitory effect on the expression of the target gene HMGA2 mRNA was examined.

(1) Synthesis of miRNA

By a method similar to that in Example 4, various natural type let-7a wherein X region composed of the guide strand (SEQ ID NO: 3) and an additional sequence (0, 3 or 5 base length), and Y region having, at the 5'-terminus of the passenger strand, an overhang region of the aforementioned guide strand and a sequence completely complementary to the aforementioned additional sequence, are linked via a linker of proline derivative ([P]), lysine derivative ([K]), terephthalic acid derivative ([TP]), glycine derivative ([Gly]) or glycylglycine derivative ([GlyGly]) were synthesized. In the aforementioned synthesis of the natural type miRNA, each non-nucleotide structure was introduced in the same manner as in Examples 1 and 2.

PH-0011
(SEQ ID NO: 23)

$$\begin{array}{c} \phantom{CU}U\phantom{UUC}\phantom{UG}GU\phantom{UCAUCUAACAUAUCAA} \\ \phantom{CU-UUC}GAG\phantom{UG}AGUAGGUUGUAUAGUU_P \\ CU\text{-}UUC\phantom{GAG}UCAUCUAACAUAUCAA \\ \phantom{CU\text{-}UUC}UG \end{array}$$

PH-0014
(SEQ ID NO: 24)

$$\begin{array}{c} U\phantom{GAG}GU \\ \phantom{CU}GAG\phantom{UG}AGUAGGUUGUAUAGUUCC_P \\ CU\text{-}UUC\phantom{GAG}UCAUCUAACAUAUCAAAGG \\ \phantom{CU\text{-}UUC}UG \end{array}$$

PH-0107
(SEQ ID NO: 32)

$$\begin{array}{c} U\phantom{GAG}GU \\ \phantom{CU}GAG\phantom{UG}AGUAGGUUGUAUAGUUCCGG_P \\ CU\text{-}UUC\phantom{GAG}UCAUCUAACAUAUCAAAGGCC \\ \phantom{CU\text{-}UUC}UG \end{array}$$

KH-0003
(SEQ ID NO: 23)

$$\begin{array}{c} U\phantom{GAG}GU \\ \phantom{CU}GAG\phantom{UG}AGUAGGUUGUAUAGUU_K \\ CU\text{-}UUC\phantom{GAG}UCAUCUAACAUAUCAA \\ \phantom{CU\text{-}UUC}UG \end{array}$$

KH-0020
(SEQ ID NO: 24)

$$\begin{array}{c} U\phantom{GAG}GU \\ \phantom{CU}GAG\phantom{UG}AGUAGGUUGUAUAGUUCC_K \\ CU\text{-}UUC\phantom{GAG}UCAUCUAACAUAUCAAAGG \\ \phantom{CU\text{-}UUC}UG \end{array}$$

KH-0021
(SEQ ID NO: 32)

$$\begin{array}{c} U\phantom{GAG}GU \\ \phantom{CU}GAG\phantom{UG}AGUAGGUUGUAUAGUUCCGG_K \\ CU\text{-}UUC\phantom{GAG}UCAUCUAACAUAUCAAAGGCC \\ \phantom{CU\text{-}UUC}UG \end{array}$$

XH-0002

(SEQ ID NO: 23)
```
  U    GU
 GAG      AGUAGGUUGUAUAGUU
CU-UUC   UCAUCUAACAUAUCAA   Gly
   UG
```

XH-0049

(SEQ ID NO: 24)
```
  U    GU
 GAG      AGUAGGUUGUAUAGUUUCC
CU-UUC   UCAUCUAACAUAUCAAAGG   Gly
   UG
```

XH-0050

(SEQ ID NO: 32)
```
  U    GU
 GAG      AGUAGGUUGUAUAGUUUCCGG
CU-UUC   UCAUCUAACAUAUCAAAGGCC   Gly
   UG
```

XH-0006

(SEQ ID NO: 23)
```
  U    GU
 GAG      AGUAGGUUGUAUAGUU
CU-UUC   UCAUCUAACAUAUCAA   TP
   UG
```

XH-0047

(SEQ ID NO: 24)
```
  U    GU
 GAG      AGUAGGUUGUAUAGUUUCC
CU-UUC   UCAUCUAACAUAUCAAAGG   TP
   UG
```

XH-0048

(SEQ ID NO: 32)
```
  U    GU
 GAG      AGUAGGUUGUAUAGUUUCCGG
CU-UUC   UCAUCUAACAUAUCAAAGGCC   TP
   UG
```

XH-0004

(SEQ ID NO: 23)
```
  U    GU
 GAG      AGUAGGUUGUAUAGUU
CU-UUC   UCAUCUAACAUAUCAA   GlyGly
   UG
```

XH-0051

(SEQ ID NO: 24)
```
  U    GU
 GAG      AGUAGGUUGUAUAGUUUCC
CU-UUC   UCAUCUAACAUAUCAAAGG   GlyGly
   UG
```

XH-0052

(SEQ ID NO: 32)
```
  U    GU
 GAG      AGUAGGUUGUAUAGUUUCCGG
CU-UUC   UCAUCUAACAUAUCAAAGGCC   GlyGly
   UG
```

In the following sequence, [P] shows a non-nucleotide structure of the proline derivative, [K] shows a non-nucleotide structure of the lysine derivative, [TP] shows a non-nucleotide structure of the terephthalic acid derivative, [Gly] shows a non-nucleotide structure of the glycine derivative, and [GlyGly] shows a non-nucleotide structure of the glycylglycine derivative. In the following sequences, the 5'-side region of each linker is X region, and in the aforementioned X region, the underlined part is the aforementioned guide strand sequence, the rest is the aforementioned additional sequence, and the 3'-side region of each linker is Y region, and in the aforementioned Y region, the lower-case letters show the aforementioned passenger strand sequence.

PH-0011

(SEQ ID NO: 23)
5'-UGAGGUAGUAGGUUGUAUAGUU-[P]-AAcuauacaaucuacugucuuuc-3'

PH-0014

(SEQ ID NO: 24)
5'-UGAGGUAGUAGGUUGUAUAGUUCC-[P]-GGAAAcuauacaaucuacugucuuuc-3'

PH-0107

(SEQ ID NO: 32)
5'-UGAGGUAGUAGGUUGUAUAGUUUCCGG-[P]-CCGGAAAcuauacaaucuacugucuuuc-3'

KH-0003

(SEQ ID NO: 23)
5'-UGAGGUAGUAGGUUGUAUAGUU-[K]-AAcuauacaaucuacugucuuuc-3'

KH-0020

(SEQ ID NO: 24)
5'-UGAGGUAGUAGGUUGUAUAGUUCC-[K]-GGAAAcuauacaaucuacugucuuuc-3'

KH-0021

(SEQ ID NO: 32)
5'-UGAGGUAGUAGGUUGUAUAGUUUCCGG-[K]-CCGGAAAcuauacaaucuacugucuuuc-3'

XH-0006

(SEQ ID NO: 23)
5'-UGAGGUAGUAGGUUGUAUAGUU-[TP]-AAcuauacaaucuacugucuuuc-3'

XH-0047

(SEQ ID NO: 24)
5'-UGAGGUAGUAGGUUGUAUAGUUCC-[TP]-GGAAAcuauacaaucuacugucuuuc-3'

XH-0048

(SEQ ID NO: 32)
5'-UGAGGUAGUAGGUUGUAUAGUUUCCGG-[TP]-CCGGAAAcuauacaaucuacugucuuuc-3'

XH-0002

(SEQ ID NO: 23)
5'-UGAGGUAGUAGGUUGUAUAGUU-[Gly]-AAcuauacaaucuacugucuuuc-3'

XH-0049

(SEQ ID NO: 24)
5'-UGAGGUAGUAGGUUGUAUAGUUCC-[Gly]-GGAAAcuauacaaucuacugucuuuc-3'

XH-0050

(SEQ ID NO: 32)
5'-UGAGGUAGUAGGUUGUAUAGUUUCCGG-[Gly]-CCGGAAAcuauacaaucuacugucuuuc-3'

XH-0004

(SEQ ID NO: 23)
5'-UGAGGUAGUAGGUUGUAUAGUU-[GlyGly]-AAcuauacaaucuacugucuuuc-3'

-continued

XH-0051
(SEQ ID NO: 24)
5'-UGAGGUAGUAGGUUGUAUAGUUUCC-[GlyGly]-
GGAAAcuauacaaucuacugucuuuc-3'

XH-0052
(SEQ ID NO: 32)
5'-UGAGGUAGUAGGUUGUAUAGUUUCCGG-[GlyGly]-
CCGGAAAcuauacaaucuacugucuuuc-3'

Figure 8:
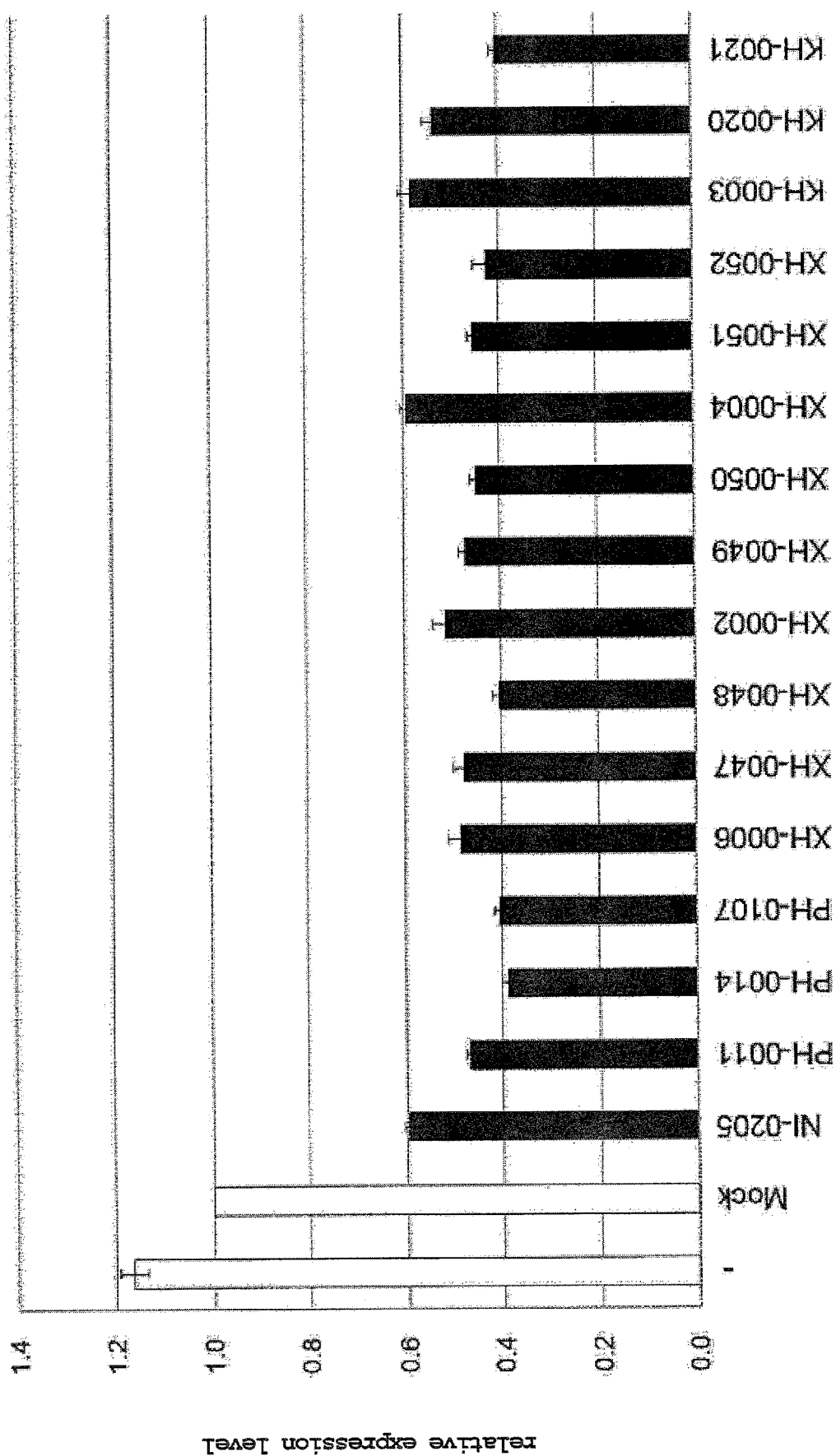
FIG. 8 is a graph showing the relative values of HMGA2 mRNA amount in Example 7.

As a positive control, NI-0205 of Example 4 was used.
(2) Measurement of Expression Level of HMGA2 Gene By a method similar to that in Example 4 except that the cell into which the aforementioned each RNA is introduced is HepG2 (ATCC), and the final concentration of the aforementioned each RNA was 0.2 nmol/L, the expression level of HMGA2 gene was determined.
(3) Results As shown in FIG. 8, natural type let-7a of the Example inhibited expression of HMGA2 mRNA at the same level as that by the positive control pre-let-7a variant. In addition, an inhibitory effect on the expression of HMGA2 mRNA was maintained even when the non-nucleotide structure of the linker was altered or the additional sequence was introduction into X region.

Example 8

Based on the sequence information of the guide strand and the passenger strand of mature miR-29b (miRBase Accession No. MI0000105), various natural type miRNAs of the present invention having a different non-nucleotide structure of the linker region and a different base length of the additional sequence in the X region were synthesized, introduced into cultured cells and an inhibitory effect on the expression of the target gene COL1A1 mRNA was examined.
(1) Synthesis of miRNA By a method similar to that in Example 5, various natural type miR-29b wherein X region composed of the passenger strand (SEQ ID NO: 10) and an additional sequence (0, 3 or 5 base length), and Y region having, at the 5'-terminus of the guide strand, an overhang region of the aforementioned passenger strand and a sequence completely complementary to the aforementioned additional sequence, are linked via a linker of proline derivative ([P]), lysine derivative ([K]), terephthalic acid derivative ([TP]), glycine derivative ([Gly]) or glycylglycine derivative ([GlyGly]) were synthesized. In the aforementioned synthesis of the natural type miRNA, each non-nucleotide structure was introduced in the same manner as in Examples 1 and 2.

PH-0040
(SEQ ID NO: 28)
GCUGGUUUCA<sup>U</sup>AUGGUG<sup>GU</sup>UUAGA<sub>P</sub>
UUGUGACUAAAGU<sub>U</sub>UACCAC--GAUCU PH-0042
(SEQ ID NO: 29)
GCUGGUUUCA<sup>U</sup>AUGGUG<sup>GU</sup>UUAGAUCC<sub>P</sub>
UUGUGACUAAAGU<sub>U</sub>UACCAC--GAUCUAGG PH-0108
(SEQ ID NO: 33)
GCUGGUUUCA<sup>U</sup>AUGGUG<sup>GU</sup>UUAGAUCCGG<sub>P</sub>
UUGUGACUAAAGU<sub>U</sub>UACCAC--GAUCUAGGCC KH-0008
(SEQ ID NO: 28)
GCUGGUUUCA<sup>U</sup>AUGGUG<sup>GU</sup>UUAGA<sub>K</sub>
UUGUGACUAAAGU<sub>U</sub>UACCAC--GAUCU PH-0022
(SEQ ID NO: 29)
GCUGGUUUCA<sup>U</sup>AUGGUG<sup>GU</sup>UUAGAUCC<sub>K</sub>
UUGUGACUAAAGU<sub>U</sub>UACCAC--GAUCUAGG PH-0023
(SEQ ID NO: 33)
GCUGGUUUCA<sup>U</sup>AUGGUG<sup>GU</sup>UUAGAUCCGG<sub>K</sub>
UUGUGACUAAAGU<sub>U</sub>UACCAC--GAUCUAGGCC XH-0021
(SEQ ID NO: 28)
GCUGGUUUCA<sup>U</sup>AUGGUG<sup>GU</sup>UUAGA<sub>TP</sub>
UUGUGACUAAAGU<sub>U</sub>UACCAC--GAUCU PH-0053
(SEQ ID NO: 29)
GCUGGUUUCA<sup>U</sup>AUGGUG<sup>GU</sup>UUAGAUCC<sub>TP</sub>
UUGUGACUAAAGU<sub>U</sub>UACCAC--GAUCUAGG PH-0054
(SEQ ID NO: 33)
GCUGGUUUCA<sup>U</sup>AUGGUG<sup>GU</sup>UUAGAUCCGG<sub>TP</sub>
UUGUGACUAAAGU<sub>U</sub>UACCAC--GAUCUAGGCC XH-0017
(SEQ ID NO: 28)
GCUGGUUUCA<sup>U</sup>AUGGUG<sup>GU</sup>UUAGA<sub>Gly</sub>
UUGUGACUAAAGU<sub>U</sub>UACCAC--GAUCU PH-0055
(SEQ ID NO: 29)
GCUGGUUUCA<sup>U</sup>AUGGUG<sup>GU</sup>UUAGAUCC<sub>Gly</sub>
UUGUGACUAAAGU<sub>U</sub>UACCAC--GAUCUAGG PH-0056
(SEQ ID NO: 33)
GCUGGUUUCA<sup>U</sup>AUGGUG<sup>GU</sup>UUAGAUCCGG<sub>Gly</sub>
UUGUGACUAAAGU<sub>U</sub>UACCAC--GAUCUAGGCC XH-0019
(SEQ ID NO: 28)
GCUGGUUUCA<sup>U</sup>AUGGUG<sup>GU</sup>UUAGA<sub>GlyGly</sub>
UUGUGACUAAAGU<sub>U</sub>UACCAC--GAUCU PH-0057
(SEQ ID NO: 29)
GCUGGUUUCA<sup>U</sup>AUGGUG<sup>GU</sup>UUAGAUCC<sub>GlyGly</sub>
UUGUGACUAAAGU<sub>U</sub>UACCAC--GAUCUAGG

PH-0058

(SEQ ID NO: 33)

GCUGGUUUCA$^U$AUGGUG$^{GU}$UUAGAUCCGG
UUGUGACUAAAGU$_U$UACCAC--GAUCUAGGCC$_{GlyGly}$

In the following sequence, [P] shows a non-nucleotide structure of the proline derivative, [K] shows a non-nucleotide structure of the lysine derivative, [TP] shows a non-nucleotide structure of the terephthalic acid derivative, [Gly] shows a non-nucleotide structure of the glycine derivative, and [GlyGly] shows a non-nucleotide structure of the glycylglycine derivative. In the following sequences, the 5'-side region of each linker is X region, and in the aforementioned X region, the lower-case letters show the aforementioned passenger strand sequence, the rest is the aforementioned additional sequence, and the 3'-side region of each linker is Y region, and in the aforementioned Y region, the underlined part is the aforementioned guide strand sequence.

PH-0040

(SEQ ID NO: 28)
5'-gcugguuucauauggugguuuaga-[P]-
U<u>CUAGCACCAUUUGAAAUCAGUGUU</u>-3'

PH-0042

(SEQ ID NO: 29)
5'-gcugguuucauauggugguuuagaUCC-[P]-
GGAU<u>CUAGCACCAUUUGAAAUCAGUGUU</u>-3'

PH-0108

(SEQ ID NO: 33)
5'-gcugguuucauauggugguuuagaUCCGG-[P]-
CCGGAU<u>CUAGCACCAUUUGAAAUCAGUGUU</u>-3'

KH-0008

(SEQ ID NO: 28)
5'-gcugguuucauauggugguuuaga-[K]-
U<u>CUAGCACCAUUUGAAAUCAGUGUU</u>-3'

KH-0022

(SEQ ID NO: 29)
5'-gcugguuucauauggugguuuagaUCC-[K]-
GGAU<u>CUAGCACCAUUUGAAAUCAGUGUU</u>-3'

KH-0023

(SEQ ID NO: 33)
5'-gcugguuucauauggugguuuagaUCCGG-[K]-
CCGGAU<u>CUAGCACCAUUUGAAAUCAGUGUU</u>-3'

XH-0021

(SEQ ID NO: 28)
5'-gcugguuucauauggugguuuaga-[TP]-
U<u>CUAGCACCAUUUGAAAUCAGUGUU</u>-3'

XH-0053

(SEQ ID NO: 29)
5'-gcugguuucauauggugguuuagaUCC-[TP]-
GGAU<u>CUAGCACCAUUUGAAAUCAGUGUU</u>-3'

XH-0054

(SEQ ID NO: 33)
5'-gcugguuucauauggugguuuagaUCCGG-[TP]-
CCGGAU<u>CUAGCACCAUUUGAAAUCAGUGUU</u>-3'

XH-0017

(SEQ ID NO: 28)
5'-gcugguuucauauggugguuuaga-[Gly]-
U<u>CUAGCACCAUUUGAAAUCAGUGUU</u>-3'

XH-0055

(SEQ ID NO: 29)
5'-gcugguuucauauggugguuuagaUCC-[Gly]-
GGAU<u>CUAGCACCAUUUGAAAUCAGUGUU</u>-3'

XH-0056

(SEQ ID NO: 33)
5'-gcugguuucauauggugguuuagaUCCGG-[Gly]-
CCGGAU<u>CUAGCACCAUUUGAAAUCAGUGUU</u>-3'

XH-0019

(SEQ ID NO: 28)
5'-gcugguuucauauggugguuuaga-[GlyGly]-
U<u>CUAGCACCAUUUGAAAUCAGUGUU</u>-3'

XH-0057

(SEQ ID NO: 29)
5'-gcugguuucauauggugguuuagaUCC-[GlyGly]-
GGAU<u>CUAGCACCAUUUGAAAUCAGUGUU</u>-3'

XH-0058

(SEQ ID NO: 33)
5'-gcugguuucauauggugguuuagaUCCGG-[GlyGly]-
CCGGAU<u>CUAGCACCAUUUGAAAUCAGUGUU</u>-3'

As a positive control, NI-0210 of Example 5 was used.

(2) Measurement of Expression Level of COL1A1 Gene

By a method similar to that in Example 5 except that the final concentration of the aforementioned each RNA was 0.5 nmol/L, the expression level of COL1A1 gene was determined.

(3) Results

Figure 9:
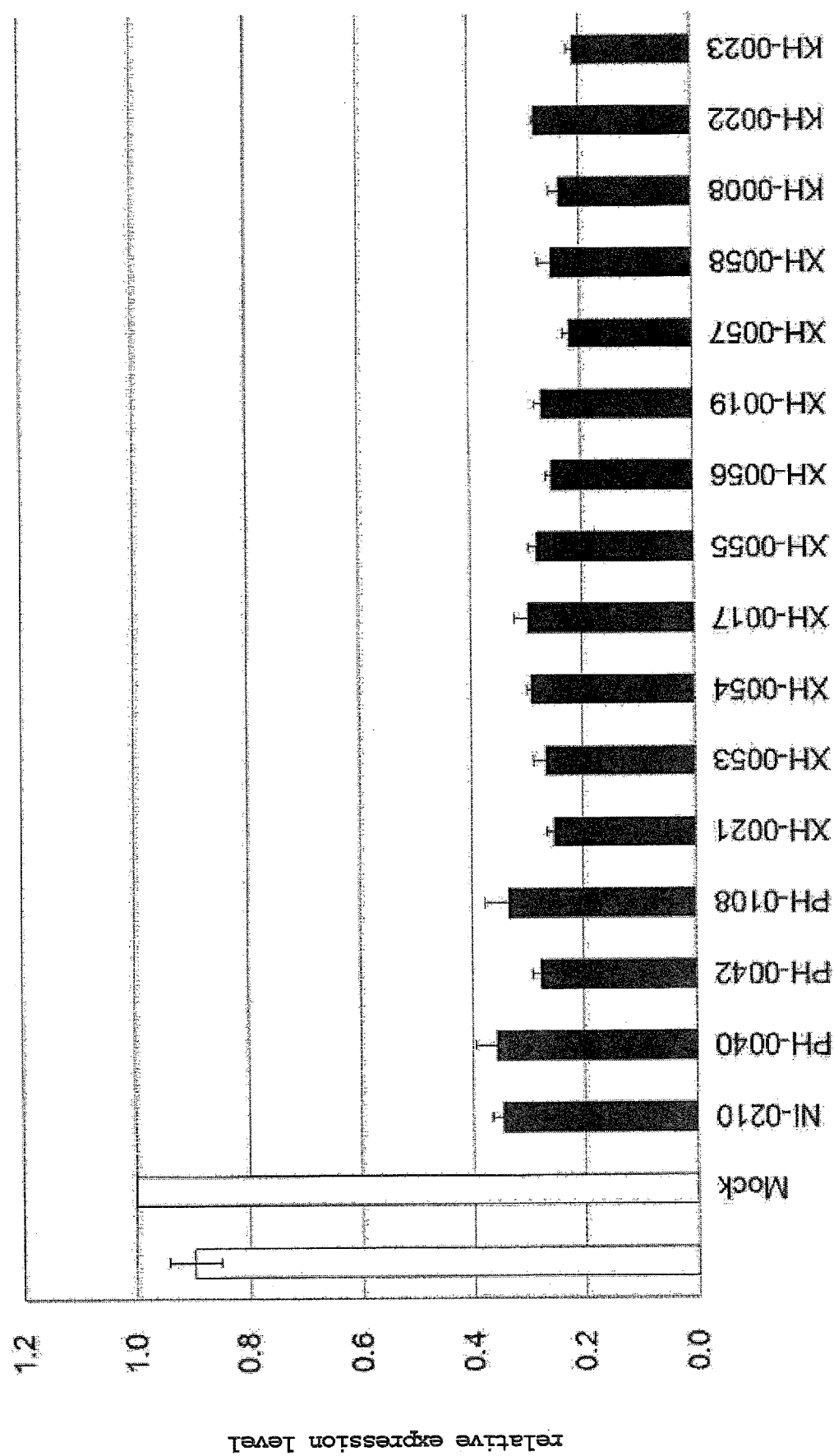
FIG. 9 is a graph showing the relative values of COL1A1 mRNA amount in Example 8.

As shown in FIG. 9, natural type miR-29b of the Example inhibited expression of COL1A1 mRNA at the same level as that by the positive control pre-miR-29b variant. In addition, an inhibitory effect on the expression of COL1A1 mRNA was maintained even when the non-nucleotide structure of the linker was altered or the additional sequence was introduction into X region.

Example 9

Based on the sequence information of the guide strand and the passenger strand of mature miR-34a (miRBase Accession No. MI0000268), various natural type miRNAs of the present invention having a different base sequence of the additional sequence (0, 3, 5 or 7 base length) in the X region were synthesized, introduced into cultured cells and an inhibitory effect on the expression of the target gene AXL mRNA was examined.

(1) Synthesis of miRNA

By a method similar to that in Example 1, a natural type miR-34a wherein X region composed of the guide strand (SEQ ID NO: 1) and an additional sequence (0, 3, 5 or 7 base length), and Y region having, at the 5'-terminus of the passenger strand, an overhang region of the aforementioned guide strand and a sequence complementary (sequence completely complementary or partially complementary) to the aforementioned additional sequence, are linked via a non-nucleotide structure of a proline derivative, was synthesized.

PH-0036

(SEQ ID NO: 14)

$^U$GGCAGUGU-CUU$^A$GCUGGUUGU$_P$
$_{UC}$CCGUCAUA$_U$GAA-CGACUAACA
  \*      \*        \* spacer 3

PH-0038

(SEQ ID NO: 15)

$^U$GGCAGUGU-CUU$^A$GCUGGUUGUUCC$_P$
$_{UC}$CCGUCAUA$_U$GAA-CGACUAACAAGG
  \*      \*        \*

PH-0058

(SEQ ID NO: 34)

$^U$GGCAGUGU-CUU$^A$GCUGGUUGUUAA$_P$
$_{UC}$CCGUCAUA$_U$GAA-CGACUAACAAUU
  \*      \*        \*

PH-0059

(SEQ ID NO: 35)

$^U$GGCAGUGU-CUU$^A$GCUGGUUGUUGG$_P$
$_{UC}$CCGUCAUA$_U$GAA-CGACUAACAAUU
  \*      \*        \*

PH-0060

(SEQ ID NO: 36)

$^U$GGCAGUGU-CUU$^A$GCUGGUUGUCGG$_P$
$_{UC}$CCGUCAUA$_U$GAA-CGACUAACAGCC
  \*      \*        \*

PH-0061

(SEQ ID NO: 37)

$^U$GGCAGUGU-CUU$^A$GCUGGUUGUCAA$_P$
$_{UC}$CCGUCAUA$_U$GAA-CGACUAACAGUU
  \*      \*        \*

PH-0062

(SEQ ID NO: 38)

$^U$GGCAGUGU-CUU$^A$GCUGGUUGUCGG$_P$
$_{UC}$CCGUCAUA$_U$GAA-CGACUAACAGUU
  \*      \*        \*

PH-0063

(SEQ ID NO: 39)

$^U$GGCAGUGU-CUU$^A$GCUGGUUGUUGG$_P$
$_{UC}$CCGUCAUA$_U$GAA-CGACUAACAGCC
  \*      \*        \*

PH-0064

(SEQ ID NO: 40)

$^U$GGCAGUGU-CUU$^A$GCUGGUUGUUAA$_P$
$_{UC}$CCGUCAUA$_U$GAA-CGACUAACAGUU
  \*      \*        \*

PH-0065

(SEQ ID NO: 41)

$^U$GGCAGUGU-CUU$^A$GCUGGUUGUUGG$_P$
$_{UC}$CCGUCAUA$_U$GAA-CGACUAACAGUU
  \*      \*        \* spacer 5

PH-0066

(SEQ ID NO: 16)

$^U$GGCAGUGU-CUU$^A$GCUGGUUGUUCCGG$_P$
$_{UC}$CCGUCAUA$_U$GAA-CGACUAACAAGGCC
  \*      \*        \*

PH-0067

(SEQ ID NO: 42)

$^U$GGCAGUGU-CUU$^A$GCUGGUUGUUAAUU$_P$
$_{UC}$CCGUCAUA$_U$GAA-CGACUAACAAUUAA
  \*      \*        \* spacer 7

PH-0068

(SEQ ID NO: 17)

$^U$GGCAGUGU-CUU$^A$GCUGGUUGUUCCGGCC$_P$
$_{UC}$CCGUCAUA$_U$GAA-CGACUAACAAGGCCGG
  \*      \*        \*

PH-0069

(SEQ ID NO: 43)

$^U$GGCAGUGU-CUU$^A$GCUGGUUGUUAAUUAA$_P$
$_{UC}$CCGUCAUA$_U$GAA-CGACUAACAAUUAAUU
  \*      \*        \*

In the aforementioned sequence, an asterisk shows a base non-complementary to the corresponding guide strand. The number after the "spacer" shows the base length of the additional sequence of the aforementioned X region.

In the following sequence, the underlined part is the aforementioned guide strand sequence, and the lower-case letters show the aforementioned passenger strand sequence. [P] shows a non-nucleotide structure of the aforementioned proline derivative.

PH-0036

(SEQ ID NO: 14)

5'-<u>UGGCAGUGUCUUAGCUGGUUGU</u>-[P]-Acaaucagcaaguauacugcccu-3'

PH-0038

(SEQ ID NO: 15)

5'-<u>UGGCAGUGUCUUAGCUGGUUGUUCC</u>-[P]-GGAAcaaucagcaaguauacugcccu-3'

PH-0058

(SEQ ID NO: 34)

5'-<u>UGGCAGUGUCUUAGCUGGUUGUUAA</u>-[P]-UUAAcaaucagcaaguauacugcccu-3'

PH-0059

(SEQ ID NO: 35)

5'-<u>UGGCAGUGUCUUAGCUGGUUGUUGG</u>-[P]-UUAAcaaucagcaaguauacugcccu-3'

PH-0060

(SEQ ID NO: 36)

5'-<u>UGGCAGUGUCUUAGCUGGUUGUCGG</u>-[P]-CCGAcaaucagcaaguauacugcccu-3'

PH-0061

(SEQ ID NO: 37)

5'-<u>UGGCAGUGUCUUAGCUGGUUGUCAA</u>-[P]-UUGAcaaucagcaaguauacugcccu-3'

-continued

PH-0062

(SEQ ID NO: 38)

5'-UGGCAGUGUCUUAGCUGGUUGUCGG-[P]-

UUGAcaaucagcaaguauacugcccu-3'

PH-0063

(SEQ ID NO: 39)

5'-UGGCAGUGUCUUAGCUGGUUGUUGG-[P]-

CCGAcaaucagcaaguauacugcccu-3'

PH-0064

(SEQ ID NO: 40)

5'-UGGCAGUGUCUUAGCUGGUUGUUAA-[P]-

UUGAcaaucagcaaguauacugcccu-3'

PH-0065

(SEQ ID NO: 41)

5'-UGGCAGUGUCUUAGCUGGUUGUUGG-[P]-

UUGAcaaucagcaaguauacugcccu-3'

PH-0066

(SEQ ID NO: 16)

5'-UGGCAGUGUCUUAGCUGGUUGUUCGG-[P]-

CCGGAAcaaucagcaaguauacugcccu-3'

PH-0067

(SEQ ID NO: 42)

5'-UGGCAGUGUCUUAGCUGGUUGUUAAUU-[P]-

AAUUAAcaaucagcaaguauacugcccu-3'

PH-0068

(SEQ ID NO: 17)

5'-UGGCAGUGUCUUAGCUGGUUGUUCCGGCC-[P]-

GGCCGGAAcaaucagcaaguauacugcccu-3'

PH-0069

(SEQ ID NO: 43)

5'-UGGCAGUGUCUUAGCUGGUUGUUAAUUAA-[P]-

UUAAUUAAcaaucagcaaguauacugcccu-3'

As a positive control, NI-0208 of Example 1 was used.

(2) Measurement of Expression Level of AXL Gene

By a method similar to that in Example 1, and the expression level of AXL gene was determined.

(3) Results

Figure 10:
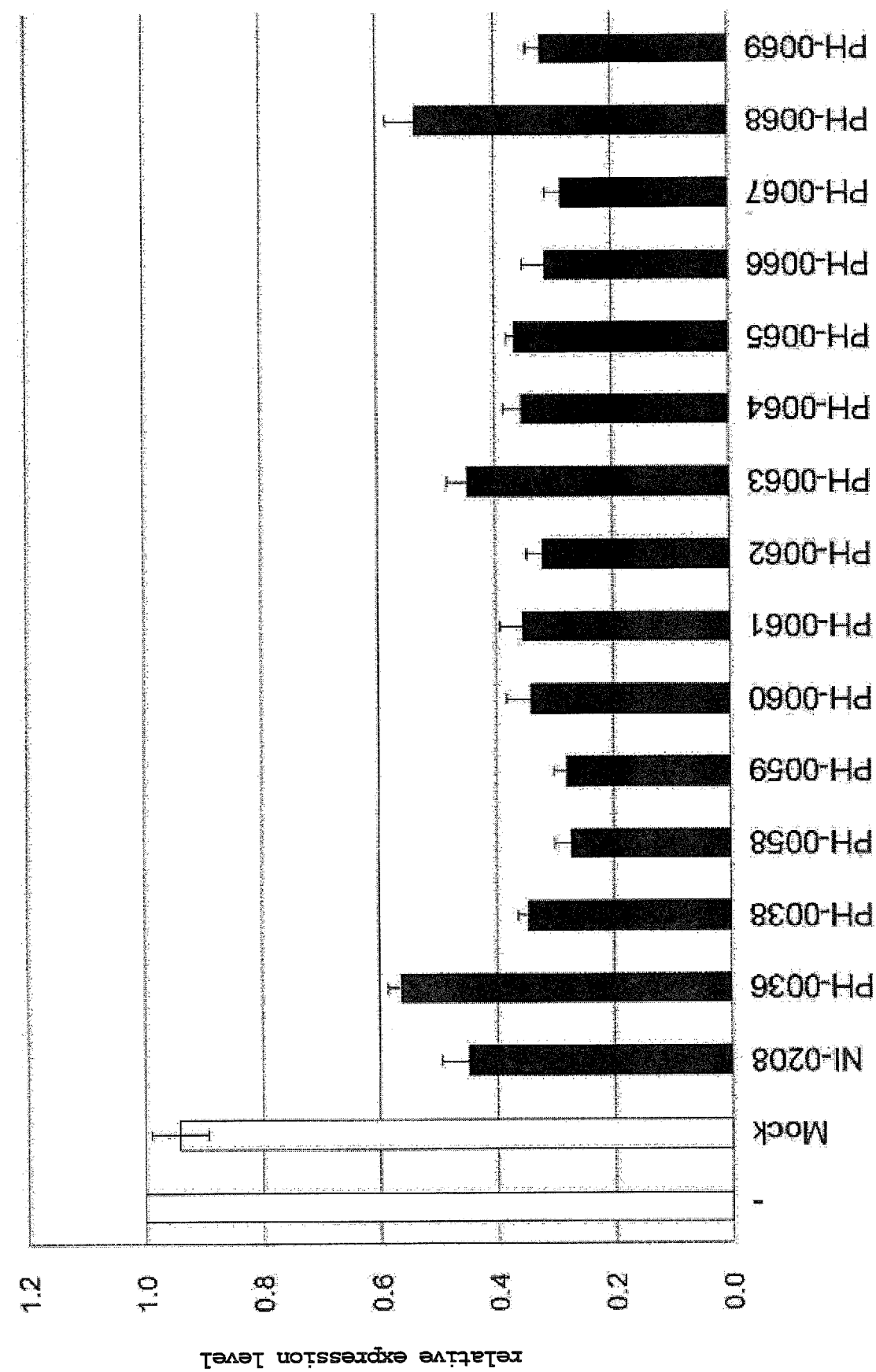
FIG. 10 is a graph showing the relative values of AXL mRNA amount in Example 9.

As shown in FIG. 10, natural type miR-34a of the Example inhibited expression of AXL mRNA at the same level as that by the positive control pre-miR-34a variant. In addition, an inhibitory effect on the expression of AXL mRNA was maintained even when the base sequence of the additional sequence (3, 5 or 7 base length) in the X region is different.

Example 10

Based on the sequence information of the guide strand and the passenger strand of mature miR-29b (miRBase Accession No. MI0000105), various natural type miRNAs of the present invention having a different base sequence of the additional sequence (0, 3, 5 or 7 base length) in the X region were synthesized, introduced into cultured cells and an inhibitory effect on the expression of the target gene COL1A1 mRNA was examined.

(1) Synthesis of miRNA

By a method similar to that in Example 5, various natural type miR-29b wherein X region composed of the passenger strand (SEQ ID NO: 10) and an additional sequence (0, 3, 5 or 7 base length), and Y region having, at the 5'-terminus of the guide strand, an overhang region of the aforementioned passenger strand and a sequence complementary (sequence completely complementary or partially complementary) to the aforementioned additional sequence, are linked via a non-nucleotide structure of a proline derivative, were synthesized.

PH-0040

(SEQ ID NO: 28)

GCUGGUUUCA$^U$AUGGUG$^{GU}$UUAGA
UUGUGACUAAAGU$_U$UACCAC--GAUCU$^P$ spacer 3

PH-0042

(SEQ ID NO: 29)

GCUGGUUUCA$^U$AUGGUG$^{GU}$UUAGAUCC
UUGUGACUAAAGU$_U$UACCAC--GAUCUAGG$^P$

PH-0109

(SEQ ID NO: 44)

GCUGGUUUCA$^U$AUGGUG$^{GU}$UUAGAUAA
UUGUGACUAAAGU$_U$UACCAC--GAUCUAUU$^P$

PH-0110

(SEQ ID NO: 45)

GCUGGUUUCA$^U$AUGGUG$^{GU}$UUAGAUGG
UUGUGACUAAAGU$_U$UACCAC--GAUCUAUU$^P$

PH-0111

(SEQ ID NO: 46)

GCUGGUUUCA$^U$AUGGUG$^{GU}$UUAGACGG
UUGUGACUAAAGU$_U$UACCAC--GAUCUGCC$^P$

PH-0112

(SEQ ID NO: 47)

GCUGGUUUCA$^U$AUGGUG$^{GU}$UUAGACAA
UUGUGACUAAAGU$_U$UACCAC--GAUCUGUU$^P$

PH-0113

(SEQ ID NO: 48)

GCUGGUUUCA$^U$AUGGUG$^{GU}$UUAGACGG
UUGUGACUAAAGU$_U$UACCAC--GAUCUGUU$^P$

PH-0114

(SEQ ID NO: 49)

GCUGGUUUCA$^U$AUGGUG$^{GU}$UUAGAUGG
UUGUGACUAAAGU$_U$UACCAC--GAUCUGCC$^P$

PH-0115

(SEQ ID NO: 50)

GCUGGUUUCA$^U$AUGGUG$^{GU}$UUAGAUAA
UUGUGACUAAAGU$_U$UACCAC--GAUCUGUU$^P$

PH-0116

(SEQ ID NO: 51)

GCUGGUUUCA$^U$AUGGUG$^{GU}$UUAGAUGG
UUGUGACUAAAGU$_U$UACCAC--GAUCUGUU$^P$ spacer 5

-continued

PH-0108

(SEQ ID NO: 33)

```
     GCUGGUUUCA^U AUGGUG^GU UUAGAUCCGG
UUGUGACUAAAGU_U UACCAC - - GAUCUAGGCC_P
```

PH-0117

(SEQ ID NO: 52)

```
     GCUGGUUUCA^U AUGGUG^GU UUAGAUAAUU
UUGUGACUAAAGU_U UACCAC - - GAUCUAUUAA_P
```

[spacer 7]

PH-0118

(SEQ ID NO: 53)

```
     GCUGGUUUCA^U AUGGUG^GU UUAGAUCCGGCC
UUGUGACUAAAGU_U UACCAC - - GAUCUAGGCCGG_P
```

PH-0119

(SEQ ID NO: 54)

```
     GCUGGUUUCA^U AUGGUG^GU UUAGAUAAUUAA
UUGUGACUAAAGU_U UACCAC - - GAUCUAUUAAUU_P
```

In the aforementioned sequence, the number after the "spacer" shows the base length of the additional sequence of the aforementioned X region.

In the following sequence, the 5'-side region of the linker is X region, in the aforementioned X region, lower-case letters show the aforementioned passenger strand sequence, the rest is the aforementioned additional sequence, and the 3'-side region of the linker is Y region, and in the aforementioned Y region, the underlined part is the aforementioned guide strand sequence. [P] shows a non-nucleotide structure of the aforementioned proline derivative.

PH-0040

(SEQ ID NO: 28)

5'-gcugguuucauauggugguuuaga-[P]-
U<u>CUAGCACCAUUUGAAAUCAGUGUU</u>-3'

PH-0042

(SEQ ID NO: 29)

5'-gcugguuucauauggugguuuagaUCC-[P]-
GGAU<u>CUAGCACCAUUUGAAAUCAGUGUU</u>-3'

PH-0109

(SEQ ID NO: 44)

5'-gcugguuucauauggugguuuagaUAA-[P]-
UUAU<u>CUAGCACCAUUUGAAAUCAGUGUU</u>-3'

PH-0110

(SEQ ID NO: 45)

5'-gcugguuucauauggugguuuagaUGG-[P]-
UUAU<u>CUAGCACCAUUUGAAAUCAGUGUU</u>-3'

PH-0111

(SEQ ID NO: 46)

5'-gcugguuucauauggugguuuagaCGG-[P]-
CCGU<u>CUAGCACCAUUUGAAAUCAGUGUU</u>-3'

PH-0112

(SEQ ID NO: 47)

5'-gcugguuucauauggugguuuagaCAA-[P]-
UUGU<u>CUAGCACCAUUUGAAAUCAGUGUU</u>-3'

PH-0113

(SEQ ID NO: 48)

5'-gcugguuucauauggugguuuagaCGG-[P]-
UUGU<u>CUAGCACCAUUUGAAAUCAGUGUU</u>-3'

PH-0114

(SEQ ID NO: 49)

5'-gcugguuucauauggugguuuagaUGG-[P]-
CCGU<u>CUAGCACCAUUUGAAAUCAGUGUU</u>-3'

PH-0115

(SEQ ID NO: 50)

5'-gcugguuucauauggugguuuagaUAA-[P]-
UUGU<u>CUAGCACCAUUUGAAAUCAGUGUU</u>-3'

PH-0116

(SEQ ID NO: 51)

5'-gcugguuucauauggugguuuagaUGG-[P]-
UUGU<u>CUAGCACCAUUUGAAAUCAGUGUU</u>-3'

PH-0108

(SEQ ID NO: 33)

5'-gcugguuucauauggugguuuagaUCCGG-[P]-
CCGGAU<u>CUAGCACCAUUUGAAAUCAGUGUU</u>-3'

PH-0117

(SEQ ID NO: 52)

5'-gcugguuucauauggugguuuagaUAAUU-[P]-
AAUUAU<u>CUAGCACCAUUUGAAAUCAGUGUU</u>-3'

PH-0118

(SEQ ID NO: 53)

5'-gcugguuucauauggugguuuagaUCCGGCC-[P]-
GGCCGGAU<u>CUAGCACCAUUUGAAAUCAGUGUU</u>-3'

PH-0119

(SEQ ID NO: 54)

5'-gcugguuucauauggugguuuagaUAAUUAA-[P]-
UUAAUUAU<u>CUAGCACCAUUUGAAAUCAGUGUU</u>-3'

As a positive control, NI-0210 of Example 5 was used.

(2) Measurement of Expression Level of COL1A1 Gene

By a method similar to that in Example 5 except that the final concentration of the aforementioned each RNA was 0.5 nmol/L, the expression level of COL1A1 gene was determined.

(3) Results

Figure 11:
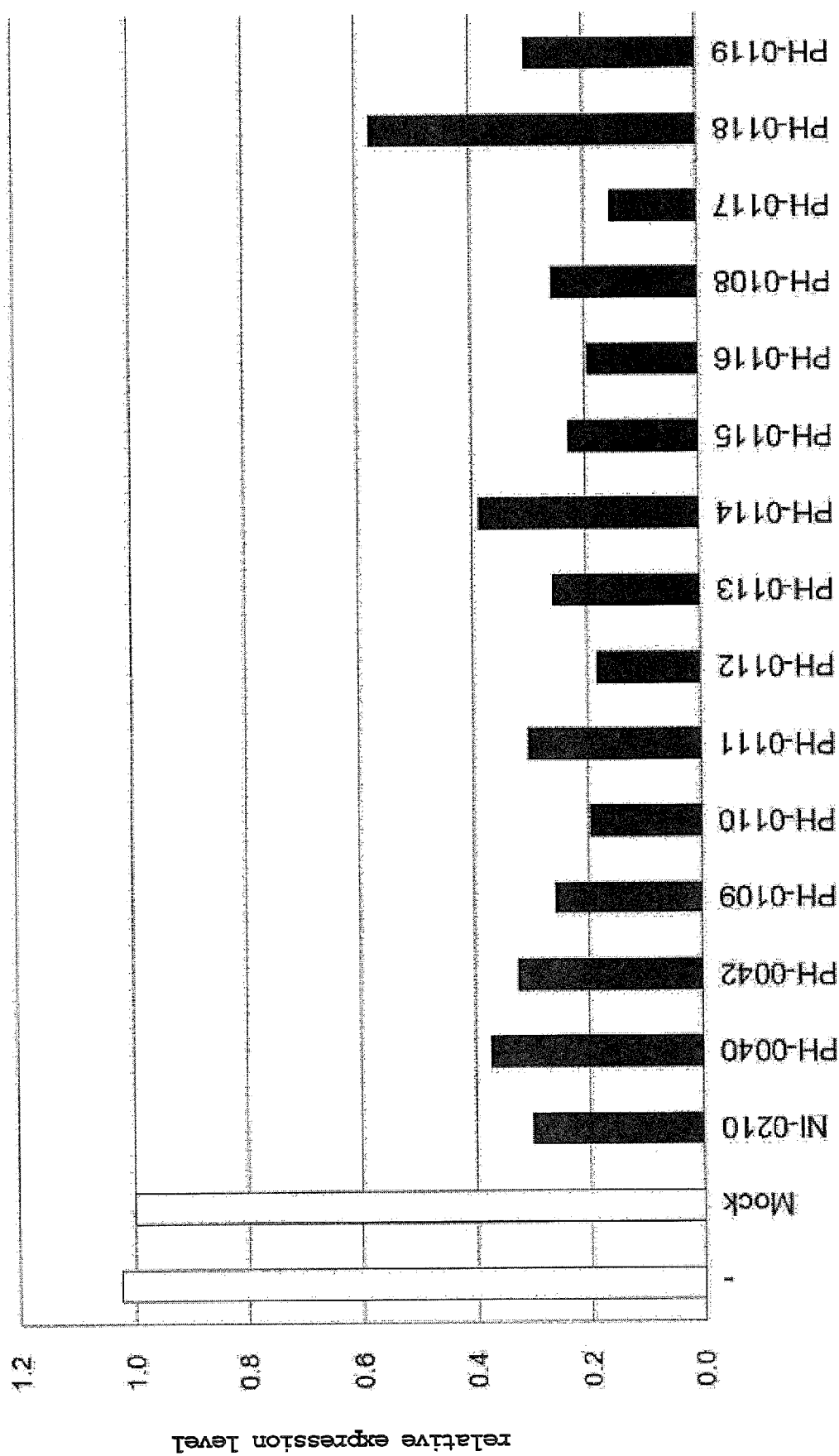
FIG. 11 is a graph showing the relative values of COL1A1 mRNA amount in Example 10.

As shown in FIG. 11, natural type miR-29b of the Example inhibited expression of COL1A1 mRNA at the same level as that by the positive control pre-miR-29b variant. In addition, an inhibitory effect on the expression of COL1A1 mRNA was maintained even when the base sequence of the additional sequence (3, 5 or 7 base length) in the X region is different.

Example 11

Based on the sequence information of the guide strand and the passenger strand of mature miR-29b (miRBase Accession No. MI0000105), various natural type miRNAs of the present invention having a different non-nucleotide structure of the linker region and a different base sequence of the additional sequence (0, 4 or 5 base length) in the X region were synthesized, introduced into cultured cells and an inhibitory effect on the expression of the target gene COL1A1 mRNA was examined.
(1) Synthesis of miRNA By a method similar to that in Example 5, various natural type miR-29b wherein X region composed of the passenger strand (SEQ ID NO: 10) and an additional sequence (0, 4 or 5 base length), and Y region having, at the 5'-terminus of the guide strand, an overhang region of the aforementioned passenger strand and a sequence complementary (sequence completely complementary or partially complementary) to the aforementioned additional sequence, are linked via a linker of proline derivative ([P]) or glycylglycine derivative ([GlyGly]), were synthesized. In the aforementioned synthesis of the natural type miRNA, each non-nucleotide structure was introduced in the same manner as in Examples 1 and 2.

PH-0040

(SEQ ID NO: 28)
GCUGGUUUCA$^U$AUGGUG$^{GU}$UUAGA$_P$
UUGUGACUAAAGU$_U$UACCAC--GAUCU$^P$

PH-0117

(SEQ ID NO: 52)
GCUGGUUUCA$^U$AUGGUG$^{GU}$UUAGAUAAUU$_P$
UUGUGACUAAAGU$_U$UACCAC--GAUCUAUUAA$^P$

PH-0120

(SEQ ID NO: 55)
GCUGGUUUCA$^U$AUGGUG$^{GU}$UUAGAUUUU$_P$
UUGUGACUAAAGU$_U$UACCAC--GAUCUAAAA$^P$

PH-0121

(SEQ ID NO: 56)
GCUGGUUUCA$^U$AUGGUG$^{GU}$UUAGAUUUA$_P$
UUGUGACUAAAGU$_U$UACCAC--GAUCUAAAU$^P$

PH-0122

(SEQ ID NO: 57)
GCUGGUUUCA$^U$AUGGUG$^{GU}$UUAGAUUUAU$_P$
UUGUGACUAAAGU$_U$UACCAC--GAUCUAAAUA$^P$

PH-0123

(SEQ ID NO: 58)
GCUGGUUUCA$^U$AUGGUG$^{GU}$UUAGAUUAUU$_P$
UUGUGACUAAAGU$_U$UACCAC--GAUCUAAUAA$^P$

PH-0124

(SEQ ID NO: 59)
GCUGGUUUCA$^U$AUGGUG$^{GU}$UUAGAUAUUU$_P$
UUGUGACUAAAGU$_U$UACCAC--GAUCUAUAAA$^P$

PH-0125

(SEQ ID NO: 60)
GCUGGUUUCA$^U$AUGGUG$^{GU}$UUAGAUUUAA$_P$
UUGUGACUAAAGU$_U$UACCAC--GAUCUAAAUU$^P$

PH-0126

(SEQ ID NO: 61)
GCUGGUUUCA$^U$AUGGUG$^{GU}$UUAGAUUAUA$_P$
UUGUGACUAAAGU$_U$UACCAC--GAUCUAAUAU$^P$

PH-0127

(SEQ ID NO: 62)
GCUGGUUUCA$^U$AUGGUG$^{GU}$UUAGAUAUUA$_P$
UUGUGACUAAAGU$_U$UACCAC--GAUCUAUAAU$^P$

PH-0128

(SEQ ID NO: 63)
GCUGGUUUCA$^U$AUGGUG$^{GU}$UUAGAUUAAU$_P$
UUGUGACUAAAGU$_U$UACCAC--GAUCUAAUUA$^P$

PH-0129

(SEQ ID NO: 64)
GCUGGUUUCA$^U$AUGGUG$^{GU}$UUAGAUAUAU$_P$
UUGUGACUAAAGU$_U$UACCAC--GAUCUAUAUA$^P$

PH-0130

(SEQ ID NO: 65)
GCUGGUUUCA$^U$AUGGUG$^{GU}$UUAGAUUAAA$_P$
UUGUGACUAAAGU$_U$UACCAC--GAUCUAAUUU$^P$

PH-0131

(SEQ ID NO: 66)
GCUGGUUUCA$^U$AUGGUG$^{GU}$UUAGAUAUAA$_P$
UUGUGACUAAAGU$_U$UACCAC--GAUCUAUAUU$^P$

PH-0132

(SEQ ID NO: 67)
GCUGGUUUCA$^U$AUGGUG$^{GU}$UUAGAUAAUA$_P$
UUGUGACUAAAGU$_U$UACCAC--GAUCUAUUAU$^P$

PH-0133

(SEQ ID NO: 68)
GCUGGUUUCA$^U$AUGGUG$^{GU}$UUAGAUAAAU$_P$
UUGUGACUAAAGU$_U$UACCAC--GAUCUAUUUA$^P$

PH-0134

(SEQ ID NO: 69)
GCUGGUUUCA$^U$AUGGUG$^{GU}$UUAGAUAAAA$_P$
UUGUGACUAAAGU$_U$UACCAC--GAUCUAUUUU$^P$

PH-0135

(SEQ ID NO: 70)
GCUGGUUUCA$^U$AUGGUG$^{GU}$UUAGAUUGG$_P$
UUGUGACUAAAGU$_U$UACCAC--GAUCUAAAUU$^P$

PH-0136

(SEQ ID NO: 71)
GCUGGUUUCA$^U$AUGGUG$^{GU}$UUAGAUUUU$_P$
UUGUGACUAAAGU$_U$UACCAC--GAUCUAAAUU$^P$

PH-0137

(SEQ ID NO: 72)
GCUGGUUUCA$^U$AUGGUG$^{GU}$UUAGAAUUAA$_P$
UUGUGACUAAAGU$_U$UACCAC--GAUCUUAAUU$^P$

PH-0138

(SEQ ID NO: 73)
GCUGGUUUCA$^U$AUGGUG$^{GU}$UUAGAAUUUU$_P$
UUGUGACUAAAGU$_U$UACCAC--GAUCUUAAAA$^P$

PH-0139

(SEQ ID NO: 74)
GCUGGUUUCA$^U$AUGGUG$^{GU}$UUAGACUAA$_P$
UUGUGACUAAAGU$_U$UACCAC--GAUCUGAAUU$^P$

PH-0140

(SEQ ID NO: 75)
GCUGGUUUCA$^U$AUGGUG$^{GU}$UUAGACUUUU$_P$
UUGUGACUAAAGU$_U$UACCAC--GAUCUGAAAA$^P$

-continued

PH-0141

(SEQ ID NO: 76)

GCUGGUUUCA$^U$AUGGUG$^{GU}$UUAGAGUUAA
UUGUGACUAAAGU$_U$UACCAC--GAUCUCAAUU$^P$

PH-0142

(SEQ ID NO: 77)

GCUGGUUUCA$^U$AUGGUG$^{GU}$UUAGAGUUUU
UUGUGACUAAAGU$_U$UACCAC--GAUCUCAAAA$^P$

XH-0059

(SEQ ID NO: 60)

GCUGGUUUCA$^U$AUGGUG$^{GU}$UUAGAUUAA
UUGUGACUAAAGU$_U$UACCAC--GAUCUAAAUU$^{GlyGly}$

PH-0143

(SEQ ID NO: 78)

GCUGGUUUCA$^U$AUGGUG$^{GU}$UUAGAUAAU
UUGUGACUAAAGU$_U$UACCAC--GAUCUAUUA$^P$

PH-0144

(SEQ ID NO: 79)

GCUGGUUUCA$^U$AUGGUG$^{GU}$UUAGAUUAA
UUGUGACUAAAGU$_U$UACCAC--GAUCUAAUU$^P$

PH-0145

(SEQ ID NO: 80)

GCUGGUUUCA$^U$AUGGUG$^{GU}$UUAGAUUGG
UUGUGACUAAAGU$_U$UACCAC--GAUCUAAUU$^P$

PH-0146

(SEQ ID NO: 81)

GCUGGUUUCA$^U$AUGGUG$^{GU}$UUAGAUUUU
UUGUGACUAAAGU$_U$UACCAC--GAUCUAUUU$^P$

In the following sequence, [P] shows a non-nucleotide structure of the proline derivative, and [GlyGly] shows a non-nucleotide structure of the glycylglycine derivative. In the following sequences, the 5'-side region of each linker is X region, in the aforementioned X region, lower-case letters show the aforementioned passenger strand sequence, the rest is the aforementioned additional sequence, the 3'-side region of each linker is Y region, and in the aforementioned Y region, the underlined part is the aforementioned guide strand sequence.

PH-0040

(SEQ ID NO: 28)

5'-gcugguuucauauggugguuuaga-[P]-UC<u>UAGCACCAUUUGAAAUCAGUGUU</u>-3'

PH-0117

(SEQ ID NO: 52)

5'-gcugguuucauauggugguuuagaUAAUU-[P]-AAUUAUC<u>UAGCACCAUUUGAAAUCAGUGUU</u>-3'

PH-0120

(SEQ ID NO: 55)

5'-gcugguuucauauggugguuuagaUUUUU-[P]-AAAAAUC<u>UAGCACCAUUUGAAAUCAGUGUU</u>-3'

PH-0121

(SEQ ID NO: 56)

5'-gcugguuucauauggugguuuagaUUUUA-[P]-UAAAAUC<u>UAGCACCAUUUGAAAUCAGUGUU</u>-3'

PH-0122

(SEQ ID NO: 57)

5'-gcugguuucauauggugguuuagaUUUAU-[P]-AUAAAUC<u>UAGCACCAUUUGAAAUCAGUGUU</u>-3'

PH-0123

(SEQ ID NO: 58)

5'-gcugguuucauauggugguuuagaUUAUU-[P]-AAUAAUC<u>UAGCACCAUUUGAAAUCAGUGUU</u>-3'

PH-0124

(SEQ ID NO: 59)

5'-gcugguuucauauggugguuuagaUAUUU-[P]-AAAUAUC<u>UAGCACCAUUUGAAAUCAGUGUU</u>-3'

PH-0125

(SEQ ID NO: 60)

5'-gcugguuucauauggugguuuagaUUUAA-[P]-UUAAAUC<u>UAGCACCAUUUGAAAUCAGUGUU</u>-3'

PH-0126

(SEQ ID NO: 61)

5'-gcugguuucauauggugguuuagaUUAUA-[P]-UAUAAUC<u>UAGCACCAUUUGAAAUCAGUGUU</u>-3'

PH-0127

(SEQ ID NO: 62)

5'-gcugguuucauauggugguuuagaUAUUA-[P]-UAAUAUC<u>UAGCACCAUUUGAAAUCAGUGUU</u>-3'

PH-0128

(SEQ ID NO: 63)

5'-gcugguuucauauggugguuuagaUUAAU-[P]-AUUAAUC<u>UAGCACCAUUUGAAAUCAGUGUU</u>-3'

PH-0129

(SEQ ID NO: 64)

5'-gcugguuucauauggugguuuagaUAUAU-[P]-AUAUAUC<u>UAGCACCAUUUGAAAUCAGUGUU</u>-3'

PH-0130

(SEQ ID NO: 65)

5'-gcugguuucauauggugguuuagaUUAAA-[P]-UUUAAUC<u>UAGCACCAUUUGAAAUCAGUGUU</u>-3'

PH-0131

(SEQ ID NO: 66)

5'-gcugguuucauauggugguuuagaUAUAA-[P]-UUAUAUC<u>UAGCACCAUUUGAAAUCAGUGUU</u>-3'

PH-0132

(SEQ ID NO: 67)

5'-gcugguuucauauggugguuuagaUAAUA-[P]-UAUUAUC<u>UAGCACCAUUUGAAAUCAGUGUU</u>-3'

PH-0133

(SEQ ID NO: 68)

5'-gcugguuucauauggugguuuagaUAAAU-[P]-AUUUAUC<u>UAGCACCAUUUGAAAUCAGUGUU</u>-3'

PH-0134

(SEQ ID NO: 69)

5'-gcugguuucauauggugguuuagaUAAAA-[P]-UUUUAUC<u>UAGCACCAUUUGAAAUCAGUGUU</u>-3'

PH-0135
(SEQ ID NO: 70)
5'-gcugguuucauauggugguuuagaUUUGG-[P]-

UUAAAUCUAGCACCAUUUGAAAUCAGUGUU-3'

PH-0136
(SEQ ID NO: 71)
5'-gcugguuucauauggugguuuagaUUUUU-[P]-

UUAAAUCUAGCACCAUUUGAAAUCAGUGUU-3'

PH-0137
(SEQ ID NO: 72)
5'-gcugguuucauauggugguuuagaAUUAA-[P]-

UUAAUUCUAGCACCAUUUGAAAUCAGUGUU-3'

PH-0138
(SEQ ID NO: 73)
5'-gcugguuucauauggugguuuagaAUUUU-[P]-

AAAAUUCUAGCACCAUUUGAAAUCAGUGUU-3'

PH-0139
(SEQ ID NO: 74)
5'-gcugguuucauauggugguuuagaCUUAA-[P]-

UUAAGUCUAGCACCAUUUGAAAUCAGUGUU-3'

PH-0140
(SEQ ID NO: 75)
5'-gcugguuucauauggugguuuagaCUUUU-[P]-

AAAGUCUAGCACCAUUUGAAAUCAGUGUU-3'

PH-0141
(SEQ ID NO: 76)
5'-gcugguuucauauggugguuuagaGUUAA-[P]-

UUAACUCUAGCACCAUUUGAAAUCAGUGUU-3'

PH-0142
(SEQ ID NO: 77)
5'-gcugguuucauauggugguuuagaGUUUU-[P]-

AAAACUCUAGCACCAUUUGAAAUCAGUGUU-3'

PH-0143
(SEQ ID NO: 78)
5'-gcugguuucauauggugguuuagaUAAU-[P]-

AUUAUCUAGCACCAUUUGAAAUCAGUGUU-3'

PH-0144
(SEQ ID NO: 79)
5'-gcugguuucauauggugguuuagaUUAA-[P]-

UUAAUCUAGCACCAUUUGAAAUCAGUGUU-3'

PH-0145
(SEQ ID NO: 80)
5'-gcugguuucauauggugguuuagaUUGG-[P]-

UUAAUCUAGCACCAUUUGAAAUCAGUGUU-3'

PH-0146
(SEQ ID NO: 81)
5'-gcugguuucauauggugguuuagaUUUU-[P]-

UUUAUCUAGCACCAUUUGAAAUCAGUGUU-3'

XH-0059
(SEQ ID NO: 60)
5'-gcugguuucauauggugguuuagaUUUAA-[GlyGly]-

UUAAAUCUAGCACCAUUUGAAAUCAGUGUU-3'

As a positive control, NI-0210 of Example 5 was used.

(2) Measurement of Expression Level of COL1A1 Gene

By a method similar to that in Example 5 except that the final concentration of the aforementioned each RNA was 0.5 nmol/L, the expression level of COL1A1 gene was determined.

(3) Results

Figure 12:
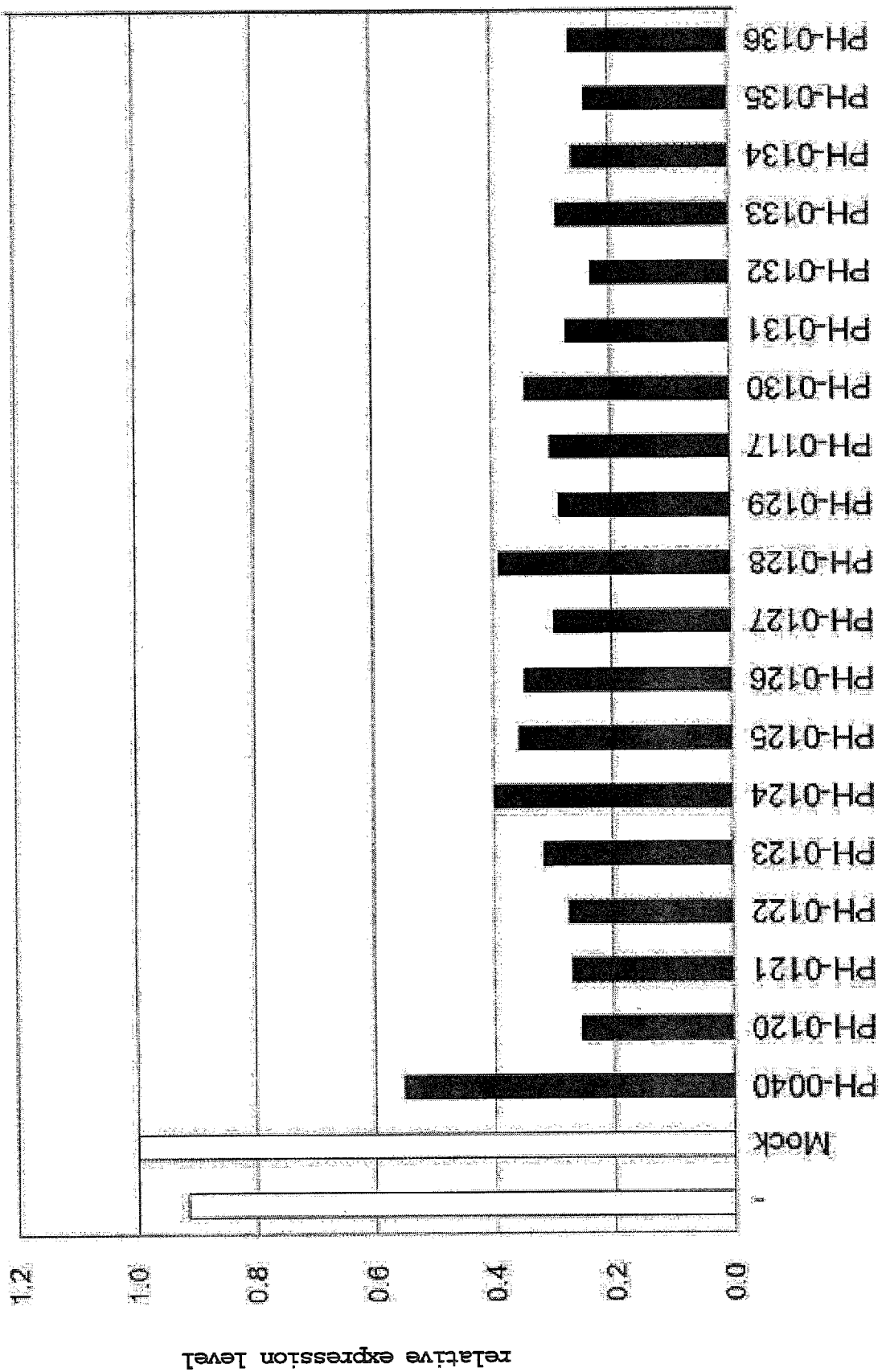
FIG. 12 is a graph showing the relative values of COL1A1 mRNA amount in Example 11.
Figure 13:
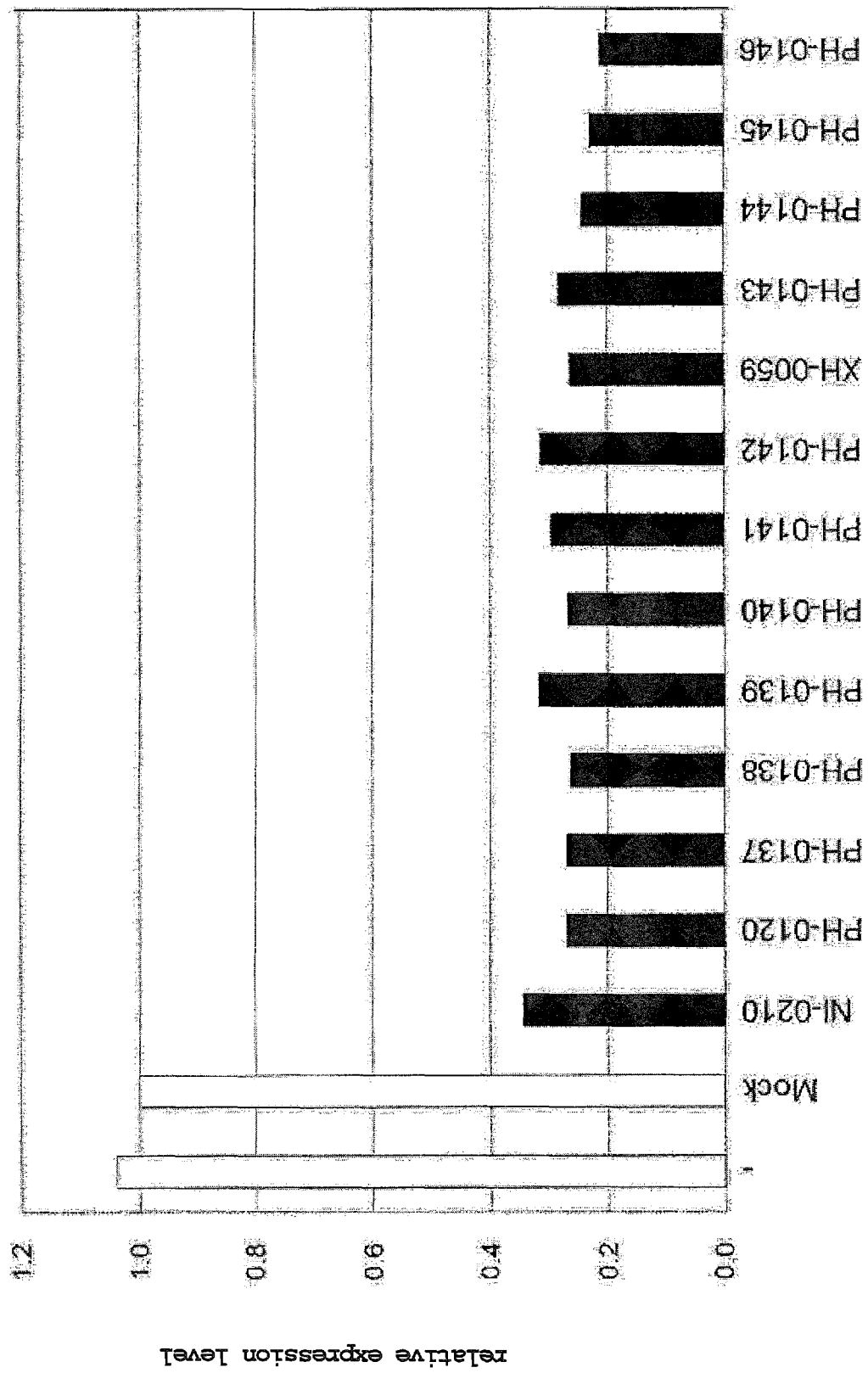
FIG. 13 is a graph showing the relative values of COL1A1 mRNA amount in Example 11.

As shown in FIGS. 12 and 13, natural type miR-29b of the Example inhibited expression of COL1A1 mRNA at the same level as that by the positive control pre-miR-29b variant. In addition, an inhibitory effect on the expression of COL1A1 mRNA was maintained even when the base sequence of the additional sequence (4 or 5 base length) in the X region was different.

While the present invention has been described above with reference to illustrative embodiments, the present invention is by no means limited thereto. Various changes that may become apparent to those skilled in the art may be made in the configuration and specifics of the present invention without departing from the scope of the present invention.

In addition, the contents disclosed in any publication cited herein, including patents and patent applications, are hereby incorporated in their entireties by reference, to the extent that they have been disclosed herein.

INDUSTRIAL APPLICABILITY

Since the natural type miRNA of the present invention can be easily synthesized at a low cost, and can inhibit the translation of a protein encoded by the aforementioned gene. Therefore, a natural type miRNA of the present invention is useful as, for example, a pharmaceutical product, a diagnostic agent, an agricultural chemical, and a tool for conducting research on agriculture, medical science, life science, and the like.

This application is based on a patent application Nos. 2014-266918 filed in Japan (filing date: Dec. 27, 2014) and 2015-130496 filed in Japan (filing date: Jun. 29, 2015), the contents of which are incorporated in full herein.

The invention claimed is:

1. A single-stranded nucleic acid comprising X region and Y region,
wherein
the 3'-terminus of said X region and the 5'-terminus of said Y region are linked via a linker region of a non-nucleotide structure,
said X region comprises (a) a guide strand sequence or (b) a passenger strand sequence of a mature miRNA,
when the X region comprises (a), said Y region comprises a passenger strand sequence of said mature miRNA,
when the X region comprises (b), said Y region comprises a guide strand sequence of said mature miRNA,
said X region further comprises an additional sequence of 3-5 base length, and
said guide strand sequence and said passenger strand sequence form a double-stranded structure.

2. The single-stranded nucleic acid according to claim 1, wherein when said Y region and said X region are aligned, said Y region has an overhang on the 3'-terminus.

3. The single-stranded nucleic acid according to claim 2, wherein said overhang has a 1-4 base length.

4. The single-stranded nucleic acid according to claim 1, wherein said X region comprises said guide strand or passenger strand sequence and said additional sequence, and said additional sequence is linked to the 3'-terminus of said guide strand or passenger strand sequence.

5. The single-stranded nucleic acid according to claim 1, wherein said X region has a length of 19-35 bases, and/or said Y region has a length of 21-37 bases, and/or the full length miRNA has a 40-68 base length.

6. The single-stranded nucleic acid according to claim 1, wherein said linker region comprises at least one selected from the group consisting of an amino acid residue, a polyamine residue, and a polycarboxylic acid residue.

7. The single-stranded nucleic acid according to claim 6, wherein said polycarboxylic acid residue is a terephthalic acid residue.

8. The single-stranded nucleic acid according to claim 6, wherein said amino acid residue is a glycine residue, a terephthalic acid amide residue, a proline residue or a lysine residue.

9. The single-stranded nucleic acid according to claim 6, wherein said amino acid residue comprises a plurality of amino acid residues linked to each other.

10. The single-stranded nucleic acid according to claim 9, wherein said plurality of amino acid residues are linked to form a residue of a glycine dimer or trimer.

11. The single-stranded nucleic acid according to claim 1, wherein said linker residue is represented by the following chemical formula (I-0):

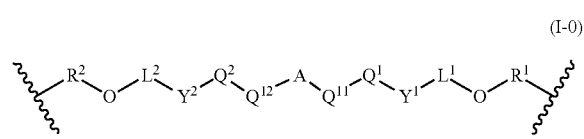

(I-0)

in said chemical formula (I-0),
$Q^{11}$ and $Q^{12}$ are each independently a single bond, $CH_2$ (a methylene group), NH (an imino group), C=O (a carbonyl group), C=S (a thiocarbonyl group), C=NH (an iminomethylene group), O, or S,
$Q^1$ and $Q^2$ are each independently a single bond, $CH_2$ (a methylene group), NH (an imino group), C=O (a carbonyl group), C=S (a thiocarbonyl group), C=NH (an iminomethylene group), O, or S,
$Y^1$ and $Y^2$ are each independently a single bond, $CH_2$, NH, O, or S;
$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or,
$L^1$ is a polyether chain obtained by substituting at least one carbon atom on said alkylene chain with an oxygen atom,
provided that: when $Y^1$ is NH, O, or S, an atom bound to $Y^1$ in $L^1$ is carbon, an atom bound to $OR^1$ in $L^1$ is carbon, and oxygen atoms are not adjacent to each other;
$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or
$L^2$ is a polyether chain obtained by substituting at least one carbon atom on said alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

said regions X and Y are each linked to said linker residue via —$OR^1$— or —$OR^2$—, wherein $R^1$ and $R^2$ may or may not be present, and when they are present, $R^1$ and $R^2$ are each independently a nucleotide residue or said structure (I-0); and A is any atomic group.

12. The single-stranded nucleic acid according to claim 1, wherein said linker region comprises an amino acid residue, and said amino acid residue is represented by the following chemical formula (I):

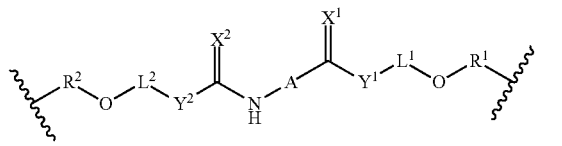
(I)

in said chemical formula (I), $X^1$ and $X^2$ are each independently $H_2$, O, S or NH;

$Y^1$ and $Y^2$ are each independently a single bond, $CH_2$, NH, O or S;

$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or, $L^1$ is a polyether chain obtained by substituting at least one carbon atom on said alkylene chain with an oxygen atom, provided that: when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on said alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

said regions X and Y are each linked to said amino acid residue via —$OR^1$— or —$OR^2$—, wherein $R^1$ and $R^2$ may or may not be present, and when they are present, $R^1$ and $R^2$ are each independently a nucleotide residue or said structure (I); and A is any atomic group, provided that the following chemical formula (Ia) is an amino acid or peptide:

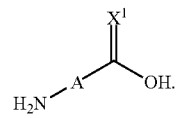
(Ia)

13. The single-stranded nucleic acid according to claim 11, wherein said chemical formula (I-0) or (I) has a structure of the following chemical formulae (I-1)-(I-7) and, in the following chemical formulae (I-1)-(I-7), n is an integer of 0-30, and m is an integer of 0-30:

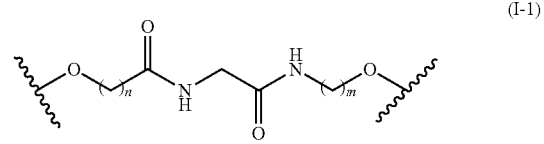
(I-1)

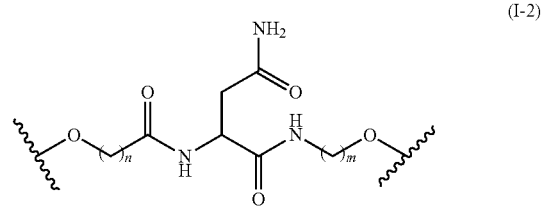
(I-2)

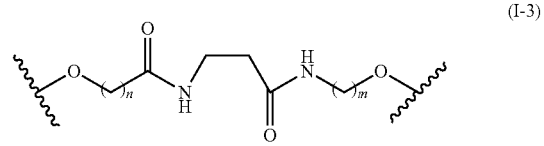
(I-3)

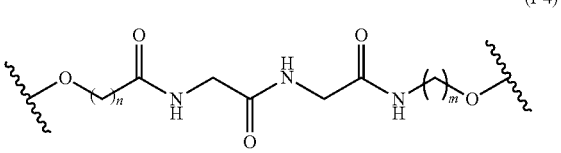
(I-4)

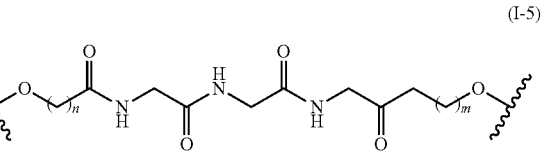
(I-5)

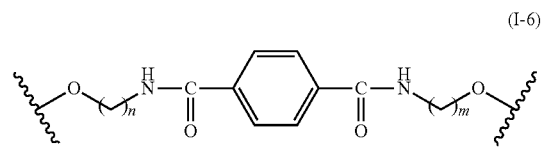
(I-6)

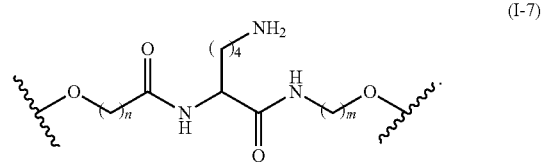
(I-7)

14. The single-stranded nucleic acid according to claim 13, wherein, (i) in said chemical formula (I-1), n=11 and m=12, or n=5 and m=4;

(ii) in said chemical formula (I-4), n=5 and m=4;

(iii) in said chemical formula (I-6), n=4 and m=4; or (iv) in said chemical formula (I-7), n=5 and m=4.

15. The single-stranded nucleic acid according to claim 1, wherein a non-nucleotide structure of said linker region comprises at least one of a pyrrolidine skeleton and a piperidine skeleton.

16. The single-stranded nucleic acid according to claim 1, wherein said non-nucleotide structure is represented by the following formula (II):

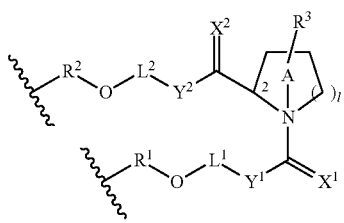

(II)

wherein
$X^1$ and $X^2$ are each independently $H_2$, O, S, or NH;
$Y^1$ and $Y^2$ are each independently a single bond, $CH_2$, NH, O, or S;
$R^3$ is a hydrogen atom or a substituent which is bonded to C-3, C-4, C-5 or C-6 on ring A,
$L^1$ is an alkylene chain having n atoms, and a hydrogen atom on an alkylene carbon atom may or may not be substituted with OH, $OR^a$, $NH_2$, $NHR^a$, $NR^aR^b$, SH, or $SR^a$, or,
$L^1$ is a polyether chain obtained by substituting at least one carbon atom on said alkylene chain with an oxygen atom,
provided that: when $Y^1$ is NH, O, or S, an atom bound to $Y^1$ in $L^1$ is carbon, an atom bound to $OR^1$ in $L^1$ is carbon, and oxygen atoms are not adjacent to each other;
$L^2$ is an alkylene chain having m atoms, and a hydrogen atom on an alkylene carbon atom may or may not be substituted with OH, $OR^c$, $NH_2$, $NHR^c$, $NR^cR^d$, SH, or $SR^c$, or
$L^2$ is a polyether chain obtained by substituting at least one carbon atom on said alkylene chain with an oxygen atom,
provided that: when $Y^2$ is NH, O, or S, an atom bound to $Y^2$ in $L^2$ is carbon, an atom bound to $OR^2$ in $L^2$ is carbon, and oxygen atoms are not adjacent to each other;
$R^a$, $R^b$, $R^c$, and $R^d$ are each independently a substituent or a protecting group;
l is 1 or 2;
m is an integer in the range from 0 to 30;
n is an integer in the range from 0 to 30; and
in ring A, one carbon atom other than said C-2 on ring A may be substituted by nitrogen, oxygen or sulfur, and may contain, in said ring A, a carbon-carbon double bond or a carbon-nitrogen double bond,
said regions (X) and (Y) are each linked to said non-nucleotide structure via —$OR^1$— or —$OR^2$—,
wherein $R^1$ and $R^2$ may or may not be present, and when they are present, $R^1$ and $R^2$ are each independently a nucleotide residue or said structure (II).

17. The single-stranded nucleic acid according to claim 1, wherein said X region comprises a guide strand sequence of a mature miRNA selected from the group consisting of hsa-miR-34 or hsa-let-7.

18. The single-stranded nucleic acid according to claim 1, wherein said X region comprises a passenger strand sequence of a mature miRNA of hsa-miR-29b.

19. A pharmaceutical composition comprising the single-stranded nucleic acid according to claim 1.

* * * * *